(12) United States Patent
Okumura et al.

(10) Patent No.: US 11,807,596 B2
(45) Date of Patent: Nov. 7, 2023

(54) THIOL COMPOUNDS, SYNTHESIS METHOD THEREFOR, AND UTILIZATION OF SAID THIOL COMPOUNDS

(71) Applicant: SHIKOKU CHEMICALS CORPORATION, Kagawa (JP)

(72) Inventors: Naoto Okumura, Kagawa (JP); Akihito Otsuka, Kagawa (JP); Takeshi Kumano, Kagawa (JP); Kazuyuki Fujikawa, Kagawa (JP); Yusuke Araki, Kagawa (JP)

(73) Assignee: SHIKOKU CHEMICALS CORPORATION, Kagawa (JP)

( * ) Notice: Subject to any disclaimer, the term of this patent is extended or adjusted under 35 U.S.C. 154(b) by 0 days.

(21) Appl. No.: 16/759,089

(22) PCT Filed: Oct. 25, 2018

(86) PCT No.: PCT/JP2018/039645
§ 371 (c)(1),
(2) Date: Apr. 24, 2020

(87) PCT Pub. No.: WO2019/082962
PCT Pub. Date: May 2, 2019

(65) Prior Publication Data
US 2020/0369606 A1 Nov. 26, 2020

(30) Foreign Application Priority Data

Oct. 26, 2017 (JP) ................................. 2017-206993
Nov. 2, 2017 (JP) ................................. 2017-213168
Nov. 2, 2017 (JP) ................................. 2017-213211
Nov. 2, 2017 (JP) ................................. 2017-213229

(51) Int. Cl.
| | |
|---|---|
| *C07C 321/22* | (2006.01) |
| *C08L 63/00* | (2006.01) |
| *C09J 163/00* | (2006.01) |
| *C07C 319/02* | (2006.01) |
| *C07C 319/18* | (2006.01) |
| *C07D 233/34* | (2006.01) |
| *C07D 235/26* | (2006.01) |
| *C08G 59/66* | (2006.01) |
| *C07C 321/14* | (2006.01) |
| *C07C 321/10* | (2006.01) |

(52) U.S. Cl.
CPC .......... *C07C 321/14* (2013.01); *C07C 319/02* (2013.01); *C07C 319/18* (2013.01); *C07C 321/10* (2013.01); *C07C 321/22* (2013.01); *C07D 233/34* (2013.01); *C07D 235/26* (2013.01); *C08G 59/66* (2013.01); *C08L 63/00* (2013.01); *C09J 163/00* (2013.01)

(58) Field of Classification Search
CPC ... C07C 321/14; C07C 321/20; C07C 321/22; C07C 323/17; C07C 323/64; C07C 2601/14; C07C 2601/08; C07C 2601/18
See application file for complete search history.

(56) References Cited

U.S. PATENT DOCUMENTS

| | | | |
|---|---|---|---|
| 2,986,582 A | 5/1961 | Martin et al. | |
| 3,208,969 A | 9/1965 | Quattlebaum et al. | |
| 4,269,731 A * | 5/1981 | Mack ...................... | C07F 9/902 |
| | | | 524/285 |
| 5,430,112 A | 7/1995 | Sakata et al. | |
| 8,017,720 B2 | 9/2011 | Bojkova et al. | |
| 2003/0166808 A1 | 9/2003 | Okazaki et al. | |
| 2007/0142605 A1 | 6/2007 | Bojkova et al. | |
| 2009/0093570 A1 | 4/2009 | Hsu et al. | |
| 2010/0273940 A1 | 10/2010 | Urakawa | |
| 2010/0312004 A1 | 12/2010 | Gorodisher et al. | |
| 2011/0223336 A1 | 9/2011 | Bloomquist et al. | |
| 2012/0286435 A1 | 11/2012 | Bojkova et al. | |
| 2013/0082220 A1 | 4/2013 | Herold et al. | |
| 2013/0225777 A1 | 8/2013 | Hickenboth et al. | |
| 2014/0213690 A1 | 7/2014 | Brandstadt et al. | |
| 2016/0289237 A1 | 10/2016 | Kumano et al. | |
| 2016/0291469 A1* | 10/2016 | Katayama ......... | H01L 21/31116 |

(Continued)

FOREIGN PATENT DOCUMENTS

| | | |
|---|---|---|
| CN | 1404496 | 3/2003 |
| CN | 103781823 | 5/2014 |

(Continued)

OTHER PUBLICATIONS

Orrillo et al. ("Host Amplification in a Dithioacetal-Based Dynamic Covalent Library", Organic Letters, Mar. 2017, vol. 19, Issue 6, pp. 1446-1449 (Year: 2017).*
Kornilovitch et al. ("Current rectification by molecules with asymmetric tunneling barriers", Physical Review B, vol. 66, Issue 16, Oct. 2002, pp. 165436-1 to 165436-11). (Year: 2002).*
Ishii et al. (Schemes 1-5 from "Syntheses, structures, and complexation of cis and trans-cycloheptane-1,2-diyl-fused crown thioethers ([12]ansS4)", Heteroatom Chemistry, 2011, vol. 22, Issues 3-4, pp. 388-396, 3 pages). (Year: 2011).*
Antimony mercaptocarboxylic acid esters of U.S. Pat. No. 4,269,731, 12 pages, patented May 1981 (Year: 1981).*

(Continued)

*Primary Examiner* — Rosalynd A Keys
(74) *Attorney, Agent, or Firm* — Wenderoth, Lind & Ponack, L.L.P.

(57) ABSTRACT

The purpose of the present invention is to provide: novel thiol compounds; a method for synthesizing said thiol compounds; curing agents containing said thiol compounds; resin compositions containing said thiol compounds and an epoxy compound; and resin compositions containing said thiol compounds and an ene compound having a carbon-carbon double bond in a molecule. Furthermore, the purpose of the present invention is to provide adhesives and sealants having these resin compositions as ingredients. The thiol compounds of the present invention are represented by chemical formula (I) to chemical formula (VII).

11 Claims, 8 Drawing Sheets

(56) References Cited

U.S. PATENT DOCUMENTS

| | | | |
|---|---|---|---|
| 2017/0007505 A1 | 1/2017 | Moszner et al. | |
| 2017/0114208 A1* | 4/2017 | Rao | C08G 75/06 |
| 2017/0129986 A1 | 5/2017 | Boghossian et al. | |
| 2018/0051128 A1 | 2/2018 | Iwaya et al. | |
| 2019/0040178 A1 | 2/2019 | Rivieres et al. | |
| 2020/0369606 A1 | 11/2020 | Okumura et al. | |

FOREIGN PATENT DOCUMENTS

| | | | | |
|---|---|---|---|---|
| GB | 786178 | * | 11/1957 | |
| JP | 02-274705 | | 11/1990 | |
| JP | 02274705 | A * | 11/1990 | C08F 20/38 |
| JP | 06-211969 | | 8/1994 | |
| JP | 06-211970 | | 8/1994 | |
| JP | 10-330450 | | 12/1998 | |
| JP | 2002-201281 | | 7/2002 | |
| JP | 2002-284860 | | 10/2002 | |
| JP | 2004-099751 | | 4/2004 | |
| JP | 2006-117881 | | 5/2006 | |
| JP | 2006-282988 | | 10/2006 | |
| JP | 2009-520058 | | 5/2009 | |
| JP | 2014-058667 | | 4/2014 | |
| JP | 2014-510168 | | 4/2014 | |
| JP | 2014-526575 | | 10/2014 | |
| JP | 2014208605 | A * | 11/2014 | C07C 321/28 |
| JP | 2016-66605 | | 4/2016 | |
| KR | 20160093176 | A * | 8/2016 | C07C 321/22 |
| TW | 200936631 | | 12/1997 | |
| WO | 98/23606 | | 6/1998 | |
| WO | 98/40169 | | 9/1998 | |
| WO | 98/58294 | | 12/1998 | |
| WO | 02/36662 | | 5/2002 | |
| WO | 03/081295 | | 10/2003 | |
| WO | 2012/093510 | | 7/2012 | |
| WO | 2013/036546 | | 3/2013 | |
| WO | 2016/143847 | | 9/2016 | |
| WO | 2017/074911 | | 5/2017 | |
| WO | 2017/129661 | | 8/2017 | |
| WO | 2019/082962 | | 5/2019 | |

OTHER PUBLICATIONS

Office Action dated May 24, 2021 in corresponding Taiwanese Patent Application No. 107138030, with English translation.
Extended European Search Report dated Jun. 21, 2021 in corresponding European Patent Application No. 18871107.1.
International Search Report dated Jan. 29, 2019 in International (PCT) Application No. PCT/JP2018/039645; with English Translation.
Clark R. et al, "Synthesis of Some Substituted Benzimidazolones" J. Am. Chem. Soc., 1958, vol. 80, pp. 1657-1662.
Kornblum N. et al., "Heterogeneity as a Factor in the Alkylation of Ambident Anions: Phenoxide Ions", J. Am. Chem. Soc., 1959, vol. 81, pp. 2705-2715.
Amorati R. et al., "Effect of ortho-SR Groups on O—H Bond Strength and H-Atom Donating Ability of Phenols: A Possible Role for the Tyr-Cys Link in Galactose Oxidase Active Site?" J. Am. Chem. Soc., 2008, vol. 130, pp. 237-244.
Vlaminck L. et al., "Lignin inspired phenolic polyethers synthesized via ADMET: Systematic structure-property investigation" European Polymer Journal, 2017, vol. 95, pp. 503-513.
Office Action dated Dec. 13, 2021 in corresponding Japanese Patent Application No. 2018-204188, with English translation.
Office Action dated Sep. 3, 2021 in corresponding Chinese Patent Application No. 201880069073.2, with English translation.
Office Action dated Feb. 21, 2022, in corresponding Japanese Patent Application No. 2018-206257, with English translation.
Tamer Awad Ali et al., "Zinc(II) modified carbon paste electrodes based on self-assembled mercapto compounds-gold-nanoparticles for its determination in water samples", Journal of Industrial and Engineering Chemistry, vol. 20, No. 5, 2014, pp. 3320-3328.
Office Action dated Mar. 22, 2022, in corresponding Chinese Patent Application No. 201880069073.2, with English translation.
Extended European Search Report dated Apr. 12, 2022, in corresponding European Patent Application No. 22150518.3.
Office Action dated Apr. 4, 2022 in corresponding Japanese Patent Application No. 2018-201114, with English language translation.
Office Action dated Apr. 4, 2022 in corresponding Japanese Patent Application No. 2018-201514, with English language translation.
Hon, Yung-Son et al., "Acetonyltriphenylphosphonium Bromide and Its Polymer-Supported Analogues as Catalysts for the Protection of Carbonyl Compounds as Acetals or Thioacetals," Synthetic Communications, vol. 33, No. 16, 2003, pp. 2829-2842.
CAS Registry No. 639079-39-3, Database REGISTRY [online], Retrieved from: STN International, Entered STN, Jan. 19, 2004, with partial English translation.
Office Action dated Aug. 17, 2022 in Japanese Patent Application No. 2018-206257, with English-language translation.
Office Action dated Aug. 23, 2022 in Chinese Patent Application No. 201880069073.2, with English-language translation.
Office Action dated Oct. 28, 2022 in Korean Patent Application No. 10-2020-7011643, with English-language translation.
Vietnamese Office Action dated Dec. 12, 2022 in corresponding Vietnam Patent Application No. 1-2020-02299, with English translation.
Taiwanese Office Action dated Jan. 16, 2023 in corresponding Taiwan Patent Application No. 110135253, with English translation.
Office Action dated Jul. 7, 2023 in corresponding PH patent application No. 1/2020/550455.
Office Action dated Jul. 6, 2023 in corresponding EP patent application No. 18 871 107.1.
Office Action dated Jul. 24, 2023 in Taiwanese Patent Application No. 110135253, with English-language translation.
Office Action dated Aug. 18, 2023 in Chinese Patent Application No. 202111404152.4, with English-language translation.
Office Action dated Aug. 30, 2023 in Chinese Patent Application No. 202111403246.X, with English-language translation.
Registry, RN 2116501-91-6 «STN», Aug. 18, 2017.

* cited by examiner

THIOL COMPOUNDS, SYNTHESIS METHOD THEREFOR, AND UTILIZATION OF SAID THIOL COMPOUNDS

TECHNICAL FIELD

The present invention relates to a new thiol compound, a synthesis method of the thiol compound, and utilization of the thiol compound.

BACKGROUND ART

Compounds having plural thiol groups in the molecule have been known as a curing agent of an epoxy compound (note: epoxy resin before curing).

For example, Patent Literature 1 proposes an epoxy resin composition using a polythiol compound as a curing agent and also containing a reaction product between an amine and an epoxy compound as a curing accelerator. The epoxy resin composition is said to have a long pot life and additionally be promptly cured at relatively low temperature.

Patent Literature 2 proposes an epoxy resin composition containing a reaction product between an isocyanate compound having one or more isocyanate group in the molecule and a compound having at least one primary and/or secondary amino group in the molecule, as a curing accelerator. The epoxy resin composition is also said to have a long pot life and have excellent curability.

Compounds having plural thiol groups in the molecule and enic compounds having a carbon-carbon double bond in the molecule are promptly polymerized (resinified) by a polymerization initiator, and therefore utilization thereof in various uses is being considered.

For example, Patent Literature 3 describes that tris[(3-mercaptopropionyloxy)-ethyl]isocyanurate having three thiol groups in the molecule as a thiol compound is promptly reacted with an enic compound to obtain a cured product having excellent properties.

However, those thiol compounds have an ester bond in the molecule. As a result, there was a problem on moisture resistance of the cured product obtained since the ester bond is decomposed by hydrolysis reaction under humidification conditions.

In addition to those patent literatures, the following Patent Literatures 4 to 8 are listed as literatures describing inventions relating to the present invention.

CITATION LIST

Patent Literature

Patent Literature 1: JP-A-H06-211969
Patent Literature 2: JP-A-H06-211970
Patent Literature 3: JP-A-2014-58667
Patent Literature 4: JP-T-2014-526575
Patent Literature 5: US-A-2017/0129986
Patent Literature 6: WO2002/036662
Patent Literature 7: US-A-2017/0007505
Patent Literature 8: WO1998/58294

SUMMARY OF INVENTION

Technical Problem

An object to the present invention is to provide a new thiol compound, a synthesis method of the thiol compound, a curing agent containing the thiol compound, a resin composition containing the thiol compound and an epoxy compound, and a resin composition containing the thiol compound and an enic compound having a carbon-carbon double bond in the molecule.

An object of the present invention is to further provide an adhesive and sealant, containing those resin compositions as components.

Solution to Problem

As a result of extensive investigations for solving the above-described problems, the present inventors have found that the intended objects can be achieved by thiol compounds having a specific structure, and have completed the present invention.

Specifically, a first invention is a thiol compound represented by any one of the chemical formula (I) to chemical formula (VII).

[Chem. 1]

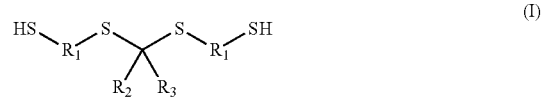

(I)

(In the formula (I), $R_1$'s are the same or different and represent a straight chain alkylene group having a carbon number of 1 to 10, a branched chain alkylene group having a carbon number of 2 to 10, or a divalent organic group represented by each formula of

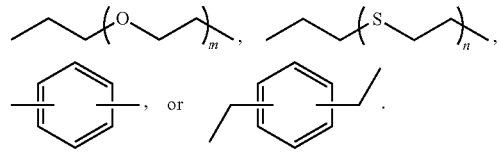

$R_2$ and $R_3$ are the same or different and represent a hydrogen atom, a straight chain alkyl group having a carbon number of 1 to 10, a branched chain alkyl group having a carbon number of 3 to 10, or an aryl group, and $R_2$ and $R_3$ may be linked to form a ring. m is an integer of 1 to 5. n is an integer of 1 to 5.

However, the formula (I) excludes (1) the case where $R_2$ and $R_3$ are simultaneously a hydrogen atom and (2) the case where $R_1$'s are simultaneously

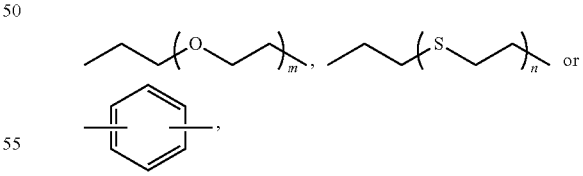

$R_2$ is a methyl group and $R_3$ is a methyl group or an ethyl group.)

[Chem. 2]

(II)

(In the formula (II), $R_{21}$'s are the same or different and represent a straight chain alkylene group having a carbon number of 1 to 10, a branched chain alkylene group having a carbon number of 2 to 10, or a divalent organic group represented by each formula of

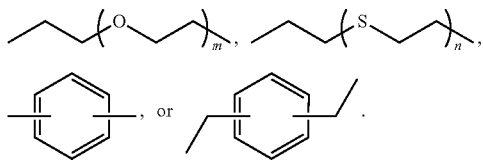

$R_{22}$ represents a divalent organic group represented by each formula of

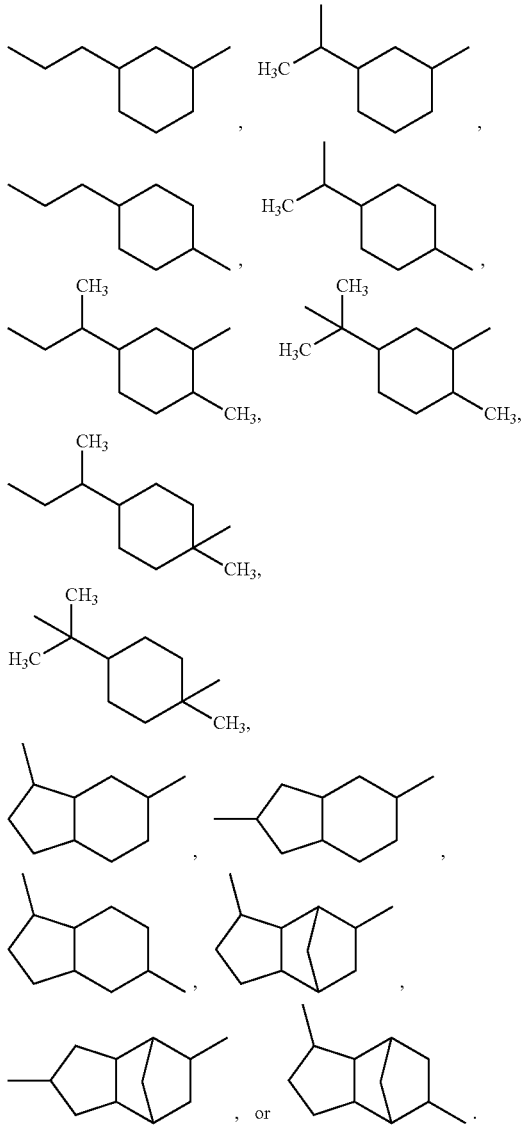

m is an integer of 1 to 5. n is an integer of 1 to 5.

However, the formula (II) excludes the case where $R_{21}$'s are simultaneously

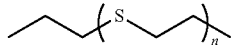

and $R_{22}$ is

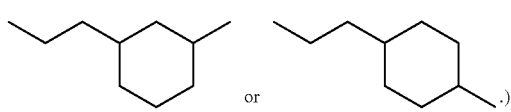

[Chem. 3]

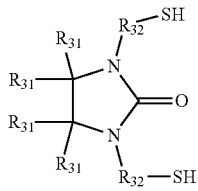

(III)

(In the formula (III), $R_{31}$'s are the same or different and represent a hydrogen atom, a straight chain alkyl group having a carbon number of 1 to 10, a branched chain alkyl group having a carbon number of 3 to 10, or an aryl group. $R_{32}$'s are the same or different and represent a straight chain alkylene group having a carbon number of 2 to 12, a branched chain alkylene group having a carbon number of 3 to 12, or a divalent organic group represented by the following chemical formula (a) to chemical formula (c). However, the formula (III) excludes the case where $R_3$'s are simultaneously a hydrogen atom and $R_{32}$'s are simultaneously an ethylene group.)

[Chem. 4]

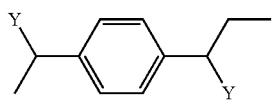 (a)

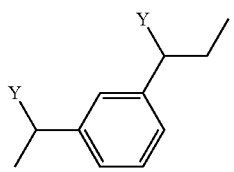 (b)

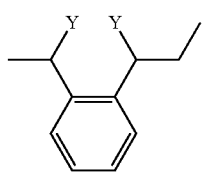 (c)

(In the formulae (a) to formula (c), Y's are the same or different and represent a hydrogen atom or a methyl group.)

[Chem. 5]

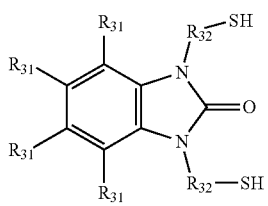
(IV)

(In the formula (IV), $R_{31}$'s and $R_{32}$'s are the same as defined above.)

[Chem. 6]

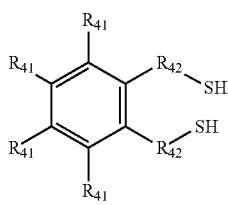
(V)

(In the formula (V), $R_{41}$'s are the same or different and represent a hydrogen atom, a straight chain alkyl group having a carbon number of 1 to 10, a branched chain alkyl group having a carbon number of 3 to 10, or an aryl group. $R_{42}$'s are the same or different and represent a divalent organic group. However, the formula (V) excludes the case where $R_{41}$'s are simultaneously a hydrogen atom and $R_{42}$'s are simultaneously a methylene group or an ethylene group.)

[Chem. 7]

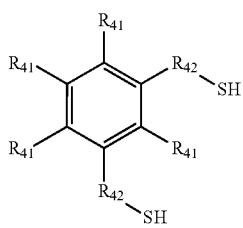
(VI)

(In the formula (VI), $R_{41}$'s and $R_{42}$'s are the same as defined above. However, the formula (VI) excludes the case where $R_{41}$'s are simultaneously a hydrogen atom and $R_{42}$'s are simultaneously a methylene group or an ethylene group.)

[Chem. 8]

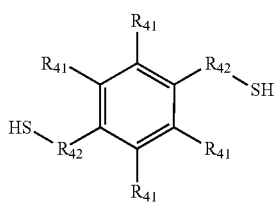
(VII)

(In the formula (VII), $R_{41}$'s and $R_{42}$'s are the same as defined above. However, the formula (VII) excludes the case where $R_{41}$'s are simultaneously a hydrogen atom and $R_{42}$'s are simultaneously a methylene group, an ethylene group or a trimethylene group.)

A second invention is a synthesis method of a thiol compound represented by the chemical formula (I), containing reacting a carbonyl compound represented by the chemical formula (1) with a thiol compound represented by the chemical formula (2).

[Chem. 9]

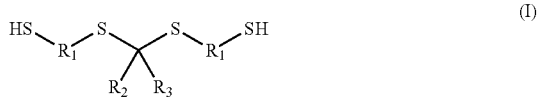
(I)

(In the formula (I), $R_1$'s are the same or different and represent a straight chain alkylene group having a carbon number of 1 to 10, a branched chain alkylene group having a carbon number of 2 to 10, or a divalent organic group represented by each formula of

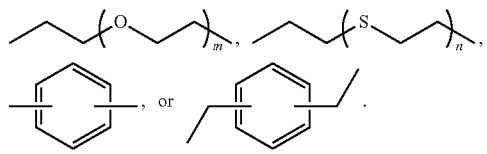

$R_2$ and $R_3$ are the same or different and represent a hydrogen atom, a straight chain alkyl group having a carbon number of 1 to 10, a branched chain alkyl group having a carbon number of 3 to 10, or an aryl group, and $R_2$ and $R_3$ may be linked to form a ring. m is an integer of 1 to 5. n is an integer of 1 to 5.

However, the formula (I) excludes (1) the case where $R_2$ and $R_3$ are simultaneously a hydrogen atom and (2) the case where $R_1$'s are simultaneously

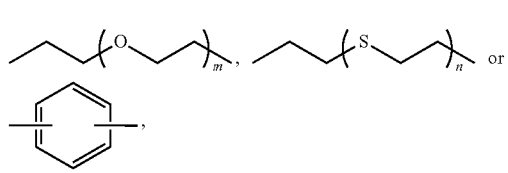

$R_2$ is a methyl group and $R_3$ is a methyl group or an ethyl group.)

[Chem. 10]

(1)

(In the formula (1), $R_2$ and $R_3$ are the same as defined above. However, the formula (1) excludes the case where $R_2$ and $R_3$ are simultaneously a hydrogen atom.)

[Chem. 11]

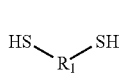
(2)

(In the formula (2), $R_1$ is the same as defined above.)

A third invention is a synthesis method of a thiol compound represented by the chemical formula (II), containing reacting a dialkene compound selected from vinylcyclohexene, limonene, tetrahydroindene, and dicyclopentadiene with a thiol compound represented by the chemical formula (3).

[Chem. 12]

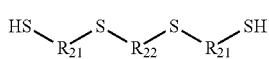
(II)

(In the formula (II), $R_{21}$'s are the same or different and represent a straight chain alkylene group having a carbon number of 1 to 10, a branched chain alkylene group having a carbon number of 2 to 10, or a divalent organic group represented by each formula of

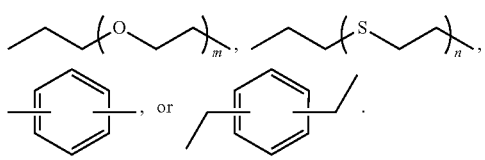

$R_{22}$ represents a divalent organic group represented by each formula of

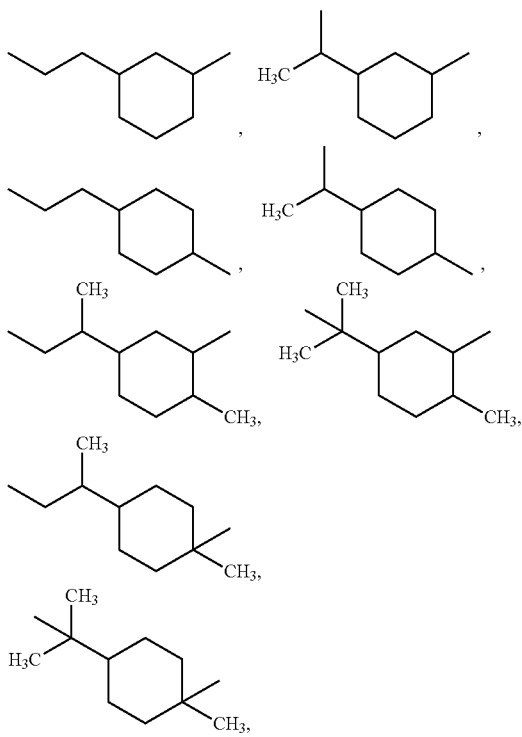

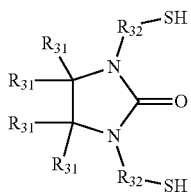

$m$ is an integer of 1 to 5. $n$ is an integer of 1 to 5.

However, the formula (II) excludes the case where $R_{21}$'s are simultaneously

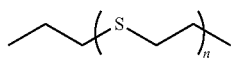

and $R_{22}$ is

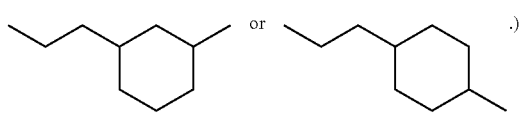

[Chem. 13]

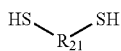
(3)

(In the formula (3), $R_{21}$ is the same as defined above.)

A fourth invention is a synthesis method of a thiol compound represented by the chemical formula (III) or chemical formula (IV), containing reacting a dialkene compound represented by the chemical formula (4) or chemical formula (5) with thioacetic acid or thiobenzoic acid.

[Chem. 14]

(III)

(In the formula (III), $R_{31}$'s are the same or different and represent a hydrogen atom, a straight chain alkyl group having a carbon number of 1 to 10, a branched chain alkyl group having a carbon number of 3 to 10, or an aryl group. $R_{32}$'s are the same or different and represent a straight chain alkylene group having a carbon number of 2 to 12, a branched chain alkylene group having a carbon number of 3 to 12, or a divalent organic group represented by the following chemical formula (a) to chemical formula (c). However, the formula (III) excludes the case where $R_{31}$'s are simultaneously a hydrogen atom and $R_{32}$'s are simultaneously an ethylene group.)

[Chem. 15]

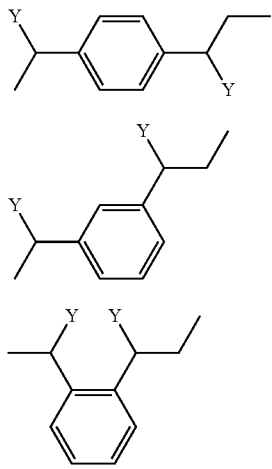

(a)

(b)

(c)

(In the formulae (a) to formula (c), Y's are the same or different and represent a hydrogen atom or a methyl group.)

[Chem. 16]

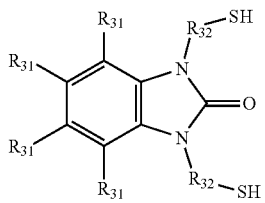

(IV)

(In the formula (IV), $R_{31}$'s and $R_{32}$'s are the same as defined above.)

[Chem. 17]

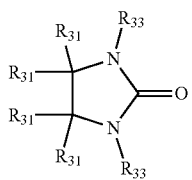

(4)

(In the formula (4), $R_{31}$'s are the same as defined above. $R_{33}$'s are the same or different and represent a straight chain alkenyl group having a carbon number of 2 to 12, a branched chain alkenyl group having a carbon number of 3 to 12, or an organic group represented by the following chemical formula (g) to chemical formula (i). However, the formula (4) excludes the case where $R_{31}$'s are simultaneously a hydrogen atom and $R_{33}$'s are simultaneously a vinyl group.)

[Chem. 18]

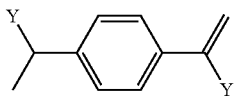

(g)

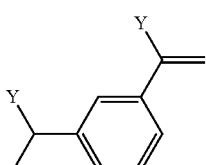

(h)

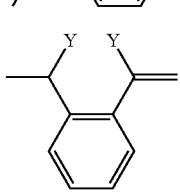

(i)

(In the formula (g) to formula (i), Y's are the same as defined above.)

[Chem. 19]

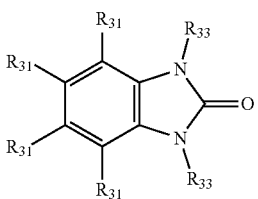

(5)

(In the formula (5), $R_{31}$'s and $R_{33}$'s are the same as defined above.)

A fifth invention is a synthesis method of a thiol compound represented by the chemical formula (V), chemical formula (VI) or chemical formula (VII), containing reacting a dialkene compound represented by the chemical formula (6), chemical formula (7) or chemical formula (8) with thioacetic acid or thiobenzoic acid.

[Chem. 20]

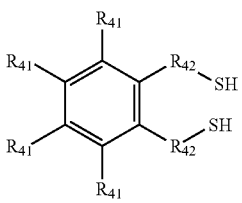

(V)

(In the formula (V), $R_{41}$'s are the same or different and represent a hydrogen atom, a straight chain alkyl group having a carbon number of 1 to 10, a branched chain alkyl group having a carbon number of 3 to 10, or an aryl group. $R_{42}$'s are the same or different and represent a divalent organic group. However, the formula (V) excludes the case where $R_{41}$'s are simultaneously a hydrogen atom and $R_{42}$'s are simultaneously a methylene group or an ethylene group.)

[Chem. 21]

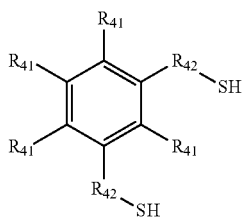

(VI)

(In the formula (VI), $R_{41}$'s and $R_{42}$'s are the same as defined above. However, the formula (VI) excludes the case where $R_{41}$'s are simultaneously a hydrogen atom and $R_{42}$'s are simultaneously a methylene group or an ethylene group.)

[Chem. 22]

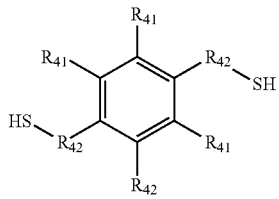

(VII)

(In the formula (VII), $R_{41}$'s and $R_{42}$'s are the same as defined above. However, the formula (VII) excludes the case where $R_{41}$'s are simultaneously a hydrogen atom and $R_{42}$'s are simultaneously a methylene group, an ethylene group or a trimethylene group.)

[Chem. 23]

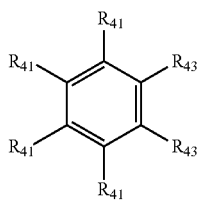

(6)

(In the formula (6), $R_{41}$'s are the same as defined above. $R_{43}$'s are the same or different and represent an organic group having a double bond. However, the formula (6) excludes the case where $R_{41}$'s are simultaneously a hydrogen atom and $R_{43}$'s are simultaneously a vinyl group.)

[Chem. 24]

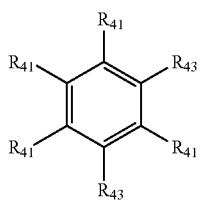

(7)

(In the formula (7), $R_{41}$'s and $R_{43}$'s are the same as defined above. However, the formula (7) excludes the case where $R_{41}$'s are simultaneously a hydrogen atom and $R_{43}$'s are simultaneously a vinyl group.)

[Chem. 25]

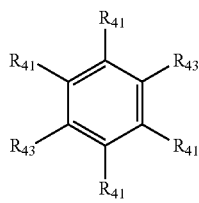

(8)

(In the formula (8), $R_{41}$'s and $R_{43}$'s are the same as defined above. However, the formula (8) excludes the case where $R_{41}$'s are simultaneously a hydrogen atom and $R_{43}$'s are simultaneously a vinyl group or an allyl group.)

A sixth invention is a curing agent containing the thiol compound of the first invention.

A seventh invention is a resin composition containing the thiol compound of the first invention and an epoxy compound (hereinafter sometimes referred to as a "first resin composition").

An eighth invention is the resin composition of the seventh invention, containing an amine as a curing accelerator.

A ninth invention is the resin composition of the seventh invention, containing a reaction product between an epoxy compound and an amine, as a curing accelerator.

A tenth invention is the resin composition of the seventh invention, containing a reaction product between a compound having one or more isocyanate group in the molecule and a compound having at least one of a primary amino group and a secondary amino group in the molecule, as a curing accelerator.

An eleventh invention is a resin composition containing the thiol compound of the first invention and an enic compound having a carbon-carbon double bond in the molecule (hereinafter sometimes referred to as a "second resin composition").

A twelfth invention is an adhesive containing any one of the resin compositions of the seventh invention to eleventh invention as a component.

A thirteenth invention is a sealant containing any one of the resin compositions of the seventh invention to eleventh invention as a component.

Advantageous Effects of Invention

The thiol compound of the present invention is a new compound having two or more thioether bonds in the molecule, a new compound having an imidazolidinone ring or a benzimidazolone ring or a new compound having a benzene ring. The thiol compound is expected to be useful as an intermediate raw material of various sulfur-containing compounds or a curing agent of resins. Furthermore, the thiol compound of the present invention is expected to have low volatility and is expected to have excellent compatibility with an epoxy compound, an enic compound and the like (to be low crystalline).

The thiol compound of the present invention has no ester bond in the molecule and therefore when used as a raw material of a resin, is expected to give a cured product having excellent hydrolysis resistance as compared with the case of using a conventional polythiol compound. Additionally, the thiol compound of the present invention is expected to give a cured product having low elasticity.

Furthermore, the adhesive and sealant of the present invention is expected to have excellent moisture resistance and the like.

DESCRIPTION OF EMBODIMENTS

Figure 1:
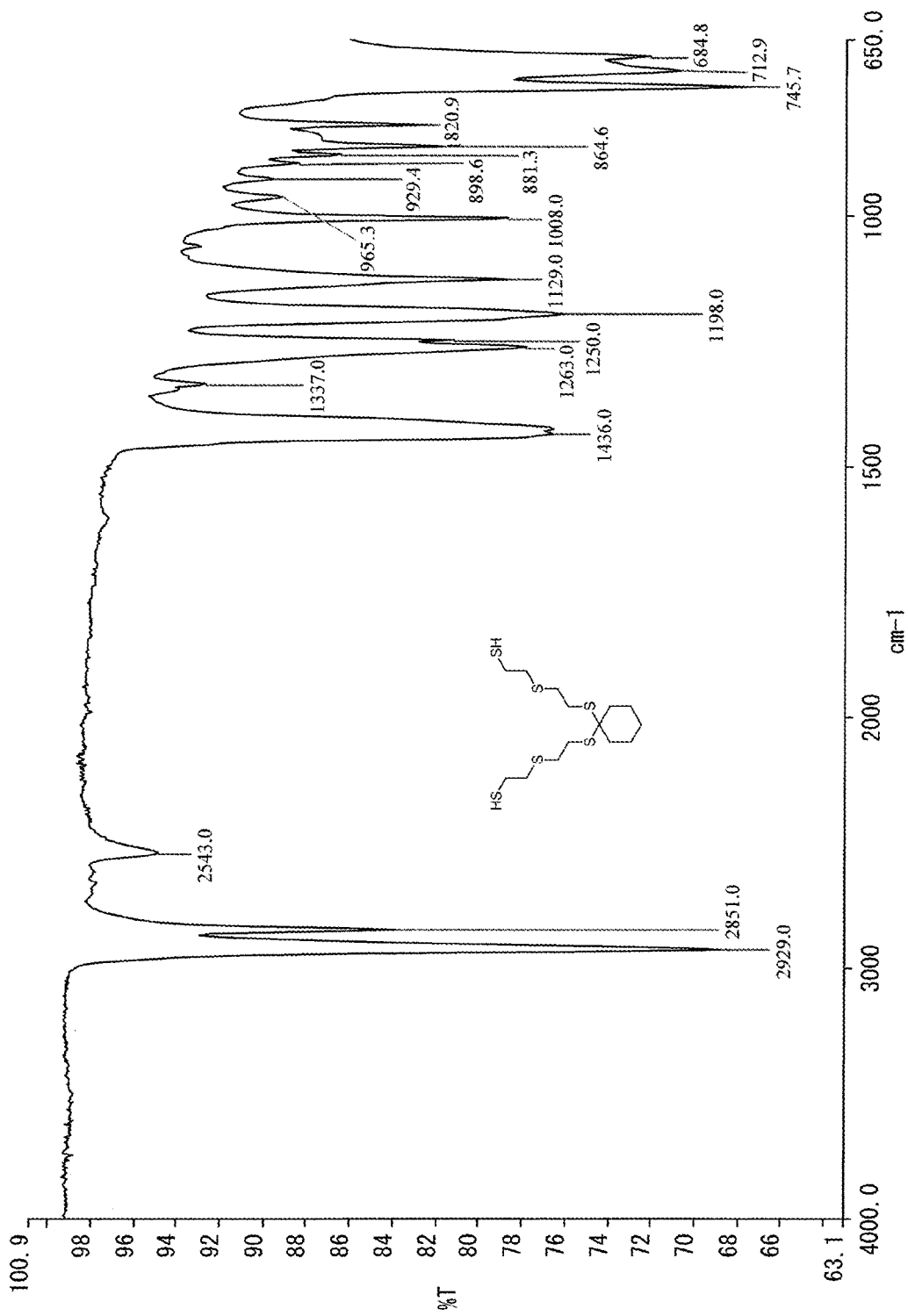
FIG. 1 is an IR spectral chart of a pale yellow liquid obtained in Example 1-1.

The thiol compound of the present invention is a thiol compound represented by any one of the following chemical formula (I) to chemical formula (VII).

The thiol compounds of the present invention are described below in the order of a thiol compound represented by the chemical formula (I) (first embodiment), a thiol compound represented by the chemical formula (II) (second embodiment), a thiol compound represented by the chemical formula (III) or chemical formula (IV) (third embodiment), and a thiol compound represented by the chemical formula (V), chemical formula (VI) or chemical formula (VII) (fourth embodiment).

First Embodiment

The thiol compound of the first embodiment is a reaction product between a certain carbonyl compound and a thiol compound and is represented by the following chemical formula (I).

[Chem. 26]

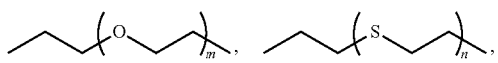

(I)

(In the formula (I), $R_1$'s are the same or different and represent a straight chain alkylene group having a carbon number of 1 to 10, a branched chain alkylene group having a carbon number of 2 to 10, or a divalent organic group represented by each formula of

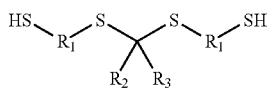

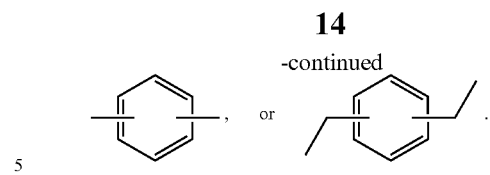

$R_2$ and $R_3$ are the same or different and represent a hydrogen atom, a straight chain alkyl group having a carbon number of 1 to 10, a branched chain alkyl group having a carbon number of 3 to 10, or an aryl group, and $R_2$ and $R_3$ may be linked to form a ring. m is an integer of 1 to 5. n is an integer of 1 to 5.

However, the formula (I) excludes (1) the case where $R_2$ and $R_3$ are simultaneously a hydrogen atom and (2) the case where $R_1$'s are simultaneously

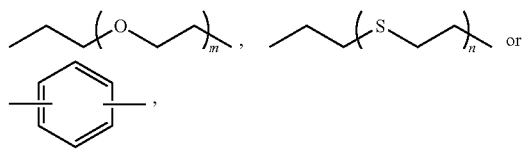

$R_2$ is a methyl group and $R_3$ is a methyl group or an ethyl group.)

The thiol compound represented by the chemical formula (I) includes a thiol compound represented by the chemical formula (I-1) and a thiol compound represented by the chemical formula (I-2).

[Chem. 27]

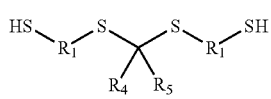

(I-1)

(In the formula (I-1), $R_1$'s are the same as defined above. $R_4$ and $R_5$ are the same or different and represent a hydrogen atom, a straight chain alkyl group having a carbon number of 1 to 10, a branched chain alkyl group having a carbon number of 3 to 10, or an aryl group.

However, the formula (I-1) excludes (1) the case where $R_4$ and $R_5$ are simultaneously a hydrogen atom and (2) the case where $R_1$'s are simultaneously

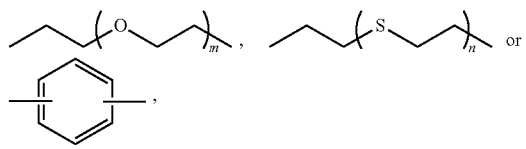

$R_4$ is a methyl group and $R_5$ is a methyl group or an ethyl group.)

[Chem. 28]

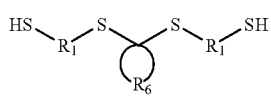

(I-2)

(In the formula (I-2), $R_1$'s are the same as defined above. $R_6$ represents

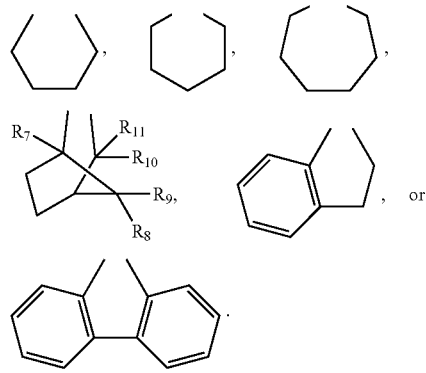

$R_7$, $R_8$, $R_9$, $R_{10}$, and $R_{11}$ are the same or different and represent a hydrogen atom or a methyl group.)

Examples of the thiol compound represented by the chemical formula (I-1) include thiol compounds represented by the chemical formula (I-1-1) to chemical formula (I-1-12).

Examples of the thiol compound represented by the chemical formula (I-2) include thiol compounds represented by the chemical formula (I-2-1) to chemical formula (I-2-17).

[Chem. 29]

(I-1-1)

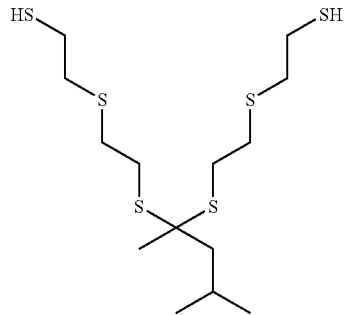

(I-1-2)

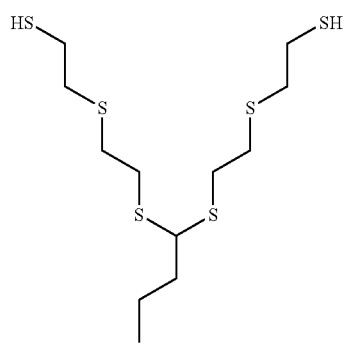

(I-1-3)

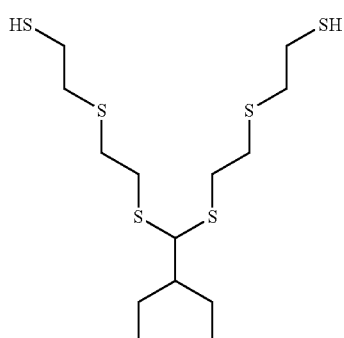

(I-1-4)

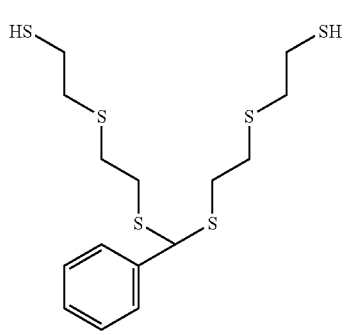

(I-1-5)

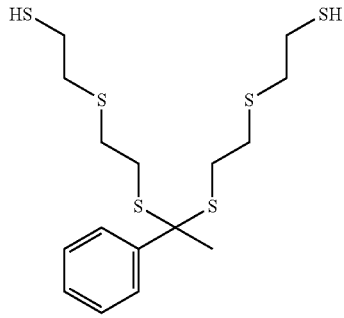

(I-1-6)

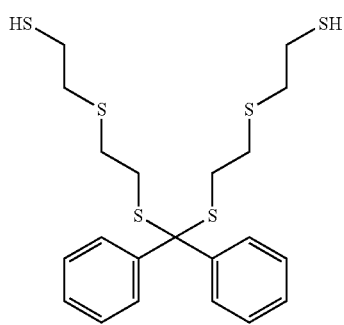

(I-1-7)

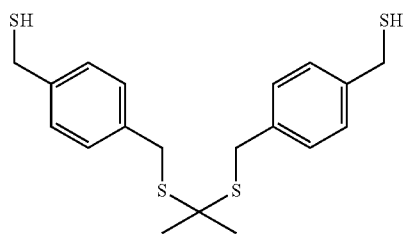

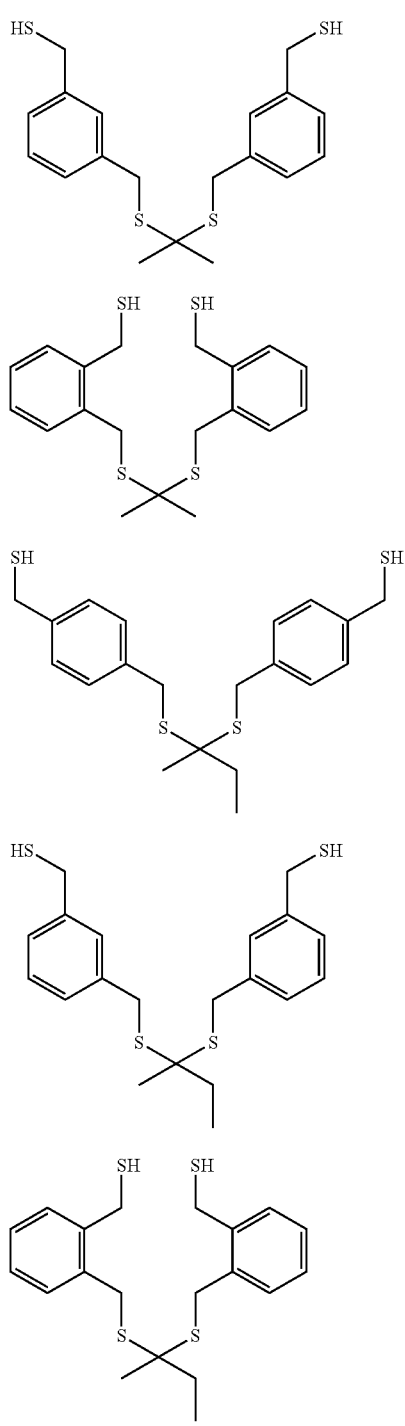
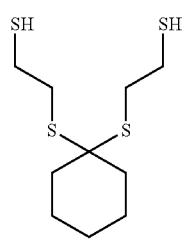
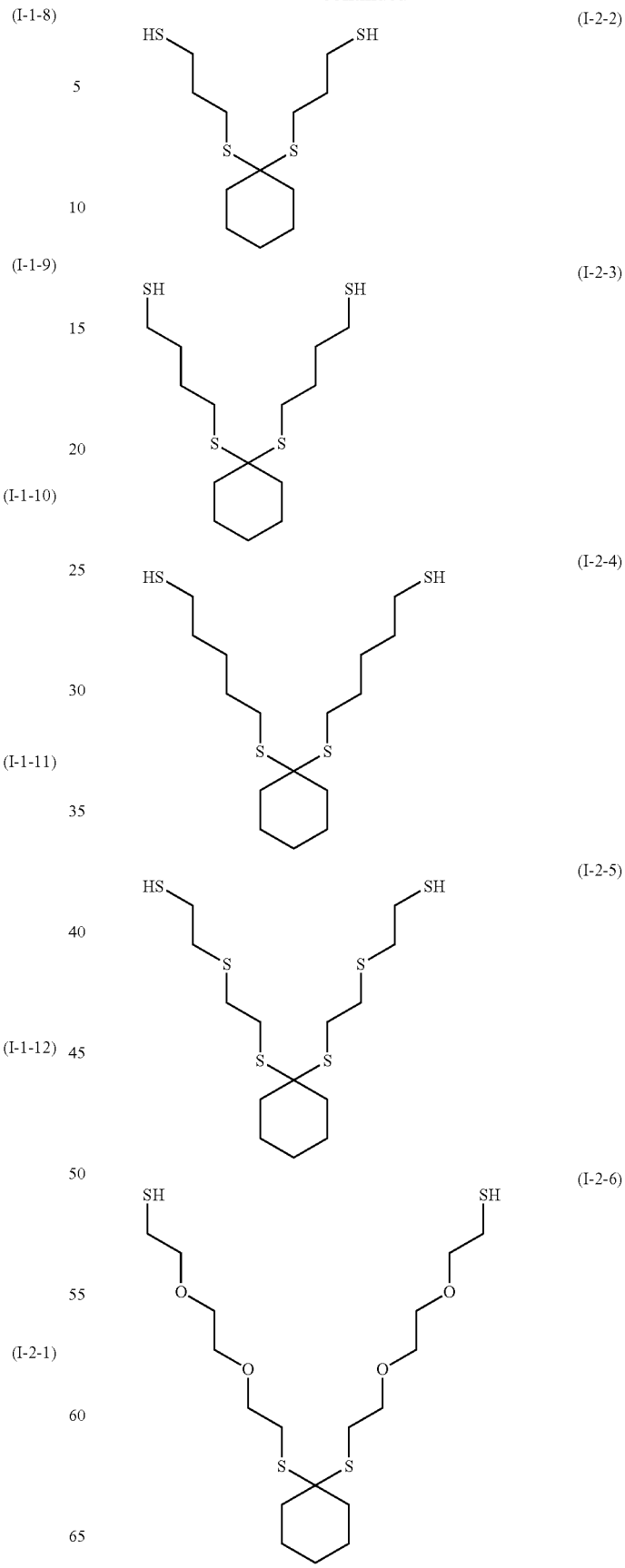

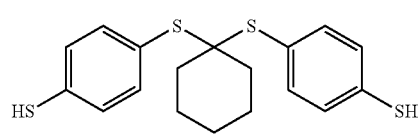
(I-2-7)
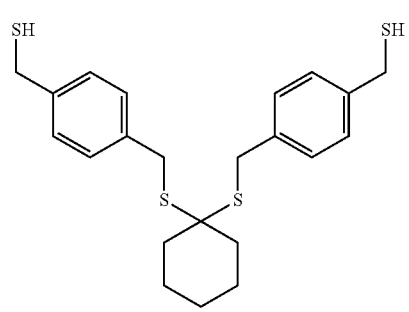
(I-2-8)
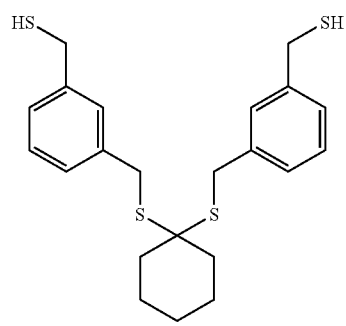
(I-2-9)
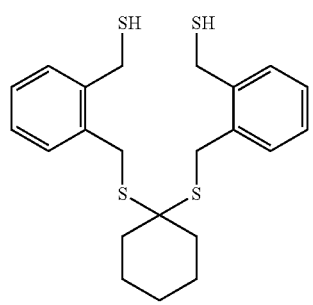
(I-2-10)
[Chem. 31]
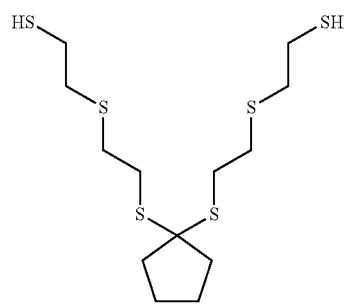
(I-2-11)
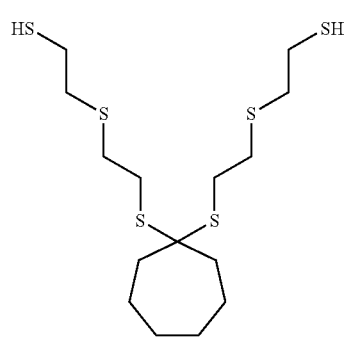
(I-2-12)
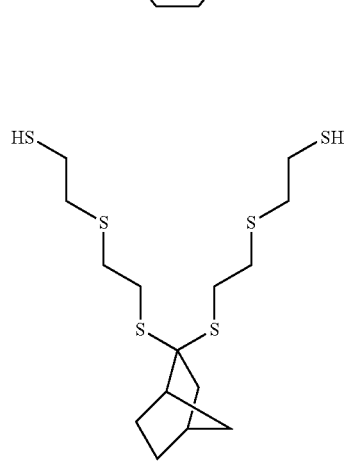
(I-2-13)
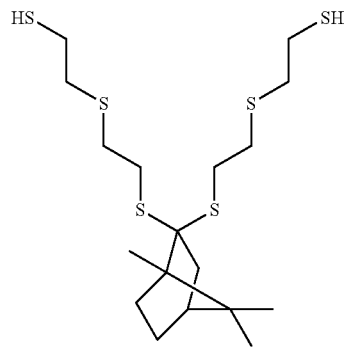
(I-2-14)
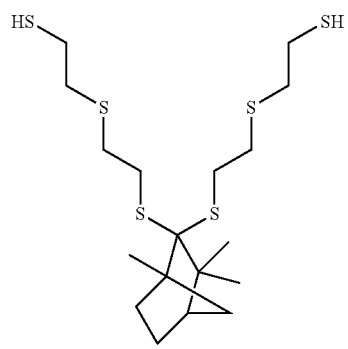
(I-2-15)

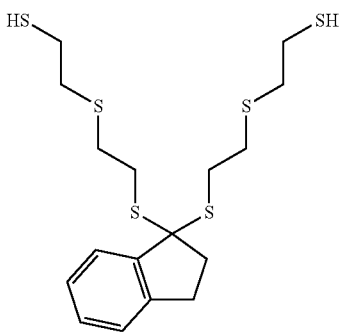

(I-2-16)

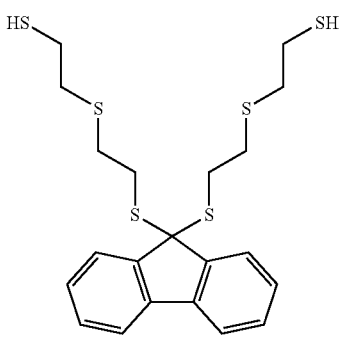

(I-2-17)

In the first embodiment, $R_2$ and $R_3$ in the chemical formula (I) are, as described above, the same or different and represent a hydrogen atom, a straight chain alkyl group having a carbon number of 1 to 10, a branched chain alkyl group having a carbon number of 3 to 10, or an aryl group, and $R_2$ and $R_3$ may be linked to form a ring. The thiol compound of the first embodiment is preferably compounds in which $R_2$ and $R_3$ are linked to form a ring (i.e., the thiol compound represented by the chemical formula (I-2)) and compounds in which at least one of $R_2$ and $R_3$ is a phenyl group. The thiol compound represented by the chemical formula (I-2) is more preferably compounds having a cyclohexane ring in the molecule (e.g., compounds represented by the chemical formula (I-2-1) to chemical formula (I-2-10)).

In the first embodiment, examples of the aryl group include phenyl group, 2-tolyl group, 3-tolyl group, 4-tolyl group, 2,3-xylyl group, 2,4-xylyl group, 2,5-xylyl group, 2,6-xylyl group, 3,4-xylyl group, 3,5-xylyl group, 2,4,6-trimethylphenyl group, 2,3,5-trimethylphenyl group, 2,3,6-trimethylphenyl group, 2,4,5-trimethylphenyl group, 2,3,5,6-tetramethylphenyl group, 1-naphthyl group, 2-naphthyl group, and the like.

The thiol compound of the first embodiment can be synthesized by reacting a carbonyl compound represented by the chemical formula (1) with a thiol compound represented by the chemical formula (2) (see reaction scheme (A)).

In carrying out the synthesis reaction, an acid catalyst (A) may be used in order to accelerate the reaction. Furthermore, a reaction solvent (B) may be used in order to smoothly proceed the reaction.

Reaction scheme (A)

[Chem. 32]

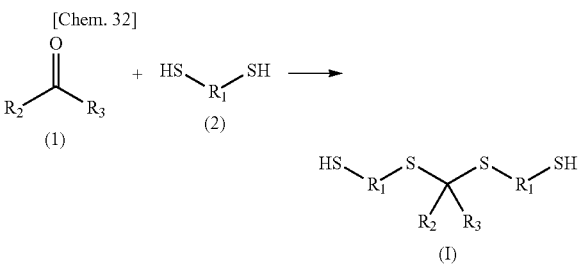

(In each formula in the reaction scheme (A), $R_1$, $R_2$ and $R_3$ are the same as defined above.

However, the formula (1) excludes the case where $R_2$ and $R_3$ are simultaneously the same, and the formula (I) excludes (1) the case where $R_2$ and $R_3$ are simultaneously a hydrogen atom and (2) the case where $R_1$'s are simultaneously

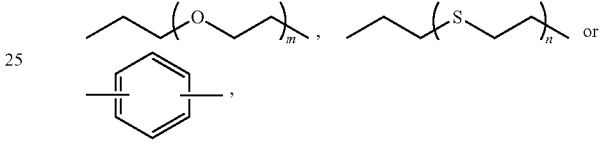

$R_2$ is a methyl group and $R_3$ is a methyl group or an ethyl group.)

The carbonyl compound represented by the chemical formula (1) includes a carbonyl compound represented by the chemical formula (1-1) and a carbonyl compound represented by the chemical formula (1-2).

[Chem. 33]

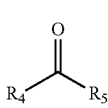

(1-1)

(In the formula (1-1), $R_4$ and $R_5$ are the same as defined above. However, the formula (1-1) excludes the case where $R_4$ and $R_5$ are simultaneously a hydrogen atom.)

[Chem. 34]

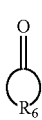

(1-2)

(In the formula (1-2), $R_6$ is the same as defined above.)

Examples of the carbonyl compound represented by the chemical formula (1-1) include carbonyl compounds represented by the chemical formula (1-1-1) to chemical formula (1-1-8).

Examples of the carbonyl compound represented by the chemical formula (1-2) include carbonyl compounds represented by the chemical formula (1-2-1) to chemical formula (1-2-8).

[Chem. 35]
(1-1-1) 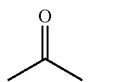
(1-1-2) 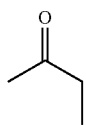
(1-1-3) 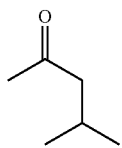
(1-1-4) 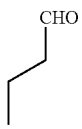
(1-1-5) 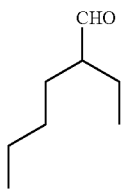
(1-1-6) 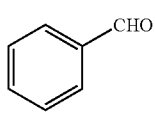
(1-1-7) 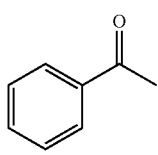
(1-1-8) 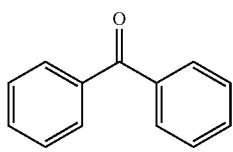
[Chem. 36]
(1-2-1) 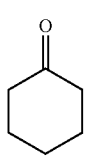
(1-2-2) 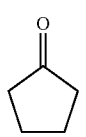
(1-2-3) 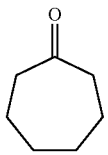
(1-2-4) 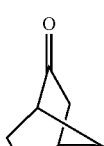
(1-2-5) 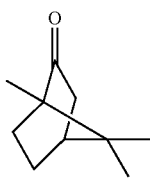
(1-2-6) 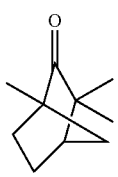
(1-2-7) 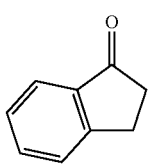
(1-2-8) 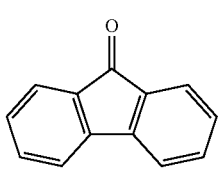
Examples of the thiol compound represented by the chemical formula (2) include thiol compounds represented by the chemical formula (2-1) to chemical formula (2-10). In the case where those thiol compounds are used in combination, thiol compounds in which $R_1$'s in the chemical formula (I) are different to each other can be synthesized.
[Chem. 37]
(2-1) 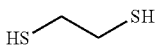
(2-2) 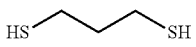
(2-3) 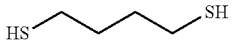
(2-4) 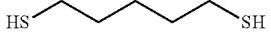
(2-5) 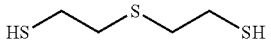

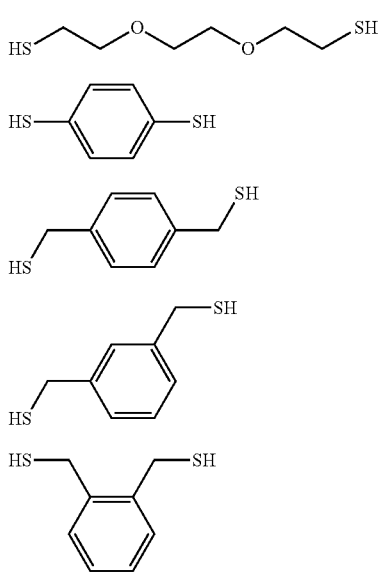

(2-6)
(2-7)
(2-8)
(2-9)
(2-10)

The amount used (amount charged) of the thiol compound represented by the chemical formula (2) is preferably an appropriate ratio in a range of 2 to 100 molar times the amount used (amount charged) of the carbonyl compound.

Examples of the acid catalyst (A) include hydrogen fluoride (hydrofluoric acid), hydrogen chloride (hydrochloric acid), hydrogen bromide (hydrobromic acid), hydrogen iodide (hydroiodic acid), carbonic acid, formic acid, acetic acid, benzoic acid, oxalic acid, citric acid, phosphoric acid, hexafluorophosphoric acid, nitric acid, sulfuric acid, methanesulfonic acid, toluenesulfonic acid, trifluoromethanesulfonic acid, boric acid, boron trifluoride, tetrafluoroboric acid, and the like. Those may be used in combination.

The amount used (amount charged) of the acid catalyst (A) is preferably an appropriate ratio in a range of 0.001 to 10 molar times the amount used (amount charged) of the carbonyl compound.

Examples of the reaction solvent (B) include solvents such as water, methanol, ethanol, propanol, 2-propanol, butanol, ethyl acetate, propyl acetate, butyl acetate, tetrahydrofuran, dioxane, acetonitrile, benzene, toluene, xylene, dichloromethane, chloroform, carbon tetrachloride, dimethylformamide, dimethylacetamide, dimethylsulfoxide, and hexamethylphosphoric triamide. Those may be used in combination as the reaction solvent (B).

The reaction temperature of the synthesis reaction is preferably set to be in a range of 0 to 200° C. The reaction time is appropriately set according to the reaction temperature set, but is preferably set to be in a range of 1 to 72 hours.

After completion of the synthesis reaction, the objective thiol compound of the first embodiment can be extracted from the reaction liquid (reaction mixture) obtained by, for example, the means such as concentration of the reaction liquid by distillation of the reaction solvent or a solvent extraction method.

As necessary, purification can be performed by utilizing the means such as cleaning with water or the like, treatment with activated carbon or silica gel chromatography.

Second Embodiment

The thiol compound of the second embodiment is a reaction product between a certain dialkene compound and a thiol compound and is represented by the following chemical formula (II).

[Chem. 38]

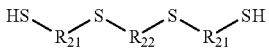

(II)

(In the formula (II), $R_{21}$'s are the same or different and represent a straight chain alkylene group having a carbon number of 1 to 10, a branched chain alkylene group having a carbon number of 2 to 10, or a divalent organic group represented by each formula of

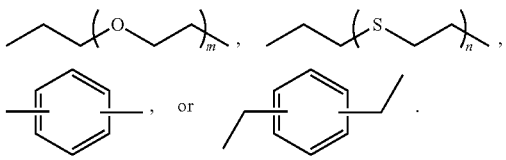

$R_{22}$ represents a divalent organic group represented by each formula of

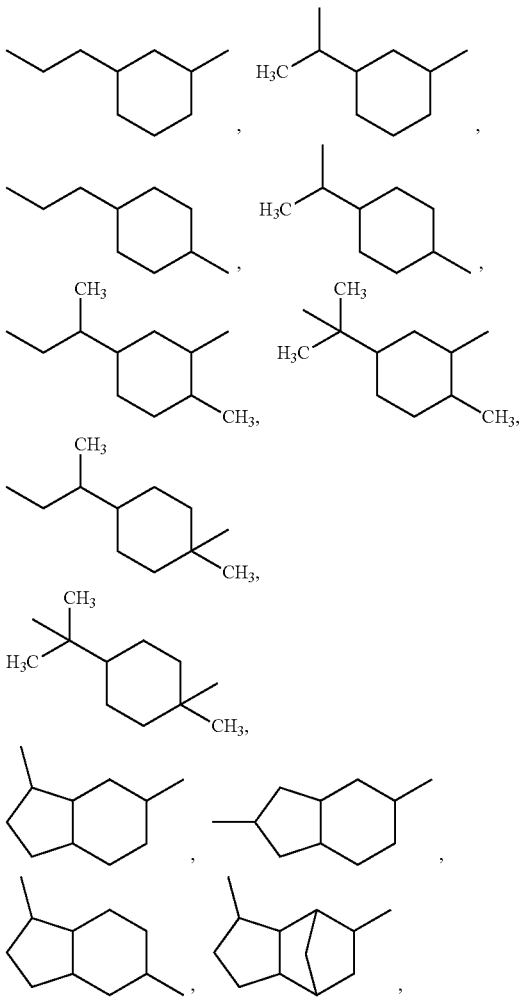

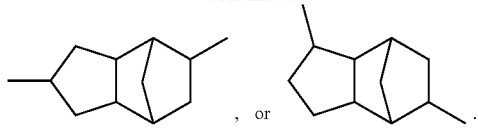

m is an integer of 1 to 5. n is an integer of 1 to 5.

However, the formula (II) excludes the case where $R_{21}$'s are simultaneously

and $R_{22}$ is

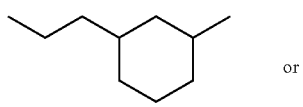

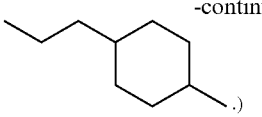

The thiol compound represented by the chemical formula (II) can be preferably synthesized by reacting a dialkene compound selected from vinylcyclohexene, limonene, tetrahydroindene, and dicyclopentadiene with a thiol compound represented by the chemical formula (3).

[Chem. 39]

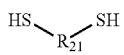

(3)

(In the formula (3), $R_{21}$ is the same as defined above.)

Examples of the thiol compound represented by the chemical formula (II) include thiol compounds represented by the chemical formula (II-1) to chemical formula (II-39).

[Chem. 40]

(II-1)
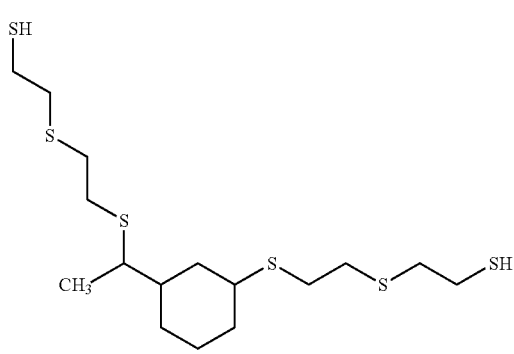

(II-2)
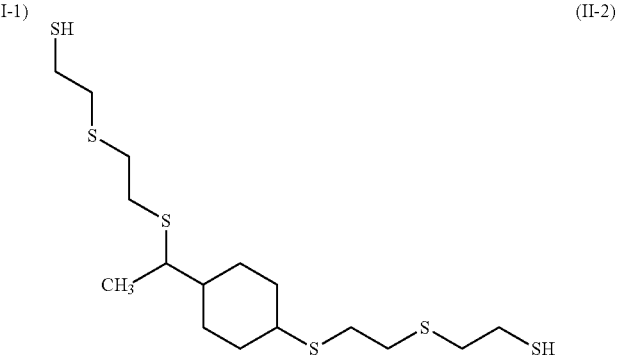

(II-3)
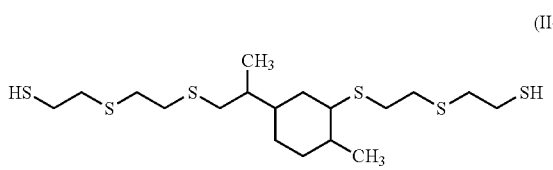

(II-4)
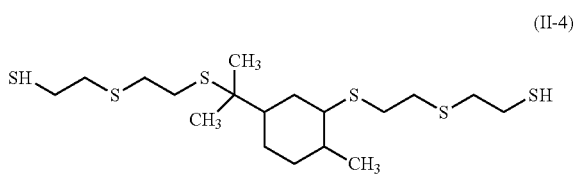

(II-5)
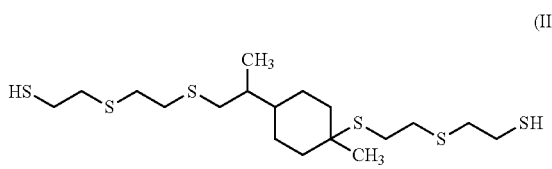

(II-6)
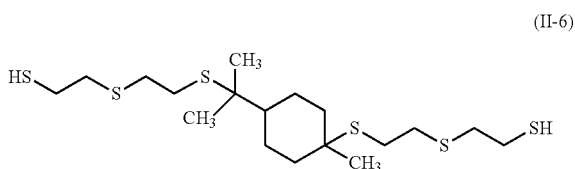

-continued
(II-7)
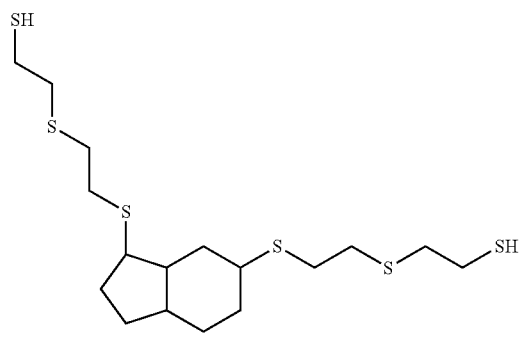
(II-8)
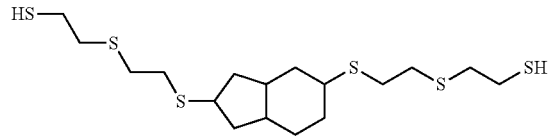
(II-9)
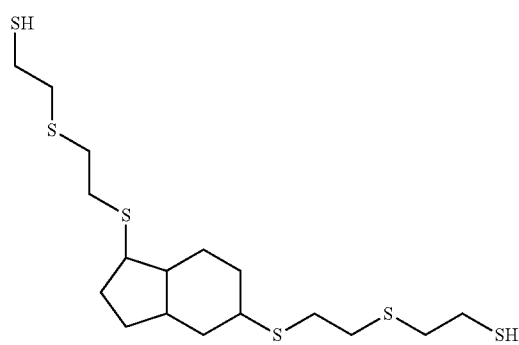
(II-10)
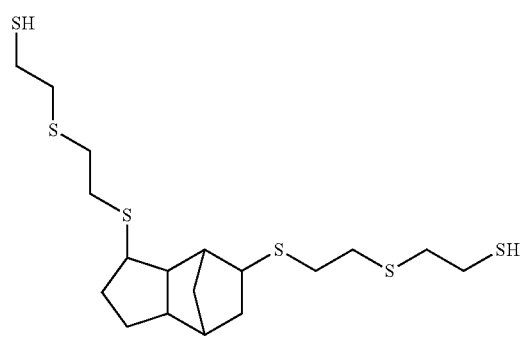
[Chem. 41]
(II-11)
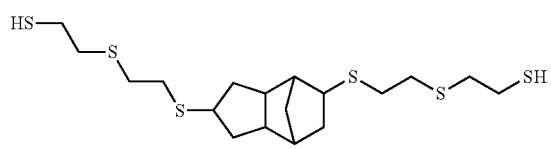
(II-12)
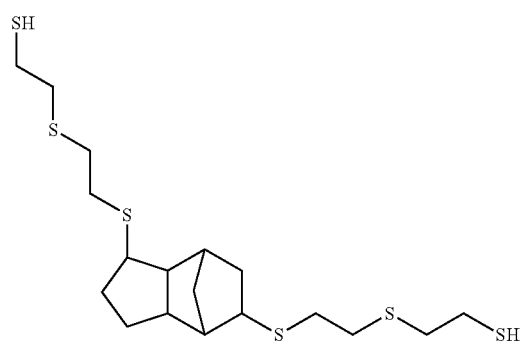
(II-13)
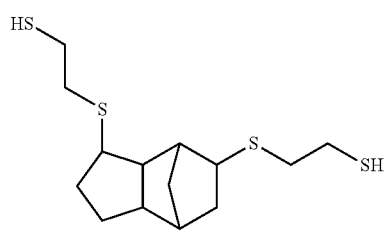
(II-14)
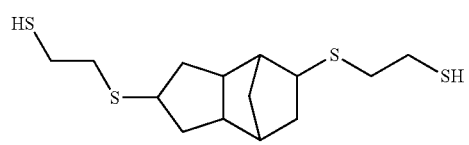
(II-15)
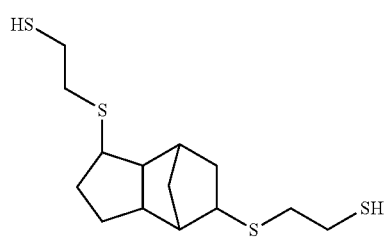
(II-16)
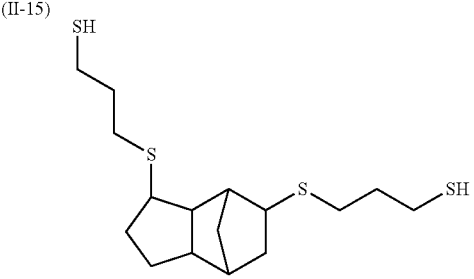

-continued
(II-17)
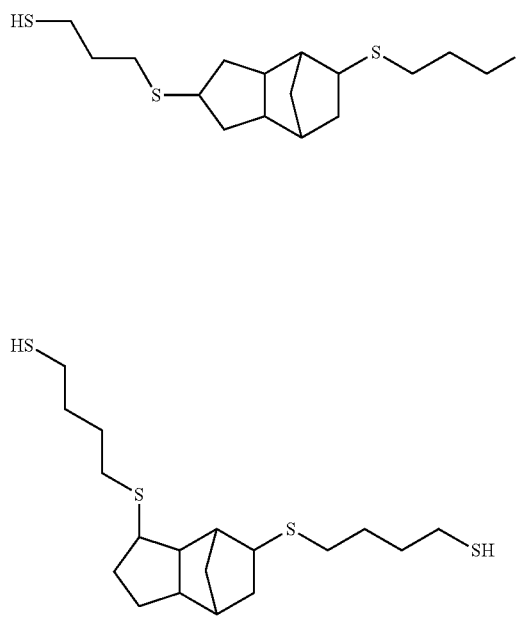
(II-18)
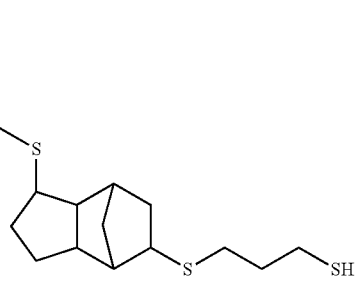
(II-19)
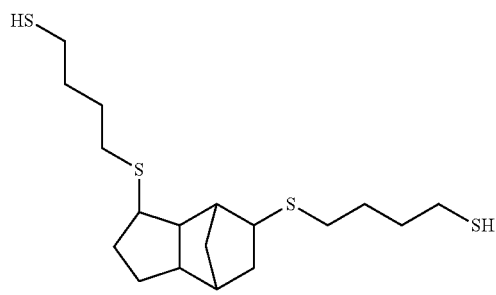
(II-20)
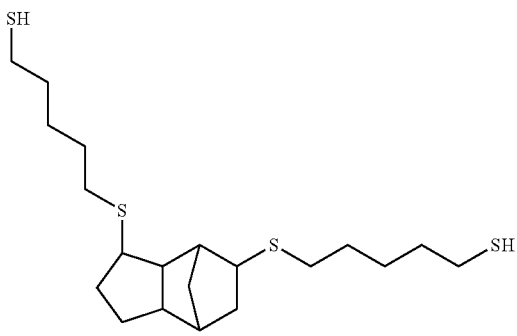
[Chem. 42]
(II-21)
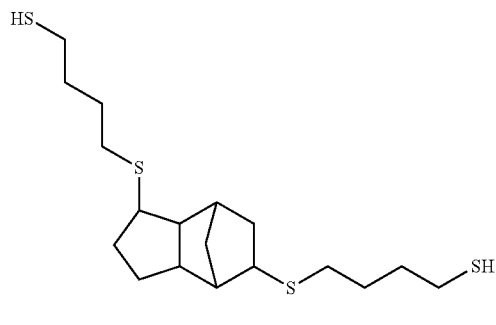
(II-22)
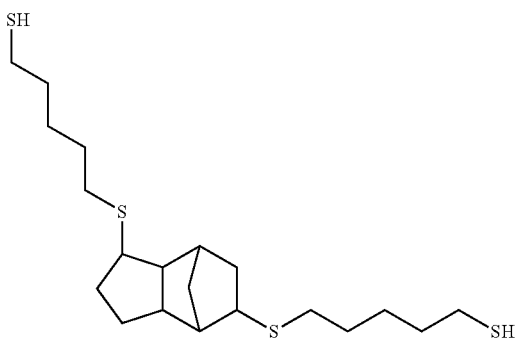
(II-23)
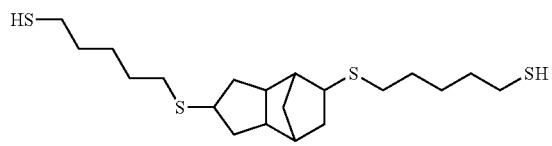
(II-24)

-continued
(II-25)
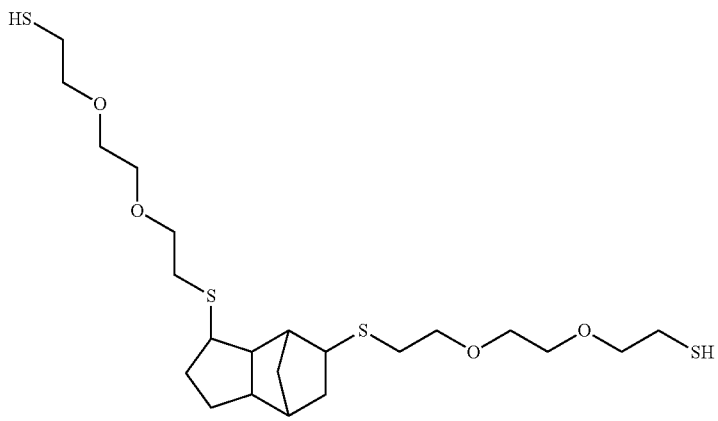
(II-26)
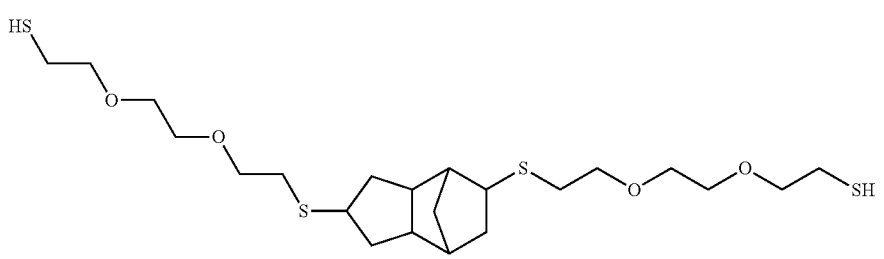
[Chem. 43]
(II-27)
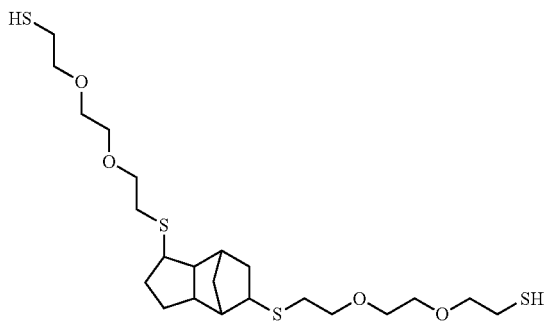
(II-28)
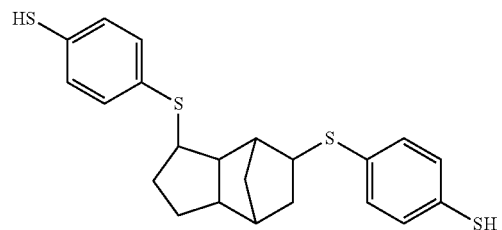
(II-29)
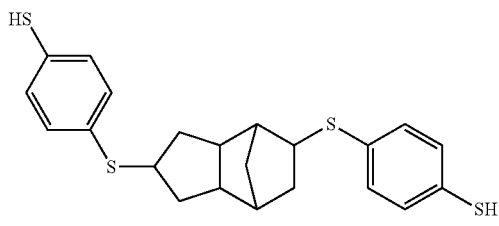
(II-30)
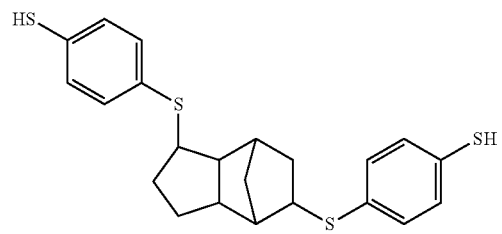

-continued
(II-31)
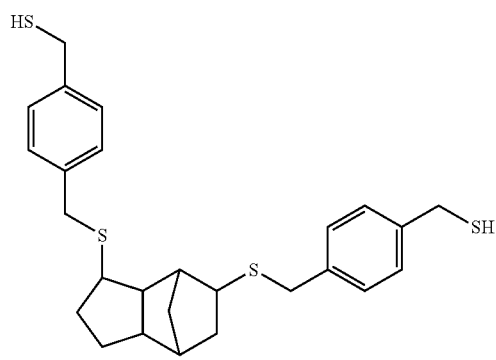
(II-32)
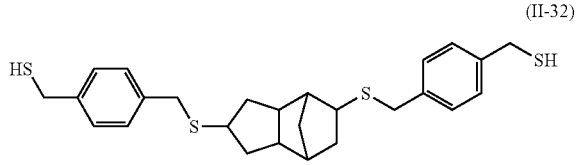
[Chem. 44]
(II-33)
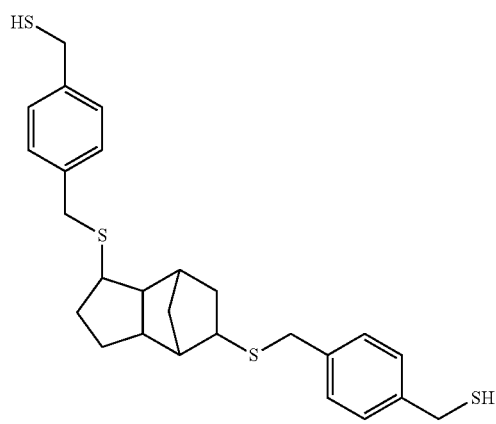
(II-34)
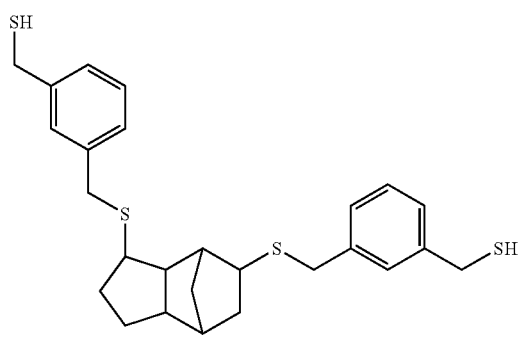
(II-35)
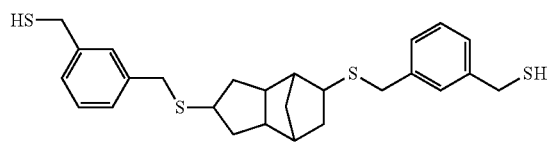
(II-36)
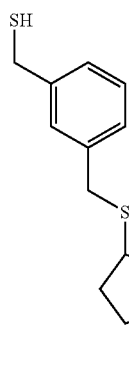
(II-37)
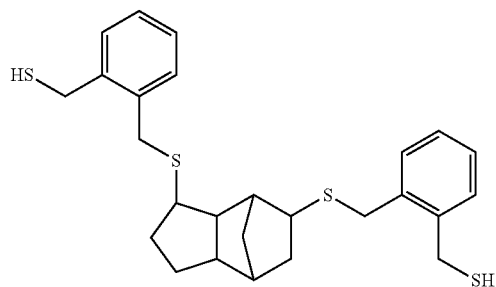
(II-38)
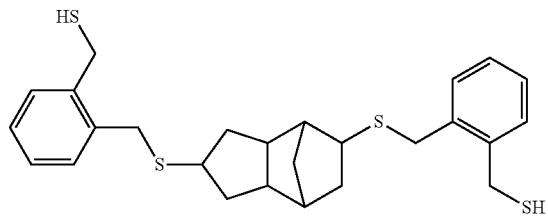

(II-39)

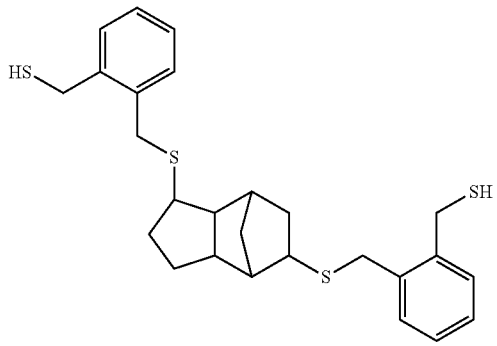

Examples of the thiol compound represented by the chemical formula (3) include thiol compounds represented by the chemical formula (3-1) to chemical formula (3-10). In the case where those thiol compounds are used in combination, the thiol compounds in which $R_{21}$'s in the chemical formula (II) are different to each other can be synthesized.

[Chem. 45]

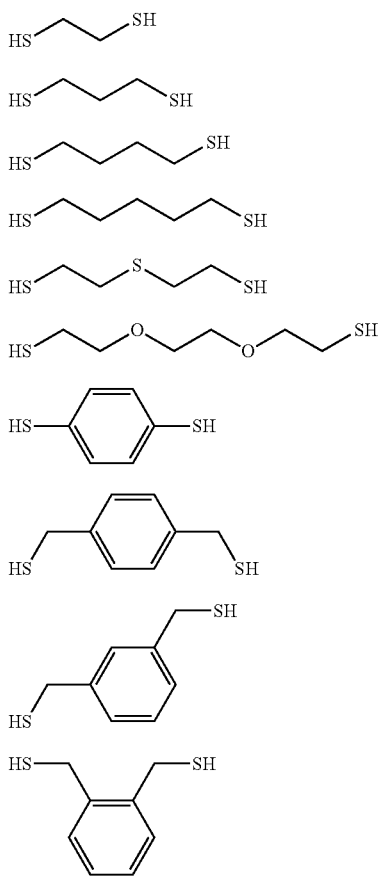

(3-1)
(3-2)
(3-3)
(3-4)
(3-5)
(3-6)
(3-7)
(3-8)
(3-9)
(3-10)

The amount used (amount charged) of the thiol compound represented by the chemical formula (3) is preferably an appropriate ratio in a range of 2 to 100 molar times the amount used (amount charged) of the dialkene compound.

In the synthesis reaction of the thiol compound of the second embodiment, a radical initiator (C) may be used in order to accelerate the reaction. Furthermore, a reaction solvent (B) may be used in order to smoothly proceed the reaction.

Examples of the radical initiator (C) include azobisisobutyronitrile, t-hexylperoxyisopropyl monocarbonate, t-hexylperoxy 2-ethylhexanoate, 1,1,3,3-tetramethylbutylperoxy 2-ethylhexanoate, t-butylperoxypivalate, t-hexylperoxypivalate, t-butylperoxyneodecanoate, t-hexylperoxyneodecanoate, 1,1,3,3-tetramethylbutylperoxyneodecanoate, 1,1-bis(t-hexylperoxy)cyclohexane, benzoyl peroxide, 3,5,5-trimethylhexanoyl peroxide, lauroyl peroxide, 2,2'-azobis(2-methylbutyronitrile), dimethyl 2,2'-azobis(2-methylpropionate), and the like.

The amount used (amount charged) of the radical initiator (C) is preferably an appropriate ratio in a range of 0.0001 to 10 molar times the amount used (amount charged) of the dialkene compound.

Examples of the reaction solvent (B) include solvents such as water, methanol, ethanol, propanol, 2-propanol, butanol, ethyl acetate, propyl acetate, butyl acetate, tetrahydrofuran, dioxane, acetonitrile, benzene, toluene, xylene, dichloromethane, chloroform, carbon tetrachloride, dimethylformamide, dimethylacetamide, dimethylsulfoxide, and hexamethylphosphoric triamide. Those may be used in combination as the reaction solvent (B).

The reaction temperature of the synthesis reaction is preferably set to be in a range of 0 to 200° C. The reaction time is appropriately set according to the reaction temperature set, but is preferably set to be in a range of 1 to 120 hours.

After completion of the synthesis reaction, the objective thiol compound of the second embodiment can be extracted from the reaction liquid (reaction mixture) obtained by, for example, the means such as concentration of the reaction liquid by distillation of the reaction solvent or a solvent extraction method.

As necessary, purification can be performed by utilizing the means such as cleaning with water or the like, treatment with activated carbon or silica gel chromatography.

Third Embodiment

The thiol compound of the third embodiment is a thiol compound obtained by reacting a certain dialkene compound with thioacetic acid or thiobenzoic acid and is represented by the following chemical formula (III) or chemical formula (IV).

[Chem. 46]

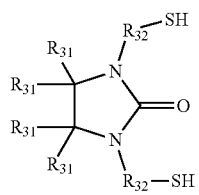
(III)

(In the formula (III), $R_{31}$'s are the same or different and represent a hydrogen atom, a straight chain alkyl group having a carbon number of 1 to 10, a branched chain alkyl group having a carbon number of 3 to 10, or an aryl group. $R_{32}$'s are the same or different and represent a straight chain alkylene group having a carbon number of 2 to 12, a branched chain alkylene group having a carbon number of 3 to 12, or a divalent organic group represented by the following chemical formula (a) to chemical formula (c). However, the formula (III) excludes the case where $R_{31}$'s are simultaneously a hydrogen atom and $R_{32}$'s are simultaneously an ethylene group (—$CH_2CH_2$—).)

[Chem. 47]

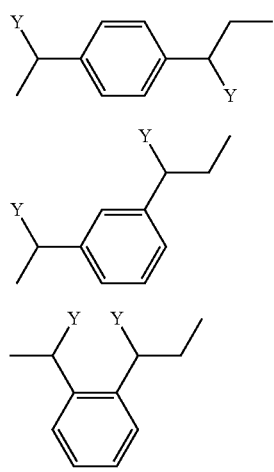

(a)

(b)

(c)

(In the formulae (a) to formula (c), Y's are the same or different and represent a hydrogen atom or a methyl group.)

[Chem. 48]

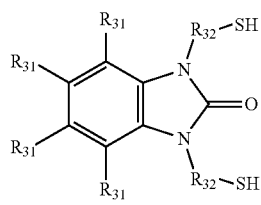
(IV)

(In the formula (IV), $R_{31}$'s and $R_{32}$'s are the same as defined above.)

Examples of the thiol compound represented by the chemical formula (III) include thiol compounds represented by the chemical formula (III-1) to chemical formula (III-12).

Examples of the thiol compound represented by the chemical formula (IV) include thiol compounds represented by the chemical formula (IV-1) to chemical formula (IV-12).

[Chem. 49]

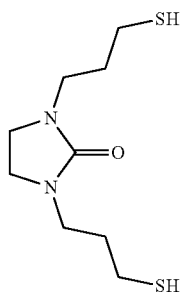
(III-1)

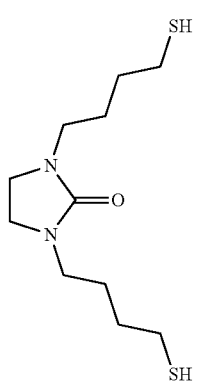
(III-2)

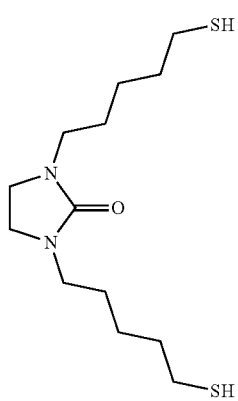
(III-3)

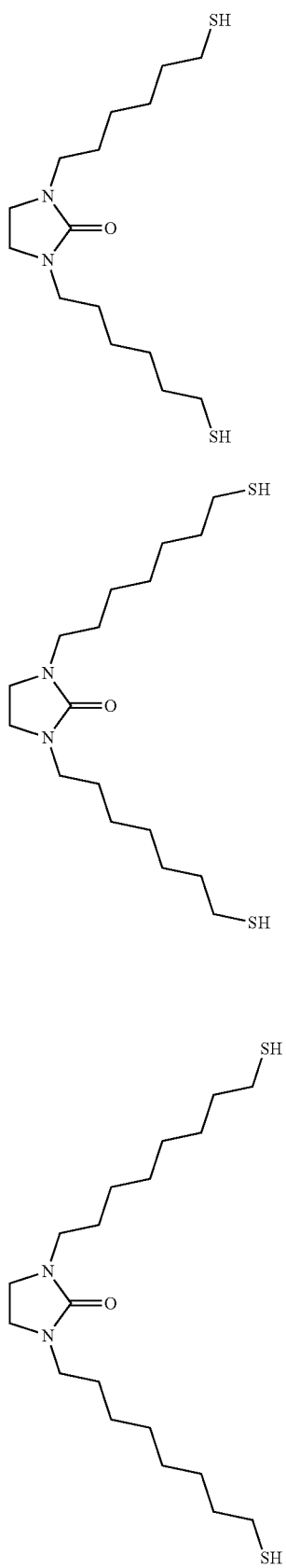
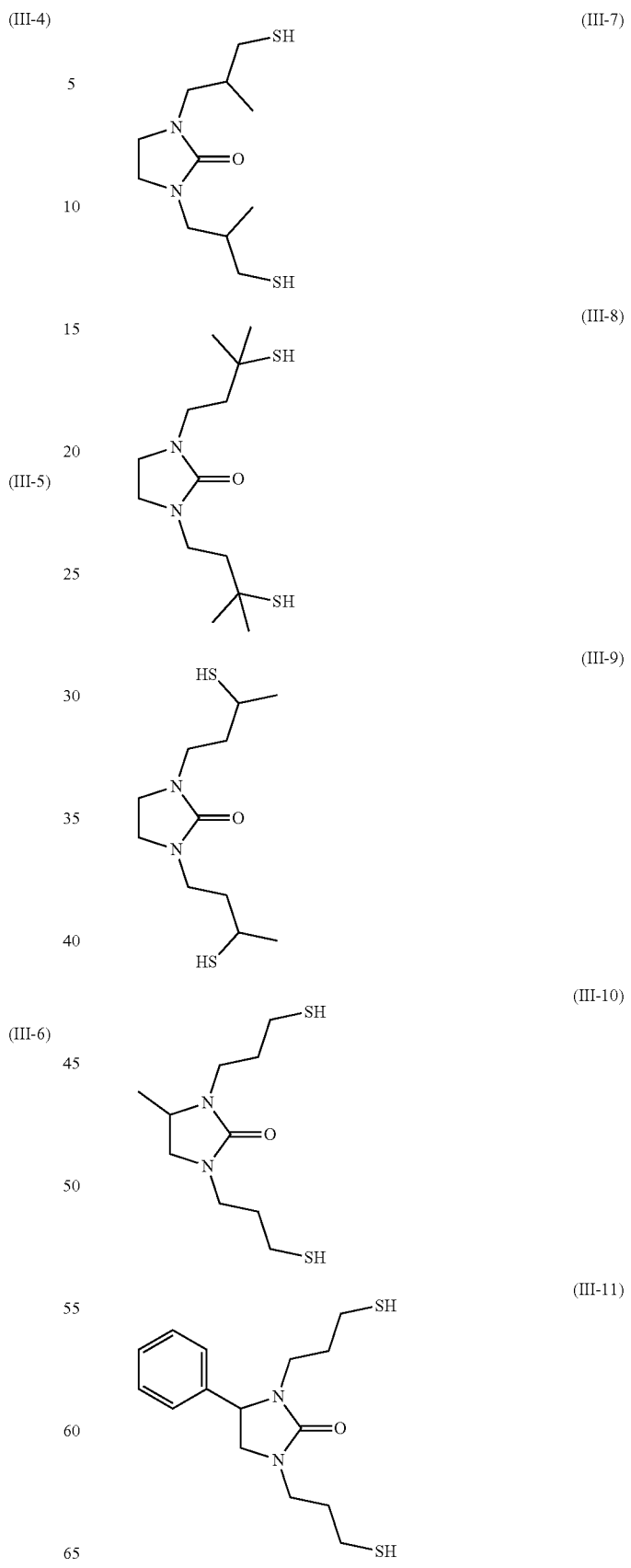

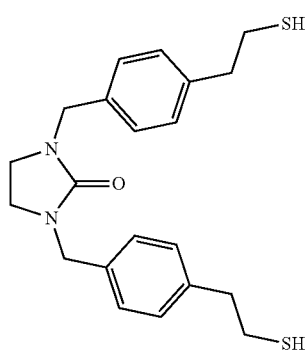
(III-12)
[Chem. 50]
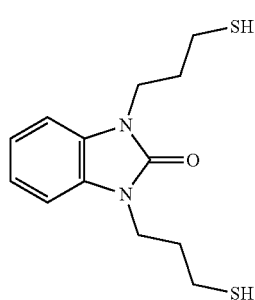
(IV-1)
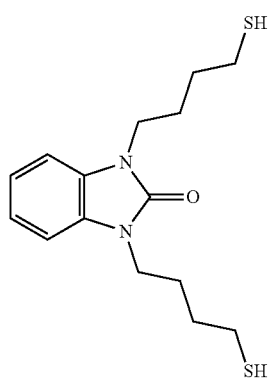
(IV-2)
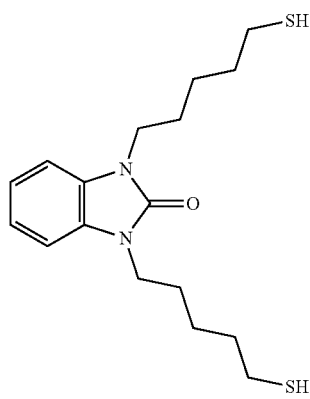
(IV-3)
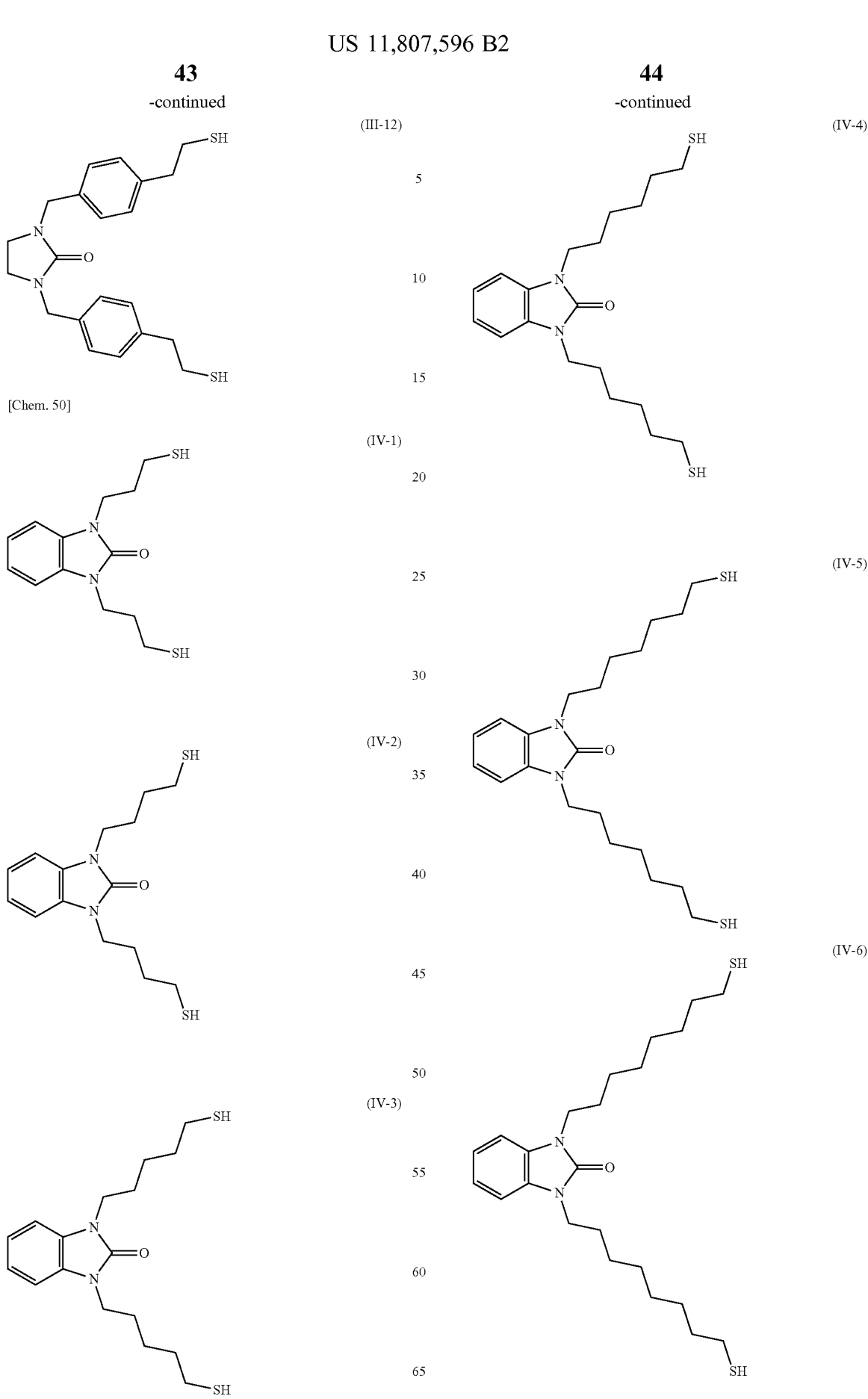

-continued (IV-7) 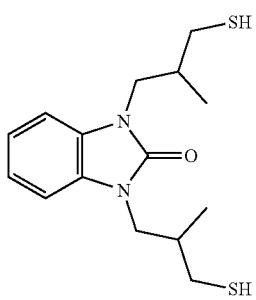

(IV-8) 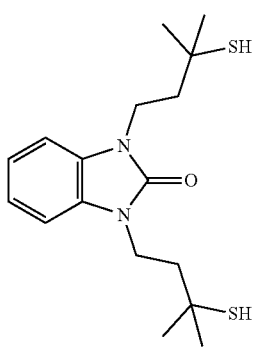

(IV-9) 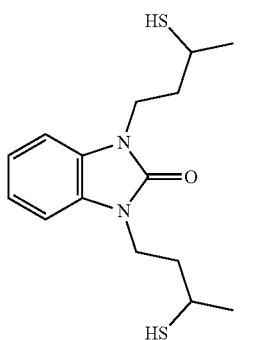

(IV-10) 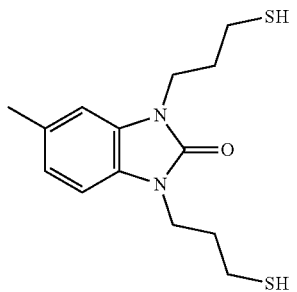

(IV-11) 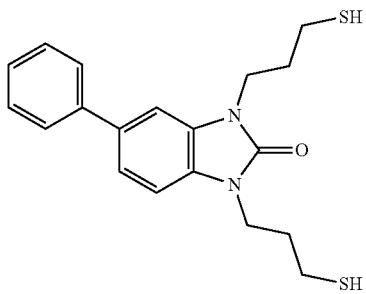

-continued (IV-12) 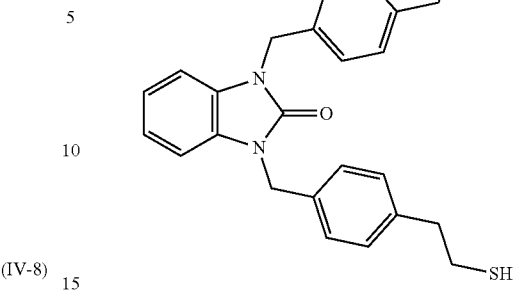

In the third embodiment, examples of the aryl group include phenyl group, 2-tolyl group, 3-tolyl group, 4-tolyl group, 2,3-xylyl group, 2,4-xylyl group, 2,5-xylyl group, 2,6-xylyl group, 3,4-xylyl group, 3,5-xylyl group, 2,4,6-trimethylphenyl group, 2,3,5-trimethylphenyl group, 2,3,6-trimethylphenyl group, 2,4,5-trimethylphenyl group, 2,3,5,6-tetramethylphenyl group, 1-naphthyl group, 2-naphthyl group, and the like.

The thiol compound of the third embodiment can be synthesized by reacting a dialkene compound represented by the chemical formula (4) or chemical formula (5) with thioacetic acid or thiobenzoic acid (first step), followed by a hydrolysis reaction or an alcoholysis reaction (alcoholysis) (second step) (see reaction scheme (B) described below). The dialkene compound represented by the chemical formula (4) is a raw material of the thiol compound represented by the chemical formula (III), and the dialkene compound represented by the chemical formula (5) is a raw material of the thiol compound represented by the chemical formula (IV).

[0051]

(4) 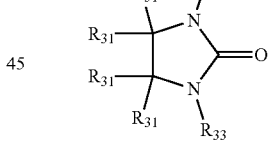

(In the formula (4), $R_{31}$'s are the same as defined above. $R_{33}$'s are the same or different and represent a straight chain alkenyl group having a carbon number of 2 to 12, a branched chain alkenyl group having a carbon number of 3 to 12, or an organic group represented by the following chemical formula (g) to chemical formula (i). However, the formula (4) excludes the case where $R_{31}$'s are simultaneously a hydrogen atom and $R_{33}$'s are simultaneously a vinyl group ($-CH=CH_2-$).)

[Chem. 52]

(g) 

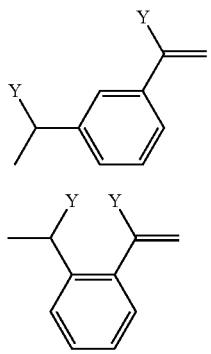

(h)

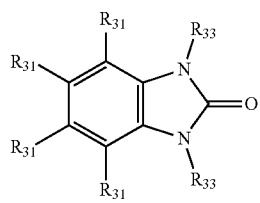

(i)

(In the formula (g) to formula (i), Y's are the same as defined above.)

[Chem. 53]

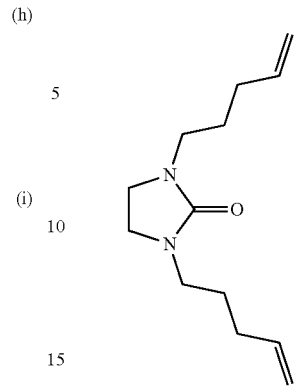

(5)

(In the formula (5), $R_{31}$'s and $R_{33}$'s are the same as defined above.)

Examples of the dialkene compound represented by the chemical formula (4) include dialkene compounds represented by the chemical formula (4-1) to chemical formula (4-12).

Examples of the dialkene compound represented by the chemical formula (5) include dialkene compounds represented by the chemical formula (5-1) to chemical formula (5-12).

[Chem. 54]

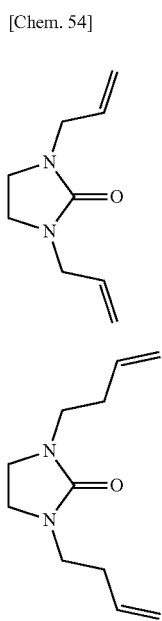

(4-1)

(4-2)

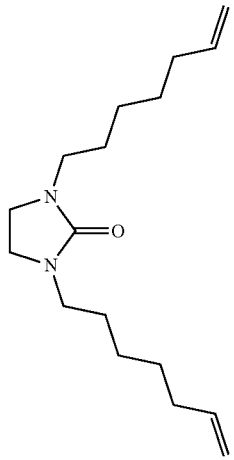

(4-3)

(4-4)

(4-5)

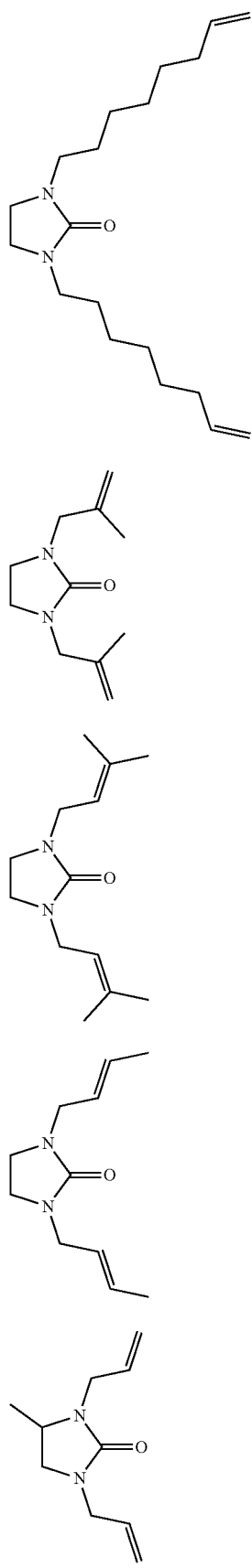
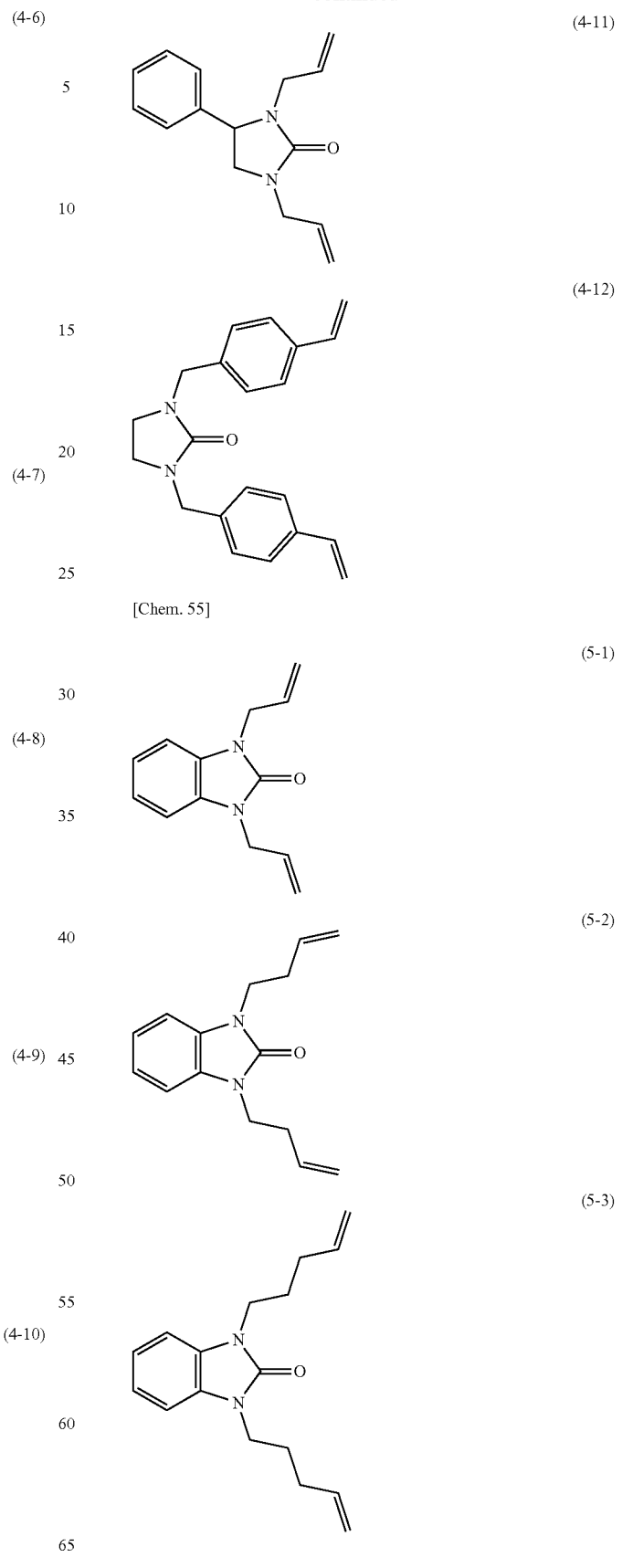

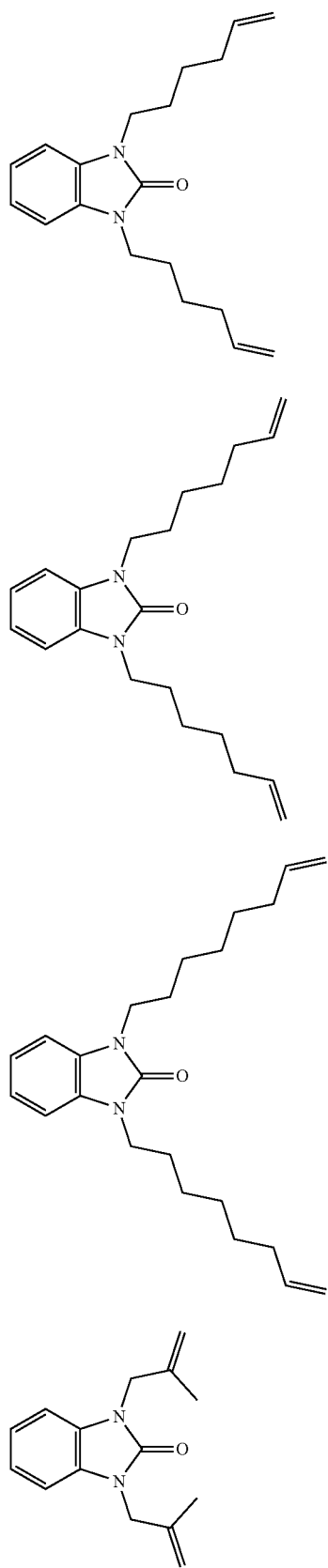
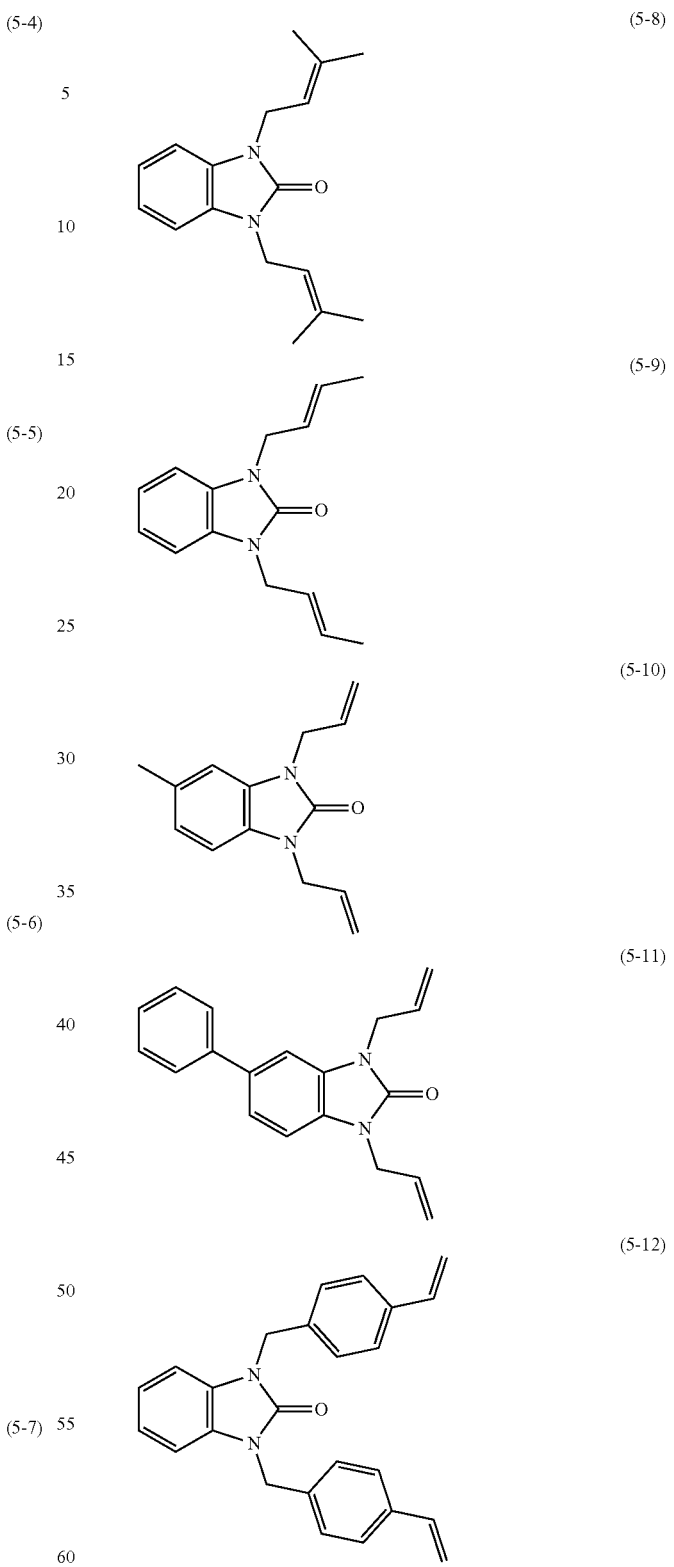
Those dialkene compounds can be synthesized by a conventional method. For example, the dialkene compound represented by the chemical formula (4) can be synthesized in accordance with the method described in WO2002/036662. The dialkene compound represented by the chemical formula (5) can be synthesized in accordance with the method described in J. Am. Chem. Soc., vol. 80, pp. 1657-1662 (1958).

In the first step, the amount used (amount charged) of thioacetic acid or thiobenzoic acid is preferably an appropriate ratio in a range of 2 to 40 molar times the amount used (amount charged) of the dialkene compound.

For example, an example that a thiol compound represented by the chemical formula (III-1) is synthesized by reacting a dialkene compound represented by a chemical formula (4-1) with thioacetic acid represented by the chemical formula (13) to obtain a thioacetic acid ester compound represented by the chemical formula (14), followed by an alcoholysis reaction by methanol (MeOH), is shown in the reaction scheme (B).

Reaction scheme (B)

[Chem. 56]

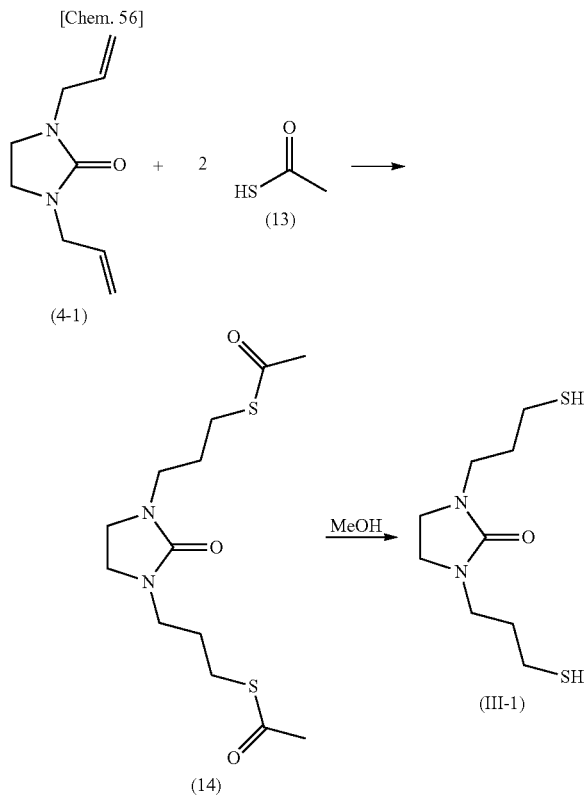

In the first step, a radical initiator (C) may be used in order to accelerate the reaction. Furthermore, a reaction solvent (B) may be used in order to smoothly proceed the reaction.

Examples of the radical initiator (C) include azobisisobutyronitrile, t-hexylperoxyisopropyl monocarbonate, t-hexylperoxy 2-ethylhexanoate, 1,1,3,3-tetramethylbutylperoxy 2-ethylhexanoate, t-butylperoxypivalate, t-hexylperoxypivalate, t-butylperoxyneodecanoate, t-hexylperoxyneodecanoate, 1,1,3,3-tetramethylbutylperoxyneodecanoate, 1,1-bis(t-hexylperoxy)cyclohexane, benzoyl peroxide, 3,5,5-trimethylhexanoyl peroxide, lauroyl peroxide, 2,2'-azobis(2-methylbutyronitrile), dimethyl 2,2'-azobis(2-methylpropionate), and the like.

The amount used (amount charged) of the radical initiator (C) is preferably an appropriate ratio in a range of 0.0001 to 10 molar times the amount used (amount charged) of the dialkene compound.

Examples of the reaction solvent (B) include solvents such as water, methanol, ethanol, propanol, 2-propanol, butanol, ethyl acetate, propyl acetate, butyl acetate, tetrahydrofuran, dioxane, acetonitrile, benzene, toluene, xylene, dichloromethane, chloroform, carbon tetrachloride, dimethylformamide, dimethylacetamide, dimethylsulfoxide, and hexamethylphosphoric triamide. Those may be used in combination as the reaction solvent (B).

In the first step, the reaction temperature is preferably set to be in a range of 0 to 150° C. The reaction time is appropriately set according to the reaction temperature set, but is preferably set to be in a range of 1 to 120 hours.

After completion of the reaction of the first step, the reaction product obtained as a residue after distilling away the reaction solvent and the like from the obtained reaction liquid (reaction mixture) may be subjected to a second step. Furthermore, after completion of the reaction of the first step, the reaction liquid obtained may be directly subjected to the second step.

In the second step, examples of the alcohol used in the alcoholysis reaction include methanol, ethanol, propanol, 2-propanol, butanol, ethylene glycol, propylene glycol, butylene glycol, glycerin, and the like.

In the second step, an acid (D) or a base (E) is preferably used in order to accelerate the reaction. Furthermore, a reaction solvent (F) may be used in order to smoothly proceed the reaction.

Examples of the acid (D) include hydrogen fluoride (hydrofluoric acid), hydrogen chloride (hydrochloric acid), hydrogen bromide (hydrobromic acid), hydrogen iodide (hydroiodic acid), carbonic acid, formic acid, acetic acid, benzoic acid, oxalic acid, citric acid, phosphoric acid, hexafluorophosphoric acid, nitric acid, sulfuric acid, methanesulfonic acid, toluenesulfonic acid, trifluoromethanesulfonic acid, boric acid, boron trifluoride, tetrafluoroboric acid, and the like.

The amount used (amount charged) of the acid (D) is preferably an appropriate ratio in a range of 0.0001 to 10 molar times the amount used (amount produced) of the reaction product of the first step.

Examples of the base (E) include ammonia, trimethylamine, triethylamine, diisopropylethylamine, diazabicycloundecene, diazabicyclononene, pyridine, lithium hydroxide, sodium hydroxide, potassium hydroxide, cesium hydroxide, lithium carbonate, sodium carbonate, potassium carbonate, cesium carbonate, lithium hydrogen carbonate, sodium hydrogen carbonate, potassium hydrogen carbonate, cesium hydrogen carbonate, trilithium phosphate, trisodium phosphate, tripotassium phosphate, tricesium phosphate, dilithium hydrogen phosphate, disodium hydrogen phosphate, dipotassium hydrogen phosphate, dicesium hydrogen phosphate, lithium dihydrogen phosphate, sodium dihydrogen phosphate, potassium dihydrogen phosphate, cesium dihydrogen phosphate, lithium acetate, sodium acetate, potassium acetate, cesium acetate, sodium methoxide, sodium ethoxide, t-butoxypotassium, and the like.

The amount used (amount charged) of the base (E) is preferably an appropriate ratio in a range of 2 to 200 molar times the amount used (amount produced) of the reaction product of the first step.

Examples of the reaction solvent (F) include solvents such as ethyl acetate, propyl acetate, butyl acetate, tetrahydrofuran, dioxane, acetonitrile, benzene, toluene, xylene, dichloromethane, chloroform, carbon tetrachloride, dimethylformamide, dimethylacetamide, dimethylsulfoxide, and hexamethylphosphoric triamide. Those may be used in combination as the reaction solvent (F).

In the second step, the reaction temperature is preferably set to be in a range of 0 to 150° C. The reaction time is appropriately set according to the reaction temperature set, but is preferably set to be in a range of 1 to 120 hours.

After completion of the reaction of the second step, the objective thiol compound of the third embodiment can be extracted from the reaction liquid (reaction mixture) obtained, by the means such as concentration of the reaction liquid by distillation of the reaction solvent or a solvent extraction method.

As necessary, purification can be performed by utilizing the means such as cleaning with water or the like, treatment with activated carbon or silica gel chromatography.

Fourth Embodiment

The thiol compound of the fourth embodiment is a thiol compound obtained by reacting a certain dialkene compound with thioacetic acid or thiobenzoic acid and is represented by the following chemical formula (V), chemical formula (VI) or chemical formula (VII).

[Chem. 57]

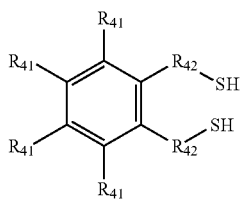
(V)

(In the formula (V), $R_{41}$'s are the same or different and represent a hydrogen atom, a straight chain alkyl group having a carbon number of 1 to 10, a branched chain alkyl group having a carbon number of 3 to 10, or an aryl group. $R_{42}$'s are the same or different and represent a divalent organic group. However, the formula (V) excludes the case where $R_{41}$'s are simultaneously a hydrogen atom and $R_{42}$'s are simultaneously a methylene group (–CH$_2$—) or an ethylene group (—CH$_2$CH$_2$—).)

[Chem. 58]

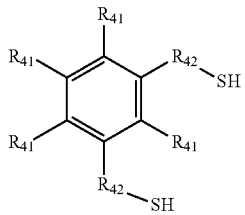
(VI)

(In the formula (VI), $R_{41}$'s and $R_{42}$'s are the same as defined above. However, the formula (VI) excludes the case where $R_{41}$'s are simultaneously a hydrogen atom and $R_{42}$'s are simultaneously a methylene group (—CH$_2$—) or an ethylene group (—CH$_2$CH$_2$—).)

[Chem. 59]

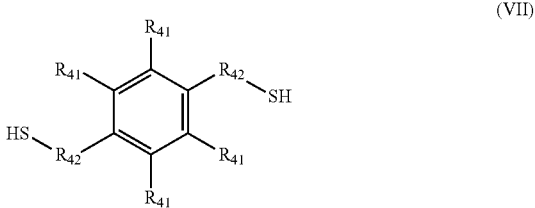
(VII)

(In the formula (VII), $R_{41}$'s and $R_{42}$'s are the same as defined above. However, the formula (VII) excludes the case where $R_4$'s are simultaneously a hydrogen atom and $R_{42}$'s are simultaneously a methylene group (—CH$_2$—), an ethylene group (—CH$_2$CH$_2$—) or a trimethylene group (—CH$_2$CH$_2$CH$_2$—).)

Examples of the thiol compound represented by the chemical formula (V) include thiol compounds represented by the chemical formula (V-1) to chemical formula (V-16).

Examples of the thiol compound represented by the chemical formula (VI) include thiol compounds represented by the chemical formula (VI-1) to chemical formula (VI-6).

Examples of the thiol compound represented by the chemical formula (VII) include thiol compounds represented by the chemical formula (VII-1) to chemical formula (VII-4).

[Chem. 60]

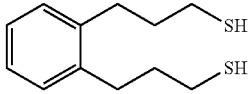
(V-1)

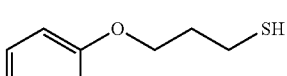
(V-2)

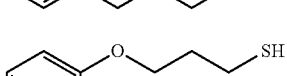
(V-3)

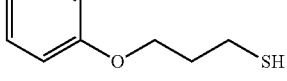
(V-4)

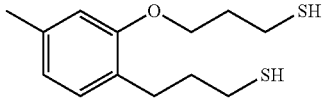
(V-5)

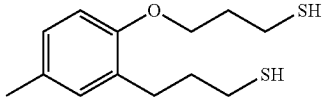
(V-6)

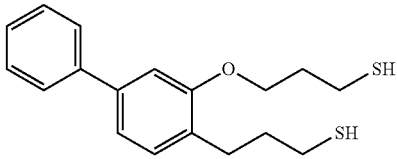

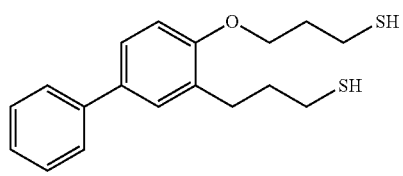 (V-7)
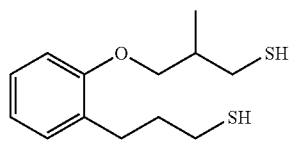 (V-8)
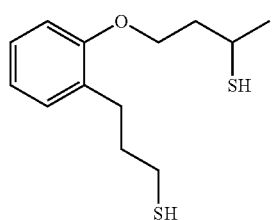 (V-9)
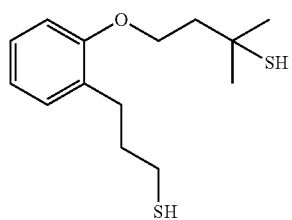 (V-10)
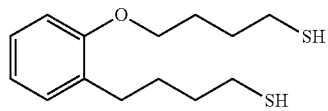 (V-11)
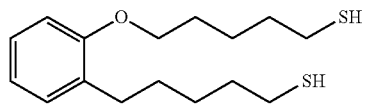 (V-12)
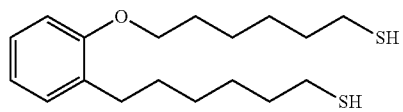 (V-13)
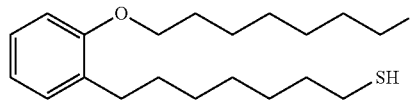 (V-14)
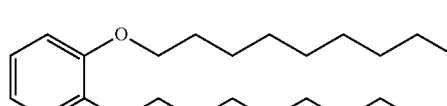 (V-15)
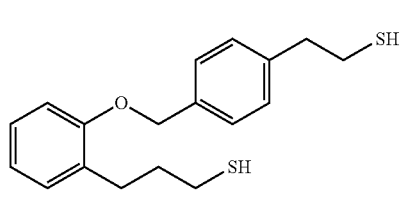 (V-16)
[Chem. 61]
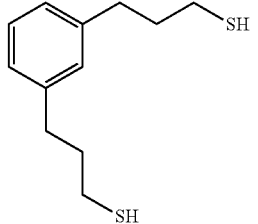 (VI-1)
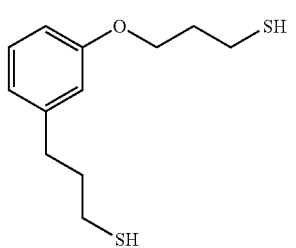 (VI-2)
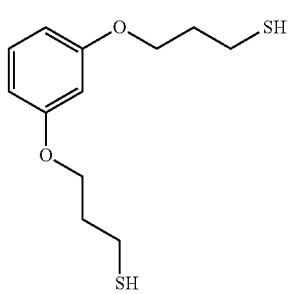 (VI-3)
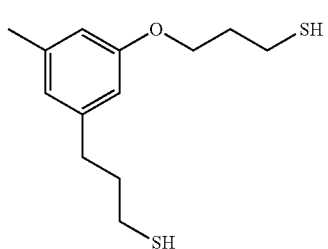 (VI-4)
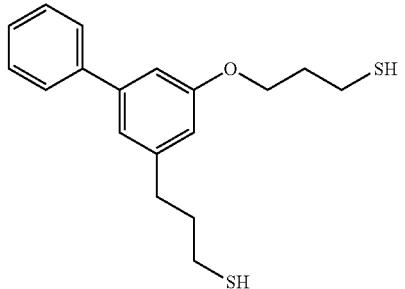 (VI-5)
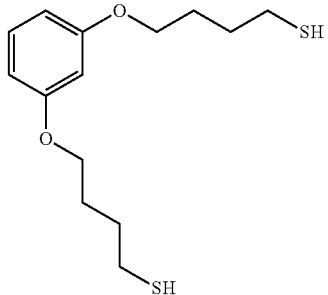 (VI-6)

[Chem. 62]

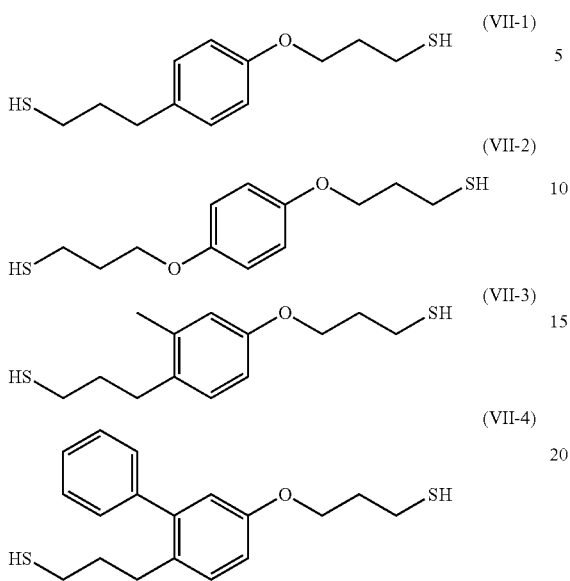

(VII-1)
(VII-2)
(VII-3)
(VII-4)

In the fourth embodiment, $R_{42}$'s in the chemical formula (V), chemical formula (VI) and chemical formula (VII) are, as described above, the same or different and represent a divalent organic group. Examples of the divalent organic group preferably include straight chain alkylene groups having a carbon number of 2 to 10, branched chain alkylene groups having a carbon number of 3 to 10, straight chain alkyleneoxy groups having a carbon number of 2 to 10, branched chain alkyleneoxy groups having a carbon number of 3 to 10, and divalent organic groups represented by the following chemical formula (a) to chemical formula (f). Of those, at least one $R_{42}$ is more preferably an alkyleneoxy group.

[Chem. 63]

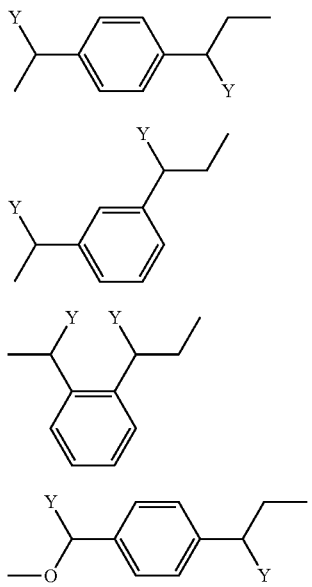

(a)
(b)
(c)
(d)

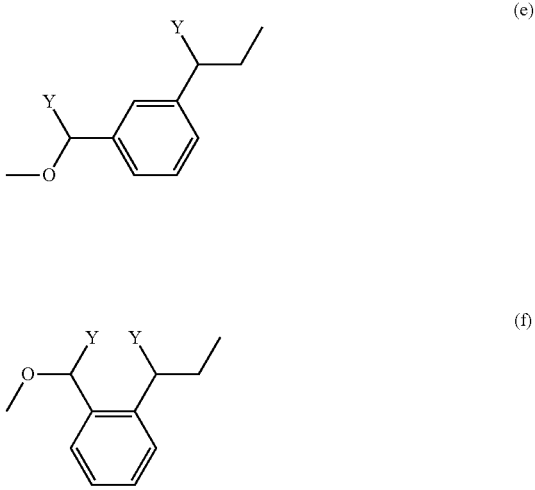

(e)
(f)

(In the formula (a) to formula (f), Y's are the same or different and represent a hydrogen atom or a methyl group.)

In the fourth embodiment, examples of the aryl group include phenyl group, 2-tolyl group, 3-tolyl group, 4-tolyl group, 2,3-xylyl group, 2,4-xylyl group, 2,5-xylyl group, 2,6-xylyl group, 3,4-xylyl group, 3,5-xylyl group, 2,4,6-trimethylphenyl group, 2,3,5-trimethylphenyl group, 2,3,6-trimethylphenyl group, 2,4,5-trimethylphenyl group, 2,3,5,6-tetramethylphenyl group, 1-naphthyl group, 2-naphthyl group, and the like.

The thiol compound of the fourth embodiment can be synthesized by reacting a dialkene compound represented by the chemical formula (6), chemical formula (7) or chemical formula (8) with thioacetic acid or thiobenzoic acid (first step), followed by a hydrolysis reaction or an alcoholysis reaction (alcoholysis) (second step) (see reaction scheme (C) described below). The dialkene compound represented by the chemical formula (6) is a raw material of the thiol compound represented by the chemical formula (V), the dialkene compound represented by the chemical formula (7) is a raw material of the thiol compound represented by the chemical formula (VI), and the dialkene compound represented by the chemical formula (8) is a raw material of the thiol compound represented by the chemical formula (VII).

[Chem. 64]

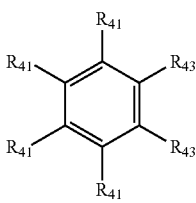

(6)

(In the formula (6), $R_{41}$'s are the same as defined above. $R_{43}$'s are the same or different and represent an organic group having a double bond. However, the formula (6) excludes the case where $R_{41}$'s are simultaneously a hydrogen atom and $R_{43}$'s are simultaneously a vinyl group ($-CH=CH_2$).)

[Chem. 65]

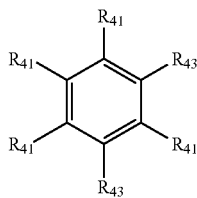
(7)

(In the formula (7), R$_{41}$'s and R$_{43}$'s are the same as defined above. However, the formula (7) excludes the case where R$_{41}$'s are simultaneously a hydrogen atom and R$_{43}$'s are simultaneously a vinyl group (—CH=CH$_2$).)

[Chem. 66]

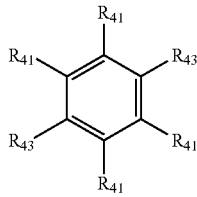
(8)

(In the formula (8), R$_{41}$'s and R$_{43}$'s are the same as defined above. However, the formula (8) excludes the case where R$_{41}$'s are simultaneously a hydrogen atom and R$_{43}$'s are simultaneously a vinyl group (—CH=CH$_2$) or an allyl group (—CH$_2$CH=CH$_2$).)

Examples of the dialkene compound represented by the chemical formula (6) include dialkene compounds represented by the chemical formula (6-1) to formula (6-16).

Examples of the dialkene compound represented by the chemical formula (7) include dialkene compounds represented by the chemical formula (7-1) to formula (7-6).

Examples of the dialkene compound represented by the chemical formula (8) include dialkene compounds represented by the chemical formula (8-1) to formula (8-4).

[Chem. 67]

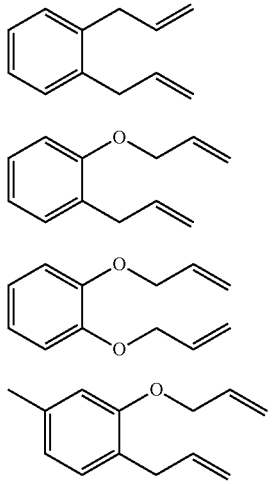

(6-1)

(6-2)

(6-3)

(6-4)

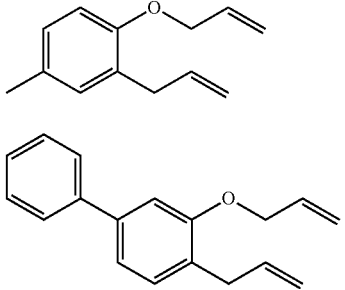

(6-5)

(6-6)

(6-7)

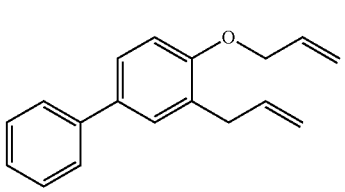
(6-8)

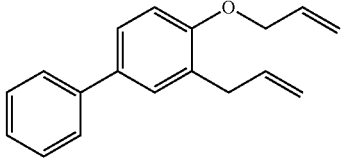
(6-9)

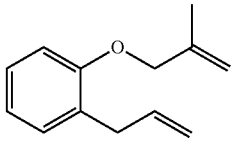
(6-10)

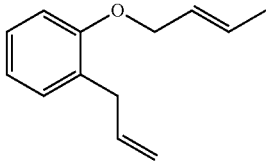
(6-11)

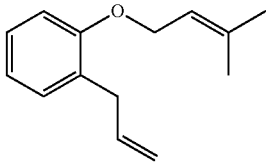
(6-12)

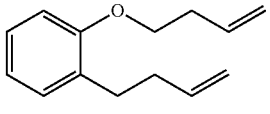
(6-13)

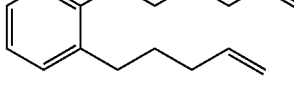
(6-14)

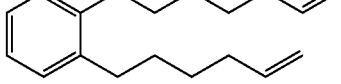
(6-15)

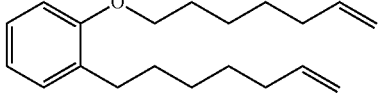

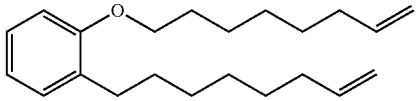

(6-16) 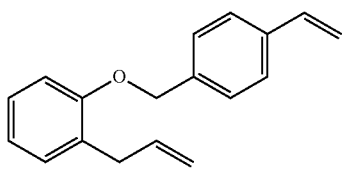

[Chem. 68]

(7-1) 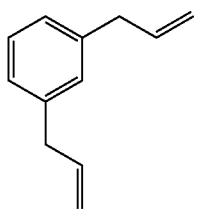

(7-2) 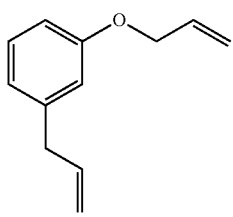

(7-3) 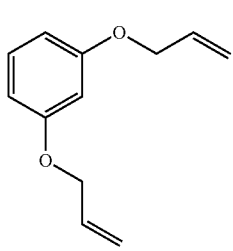

(7-4) 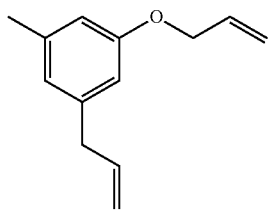

(7-5) 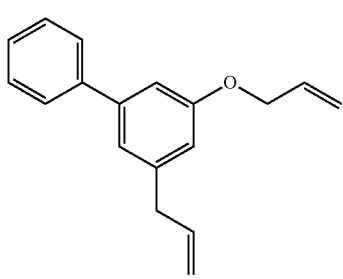

(7-6) 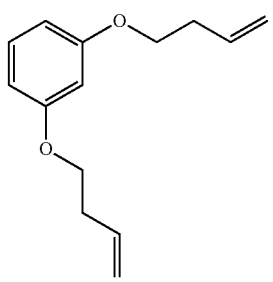

[Chem. 69]

(8-1) 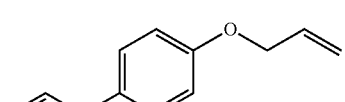

(8-2) 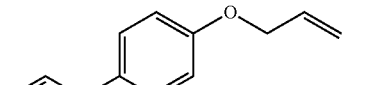

(8-3) 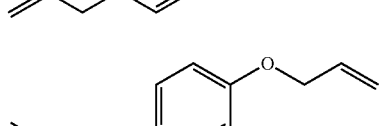

(8-4) 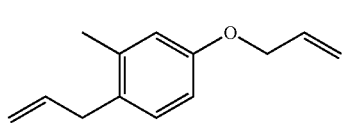

In the fourth embodiment, $R_{43}$'s in the chemical formula (6), chemical formula (7) and chemical formula (8) are, as described above, the same or different and represent an organic group having a double bond. Examples of the organic group can preferably include straight chain alkenyl groups having a carbon number of 2 to 10, branched chain alkenyl groups having a carbon number of 3 to 10, straight chain alkenyloxy groups having a carbon number of 2 to 10, branched chain alkenyloxy groups having a carbon number of 3 to 10, and organic groups represented by the following chemical formula (g) to chemical formula (1).

[Chem. 70]

(g) 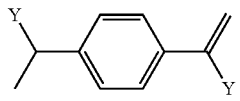

(h) 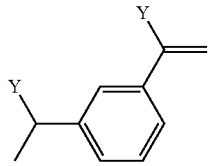

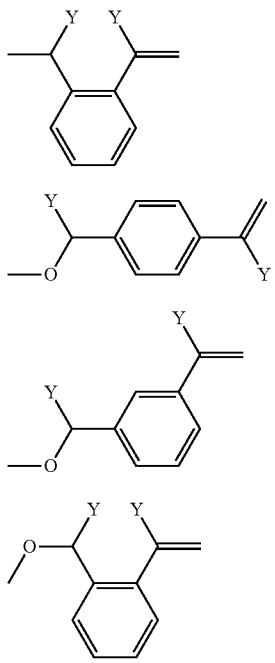

(i)

(j)

(k)

(l)

(In the formula (g) to formula (1), Y is the same as defined above.)

Those dialkene compounds can be synthesized in accordance with the method described in, for example, J. Am. Chem. Soc., vol. 81, pp. 2705-2715 (1959).

In the first step, the amount used (amount charged) of thioacetic acid or thiobenzoic acid is preferably an appropriate ratio in a range of 2 to 40 molar times the amount used (amount charged) of the dialkene compound.

For example, an example that a thiol compound represented by the chemical formula (V-2) is synthesized by reacting a dialkene compound represented by the chemical formula (6-2) with thioacetic acid represented by the chemical formula (13) to obtain a thioacetic acid ester compound represented by the chemical formula (15), followed by an alcoholysis reaction by methanol (MeOH), is shown in the reaction scheme (C).

Reaction scheme (C)

[Chem. 71]

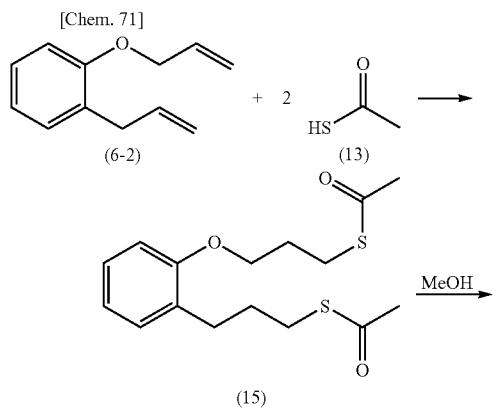

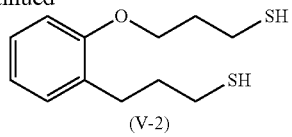

(V-2)

In the first step, a radical initiator (C) may be used in order to accelerate the reaction. Furthermore, a reaction solvent (B) may be used in order to smoothly proceed the reaction.

Examples of the radical initiator (C) include azobisisobutyronitrile, t-hexylperoxyisopropyl monocarbonate, t-hexylperoxy 2-ethylhexanoate, 1,1,3,3-tetramethylbutylperoxy 2-ethylhexanoate, t-butylperoxypivalate, t-hexylperoxypivalate, t-butylperoxyneodecanoate, t-hexylperoxyneodecanoate, 1,1,3,3-tetramethylbutylperoxyneodecanoate, 1,1-bis(t-hexylperoxy)cyclohexane, benzoyl peroxide, 3,5,5-trimethylhexanoyl peroxide, lauroyl peroxide, 2,2'-azobis(2-methylbutyronitrile), dimethyl 2,2'-azobis(2-methylpropionate), and the like.

The amount used (amount charged) of the radical initiator (C) is preferably an appropriate ratio in a range of 0.0001 to 10 molar times the amount used (amount charged) of the dialkene compound.

Examples of the reaction solvent (B) include solvents such as water, methanol, ethanol, propanol, 2-propanol, butanol, ethyl acetate, propyl acetate, butyl acetate, tetrahydrofuran, dioxane, acetonitrile, benzene, toluene, xylene, dichloromethane, chloroform, carbon tetrachloride, dimethylformamide, dimethylacetamide, dimethylsulfoxide, and hexamethylphosphoric triamide. Those may be used in combination as the reaction solvent (B).

In the first step, the reaction temperature is preferably set to be in a range of 0 to 150° C. The reaction time is appropriately set according to the reaction temperature set, but is preferably set to be in a range of 1 to 120 hours.

After completion of the reaction of the first step, the reaction product obtained as a residue after distilling away the reaction solvent and the like from the obtained reaction liquid (reaction mixture) may be subjected to a second step. Furthermore, after completion of the reaction of the first step, the reaction liquid obtained may be directly subjected to the second step.

In the second step, examples of the alcohol used in the alcoholysis reaction include methanol, ethanol, propanol, 2-propanol, butanol, ethylene glycol, propylene glycol, butylene glycol, glycerin, and the like.

In the second step, an acid (D) or a base (E) is preferably used in order to accelerate the reaction. Furthermore, a reaction solvent (F) may be used in order to smoothly proceed the reaction.

Examples of the acid (D) include hydrogen fluoride (hydrofluoric acid), hydrogen chloride (hydrochloric acid), hydrogen bromide (hydrobromic acid), hydrogen iodide (hydroiodic acid), carbonic acid, formic acid, acetic acid, benzoic acid, oxalic acid, citric acid, phosphoric acid, hexafluorophosphoric acid, nitric acid, sulfuric acid, methanesulfonic acid, toluenesulfonic acid, trifluoromethanesulfonic acid, boric acid, boron trifluoride, tetrafluoroboric acid, and the like.

The amount used (amount charged) of the acid (D) is preferably an appropriate ratio in a range of 0.0001 to 10 molar times the amount used (amount produced) of the reaction product of the first step.

Examples of the base (E) include ammonia, trimethylamine, triethylamine, diisopropylethylamine, diazabicycloundecene, diazabicyclononene, pyridine, lithium hydroxide, sodium hydroxide, potassium hydroxide, cesium hydroxide, lithium carbonate, sodium carbonate, potassium carbonate, cesium carbonate, lithium hydrogen carbonate, sodium hydrogen carbonate, potassium hydrogen carbonate, cesium hydrogen carbonate, trilithium phosphate, trisodium phosphate, tripotassium phosphate, tricesium phosphate, dilithium hydrogen phosphate, disodium hydrogen phosphate, dipotassium hydrogen phosphate, dicesium hydrogen phosphate, lithium dihydrogen phosphate, sodium dihydrogen phosphate, potassium dihydrogen phosphate, cesium dihydrogen phosphate, lithium acetate, sodium acetate, potassium acetate, cesium acetate, sodium methoxide, sodium ethoxide, t-butoxypotassium, and the like.

The amount used (amount charged) of the base (E) is preferably an appropriate ratio in a range of 2 to 200 molar times the amount used (amount produced) of the reaction product of the first step.

Examples of the reaction solvent (F) include solvents such as ethyl acetate, propyl acetate, butyl acetate, tetrahydrofuran, dioxane, acetonitrile, benzene, toluene, xylene, dichloromethane, chloroform, carbon tetrachloride, dimethylformamide, dimethyl acetamide, dimethylsulfoxide, and hexamethylphosphoric triamide. Those may be used in combination as the reaction solvent (F).

In the second step, the reaction temperature is preferably set to be in a range of 0 to 150° C. The reaction time is appropriately set according to the reaction temperature set, but is preferably set to be in a range of 1 to 120 hours.

After completion of the reaction of the second step, the objective thiol compound of the fourth embodiment can be extracted from the reaction liquid (reaction mixture) obtained, by the means such as concentration of the reaction liquid by distillation of the reaction solvent or a solvent extraction method.

As necessary, purification can be performed by utilizing the means such as cleaning with water or the like, treatment with activated carbon or silica gel chromatography.

The thiol compound of the present invention including the above-described first embodiment to fourth embodiment is expected to be useful as an intermediate raw material of various sulfur-containing compounds. Furthermore, the thiol compound is useful as a curing agent of a resin, and the curing agent of the present invention contains the thiol compound of the present invention.

The resin composition containing the thiol compound of the present invention is described below.

(First Resin Composition)

The first resin composition of the present invention contains an epoxy resin (note: epoxy resin before curing) and the thiol compound of the present invention contained as a curing agent.

The epoxy resin can be used without particular limitation so long as it has an epoxy group (glycidyl group) in the molecule. Examples thereof include:

polyglycidyl ethers obtained by reacting a polyhydric phenol such as bisphenol A, bisphenol F, bisphenol AD, catechol or resolcinol or a polyhydric alcohol such as glycerin or polyethylene glycol with epichlorohydrin;

glycidyl ether esters obtained by reacting a hydroxycarboxylic acid such as p-hydroxybenzoic acid or β-hydroxynaphthoic acid with epichlorohydrin;

polyglycidyl esters obtained by reacting a polycarboxylic acid such as phthalic acid or terephthalic acid with epichlorohydrin;

glycidyl glycoluril compounds having two or more epoxy groups in the molecule, such as 1,3,4,6-tetraglycidyl glycoluril;

cyclic alicyclic epoxy resins such as 3',4'-epoxycyclohexylmethyl-3,4-epoxycyclohexane carboxylate;

nitrogen-containing cyclic epoxy resins such as triglycidyl isocyanurate and a hydantoin epoxy resin; as well as epoxidized phenol novolac resins, epoxidized cresol novolac resins, epoxidized polyolefins, cycloaliphatic epoxy resins, and urethane-modified epoxy resins;

additionally, epoxy-modified organopolysiloxane compounds by a hydrosilylation addition reaction between an organic compound having a carbon-carbon double bond and glycidyl group and a silicon compound having SiH group (e.g., epoxy-modified organopolysiloxane compounds disclosed in JP-A-2004-99751 and JP-A-2006-282988); and the like. Those compounds may be used in combination.

The content of the thiol compound of the present invention in the first resin composition of the present invention is preferably set such that the ratio (equivalent ratio) of the number of the thiol group in the resin composition to the number of the epoxy group therein is from 0.1 to 10.0.

In the first resin composition of the present invention, another thiol compound may be used together with the thiol compound of the present invention to form a curing agent. Examples of the other thiol compound include:

aliphatic thiol compounds such as ethane dithiol, propane dithiol, hexamethylene dithiol, decamethylene dithiol, tolylene-2,4-dithiol, 2,2-bis(mercaptomethyl)-1,3-propanedithiol, 2-(mercaptomethyl)-2-methyl-1,3-propanedithiol, and 2-ethyl-2-(mercaptomethyl)-1,3-propanedithiol;

aromatic thiol compounds such as benzenedithiol, toluenedithiol and xylenedithiol (p-xylenedithiol);

cyclic sulfide compounds such as a 1,4-dithiane ring-containing polythiol compound represented by the chemical formula (11);

mecaptoalkyl sulfide compounds such as 3-thiapentane-1,5-dithiol and 4-mercaptomethyl-3,6-dithia-1,8-octanedithiol;

mercaptopropionic acid esters such as pentaerythritoltetrakis(3-mercaptopropionate);

epoxy resin-terminated mercapto compounds;

mercaptoalkyl ether compounds such as 3,6-dioxa-1,8-octanedithiol, a mercaptoalkyl ether disulfide compound represented by the chemical formula (12), 2,2'-[[2,2-bis[(2-mercaptoethoxy)methyl]-1,3-propanediyl]bis(oxy)]bisethanethiol, 3,3'-[[2,2-bis[(3-mercaptopropoxy)methyl]-1,3-propanediyl]bis(oxy)]bis-1-propanethiol, 3-[2,2-bis[(3-mercaptopropoxy)methyl]butoxy]-1-propanethiol, 3-(3-mercaptopropoxy)-2,2-bis[(3-mercaptopropoxy)methyl]-1-propanol, and 2,2-bis[(3-mercaptopropoxy)methyl]-1-butanol;

1,3,4,6-tetrakis(2-mercaptoethyl)glycoluril;

1,3,4,6-tetrakis(3-mercaptopropyl)glycoluril; and the like. Those may be used in combination.

[Chem. 72]

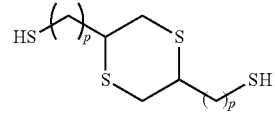

(11)

(In the formula (11), p is an integer of 1 to 5.)

[Chem. 73]

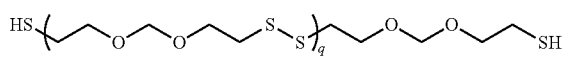

(In the formula (12), q is an integer of 1 to 20.)

The content of the other thiol compound in the first resin composition of the present invention is preferably set such that the ratio (equivalent ratio) of the number of the thiol group derived from the other thiol compound in the composition to the number of the thiol group derived from the thiol compound of the present invention is 0 to 100.

The first resin composition of present invention may contain a conventionally-known curing agent together with the thiol compound of the present invention. Examples of the conventionally-known curing agent include:

compounds having a phenolic hydroxyl group and acid anhydrides: as well as organic phosphine compounds such as triphenylphosphine, diphenylnaphthylphosphine and diphenylethylphosphine;

aromatic phosphonium salts;

aromatic diazonium salts;

aromatic iodonium salts;

aromatic selenium salts; and the like.

Examples of the compounds having a phenolic hydroxyl group include bisphenol A, bisphenol F, bisphenol S, tetramethylbisphenol A, tetramethylbisphenol F, tetramethylbiphenol S, tetrachlorobisphenol A, tetrabromobisphenol A, dihydroxynaphthalene, phenol novolac, cresol novolac, bisphenol A novoalc, brominated phenol novolac, resorcinol, and the like.

Examples of the acid anhydrides include methyltetrahydrophthalic anhydride, methylhexahydrophthalic anhydride, hexahydrophthalic anhydride, 5-norbornene-2,3-dicarboxylic anhydride, trimellitic anhydride, nadic anhydride, hymic anhydride, methylnadic anhydride, methylbicyclo[2.2.1]heptane-2,3-dicarboxylic anhydride, bicyclo[2.2.1]heptane-2,3-dicarboxylic anhydride, methylnorbornane-2,3-dicarboxylic acid, and the like.

The first resin composition of the present invention may contain a conventionally-known curing accelerator. Examples of the curing accelerator include (i) amines, (ii) reaction products between an epoxy compound and an amine, (iii) reaction products between a compound having one or more isocyanate group in the molecule and a compound having at least one of a primary amino group and a secondary amino group in the molecule, and the like. Those may be used in combination.

(i) Any amine suffices as the amines as long as it has at least one amino group selected from primary amino group, secondary amino group and tertiary amino group in the molecule, as conventionally known.

Examples of the amines include:

aliphatic amines such as diethylenetriamine, triethylenetetramine, n-propylamine, 2-hydroxyethylaminopropylamine, cyclohexylamine, and 4,4'-diaminodicyclohexylmethane;

aromatic amines such as 4,4'-diaminodiphenylmethane and o-methylaniline;

nitrogen-containing heterocyclic compounds such as 2-ethyl-4-methylimidazole, 2-methylimidazole, 2-ethyl-4-methylimidazoline, 2,4-dimethylimidazoline, piperidine, and piperazine; and the like.

The content of the amine in the first resin composition of the present invention is preferably 0.1 to 100 parts by weight per 100 parts by weight of the epoxy compound (epoxy resin).

(ii) The reaction product between an epoxy resin and an amine is a solid slightly soluble in an epoxy resin at room temperature, solubilizes (easily solubilizes) by heating and functions as a curing accelerator. Therefore, it is also called a latent curing accelerator (the reaction product between an epoxy compound and an amine is hereinafter sometimes referred as a "latent curing accelerator").

Examples of the epoxy resin used as a raw material of the latent curing accelerator include:

the epoxy compounds described above; as well as glycidylamine compounds obtained by reacting 4,4'-diaminodiphenylmethane, m-aminophenol or the like with epichlorohydrin; and monofunctional epoxy compounds such as butylglycidyl ether, phenylglycidyl ether and glycidyl methacrylate.

Examples of the amine used as a raw material of the latent curing accelerator include the amines described above. Of those amines, amines having tertiary amino group in the molecule are materials capable of giving a latent curing accelerator having excellent curing accelerating properties. Examples of such amines include:

amines such as dimethylaminopropylamine, diethylaminopropylamine, di-n-propylaminopropylamine, dibutylaminopropylamine, dimethylaminoethylamine, diethylaminoethylamine, and N-methylpiperazine;

amines having a tertiary amino group in the molecule, such as imidazole compounds such as 2-methylimidazole, 2-ethylimidazole, 2-ethyl-4-methylimidazole, and 2-phenylimidazole;

alcohols, phenols, thiols, carboxylic acids, and hydrazides, having a tertiary amino group in the molecule, such as 2-dimethylaminoethanol, 1-methyl-2-dimethylaminoethanol, 1-phenoxymethyl-2-dimethylaminoethanol, 2-diethylaminoethanol, 1-butoxymethyl-2-dimethylaminoethanol, 1-(2-hydroxy-3-phenoxypropyl)-2-methylimidazole, 1-(2-hydroxy-3-phenoxypropyl)-2-ethyl-4-methylimidazole, 1-(2-hydroxy-3-butoxypropyl)-2-methylimidazole, 1-(2-hydroxy-3-butoxypropyl)-2-ethyl-4-methylimidazole, 1-(2-hydroxy-3-phenoxypropyl)-2-phenylimidazoline, 1-(2-hydroxy-3-butoxypropyl)-2-methylimidazoline, 2-(dimethylaminomethyl)phenol, 2,4,6-tris(dimethylaminomethyl)phenol, N-β-hydroxyethyl morpholine, 2-dimethylaminoethanethiol, 2-mercaptopyridine, 2-mercaptobenzoimidazole, 2-mercaptobenzothiazole, 4-mercaptopyridine, N,N-dimethylaminobenzoic acid, N,N-dimethylglycine, nicotinic acid, isonicotinic acid, picolinic acid, N,N-dimethylglycine hydrazide, N,N-dimethylpropionic acid hydrazide, nicotinic acid hydrazide, and isonicotinic acid hydrazide; and the like.

An active hydrogen compound having two or more active hydrogens in the molecule can be added as a third component to the latent curing accelerator in order to further improve storage stability of the first resin composition of the present invention.

Examples of the active hydrogen compound include:

polyhydric phenols such as bisphenol A, bisphenol F, bisphenol S, hydroquinone, catechol, resorcinol, pyrogallol, and a phenol novolac resin;

polyhydric alcohols such as trimethylolpropane;

polyhydric carboxylic acids such as adipic acid and phthalic acid;

1,2-dimercaptoethane, 2-mercaptoethanol, 1-mercapto-3-phenoxy-2-propanol, mercaptoacetic acid, anthranilic acid, lactic acid, and the like.

The latent curing accelerator may be surface-treated with an isocyanate compound or an acidic compound. Examples of the isocyanate compound include:

monofunctional isocyanate compounds such as n-butyl isocyanate, isopropyl isocyanate, phenyl isocyanate, and benzyl isocyanate; and polyfunctional isocyanate compounds such as hexamethylene diisocyanate, toluylene diisocyanate, 1,5-naphthalene diisocyanate, diphenylmethane-4,4'-diisocyanate, isophorone diisocyanate, xylene diisocyanate, paraphenylene diisocyanate, 1,3,6-hexamethylene triisocyanate, and bicycloheptane triisocyanate.

In place of the polyfunctional isocyanate compound, a terminal isocyanate group-containing compound obtained by a reaction between a polyfunctional isocyanate compound and an active hydrogen compound can be used. Specific examples thereof include an addition reaction product having a terminal isocyanate group, obtained by a reaction between toluylene diisocyanate and trimethylolpropane, an addition reaction product having a terminal isocyanate group, obtained by a reaction between toluylene diisocyanate and pentaerythritol, and the like.

The acidic substance used in the surface treatment of the latent curing accelerator may be any of gas, liquid and solid, and may be any of an inorganic acid and an organic acid. Examples of the acidic substance include carbon dioxide gas, sulfurous acid gas, sulfuric acid, hydrochloric acid, oxalic acid, phosphoric acid, acetic acid, formic acid, propionic acid, adipic acid, caproic acid, lactic acid, succinic acid, tartaric acid, sebacic acid, p-toluenesulfonic acid, salicylic acid, boric acid, tannic acid, alginic acid, polyacrylic aid, polymethacrylic acid, phenol, pyrogallol, phenol resins, resorcin resins, and the like.

The latent curing accelerator can be easily obtained by mixing an epoxy resin, an amine and as necessary, an active hydrogen compound, and reacting the resulting mixture at a temperature of room temperature to 200° C. and then, solidifying and pulverizing, or reacting those compounds in a solvent such as methyl ethyl ketone, dioxane or tetrahydrofuran, removing the solvent and pulverizing the solid component.

A commercially available latent curing accelerator can be used. Examples of the commercially available product include "AMICURE PN-23 (trade name)", "AMICURE PN-H (trade name)" and "AMICURE MY-24 (trade name)", manufactured by Ajinomoto Fine-Techno Co., Inc., "NOVACURE HX-3721 (trade name)" and "NOVACURE HX-3742 (trade name)", manufactured by Asahi Kasei Corporation, and the like.

The content of the latent curing accelerator in the first resin composition of the present invention is preferably 0.1 to 1000 parts by weight per 100 parts by weight of the epoxy compound (epoxy resin).

(iii) The reaction product between a compound having one or more isocyanate group in the molecule and a compound having at least one of a primary amino group and a secondary amino group in the molecule can be obtained by reacting the isocyanate compound having one or more isocyanate group in the molecule with the compound having at least one of a primary amino group and a secondary amino group in the molecule in an organic solvent such as dichloromethane.

Examples of the isocyanate compound having one or more isocyanate group in the molecule include n-butyl isocyanate, isopropyl isocyanate, 2-chloroethyl isocyanate, phenyl isocyanate, p-bromophenyl isocyanate, m-chlorophenyl isocyanate, o-chlorophenyl isocyanate, p-chlorophenyl isocyanate, 2,5-dichlorophenyl isocyanate, 3,4-dichlorophenyl isocyanate, 2,6-dimethylphenyl isocyanate, o-fluorophenyl isocyanate, p-fluorophenyl isocyanate, m-tolyl isocyanate, p-tolyl isocyanate, o-trifluoromethylphenyl isocyanate, m-trifluoromethylphenyl isocyanate, benzyl isocyanate, hexamethylene diisocyanate, 2,4-toluylene diisocyanate, 2,6-toluylene diisocyanate, 1,5-naphthalene diisocyanate, diphenylmethane-4,4'-diisocyanate, 2,2-dimethyldiphenylmethane-4,4'-diisocyanate, tolidine diisocyanate, isophorone diisocyanate, xylylene diisocyanate, 1,3-bis(isocyanatemethyl)-cyclohexane, p-phenylene diisocyanate, 1,3,6-hexamethylene triisocyanate, bicycloheptane triisocyanate, tris-(3-isocyanato-4-methylphenyl)isocyanurate, tris-(6-isocyanatohexyl)-isocyanurate, and the like.

Examples of the compound having at least one of a primary amino group and a secondary amino group in the molecule include dimethylamine, diethylamine, di-n-propylamine, di-n-butylamine, di-n-hexylamine, di-n-octylamine, di-n-ethanolamine, dimethylaminopropylamine, diethylaminopropylamine, morpholine, piperidine, 2,6-dimethylpiperidine, 2,2,6,6-tetramethylpiperidine, piperazine, pyrrolidine, benzylamine, N-methylbenzylamine, cyclohexylamine, m-xylylenediamine, 1,3-bis(aminomethyl)cyclohexane, isophorone diamine, N-aminoethylpiperazine, 2-methylimidazole, 2-ethyl-4-methylimidazole, 2-undecylimidazole, 2-phenylimidazole, 1,1-dimethylhydrazine, and the like.

The content of the reaction product between the compound having one or more isocyanate group in the molecule and the compound having at least one of a primary amino group and a secondary amino group in the molecule in the first resin composition of the present invention is preferably 1 to 10 parts by weight per 100 parts by weight of the epoxy compound (epoxy resin).

As necessary, the first resin composition of the present invention may contain the following materials in a proportion of 0.01 to 50 wt % based on the entire first resin composition (total amount) so long as the effect of the present invention is not impaired:

a pigment (titanium white, cyanine blue, watching red, red iron oxide, carbon black, aniline black, manganese blue, iron black, ultramarine blue, Hansa red, chrome yellow, chrome green, etc.);

an inorganic filler (calcium carbonate, kaolin, clay, talc, mica, barium sulfate, lithopone, gypsum, zinc stearate, perlite, quartz, quartz glass, molten silica, silica powder or the like such as spherical silica, oxides such as spherical alumina, pulverized alumina, magnesium oxide, beryllium oxide, and titanium oxide, nitrides such as boron nitride, silicon nitride and aluminum nitride, carbides such as silicon carbide, hydroxides such as aluminum hydroxide and magnesium hydroxide, metals such as copper, silver, iron, aluminum, nickel, and titanium, and alloys thereof, carbonaceous materials such as diamond and carbon, etc.);

a thermoplastic resin and/or thermosetting resin (high density, medium density and low density various polyethylenes, homopolymers such as polypropylene, polybutene and polypentene, ethylene-propylene copolymer, polyamide resins such as nylon-6 and nylon-6,6, vinyl chloride resins, nitrocellulose resins, vinylidene chloride resins, acrylic resins, acrylamide resins, styrene resins, vinyl ester resins, polyester resins, phenol resins (phenol compounds), silicone resins, fluorine resins, various elastomer resins such as acryl rubber and urethane rubber, graft copolymers such as methyl methacrylate-butadiene-styrene graft copolymer and acrylonitrile-butadiene-styrene graft copolymer, etc.), a reinforcing agent (glass fiber, carbon fiber, etc,), an anti-sagging agent (hydrogenated castor oil, silicic anhydride fine particle, etc.), a matting agent (silica fine powder, paraffin wax, etc.), an abrasive (zinc stearate, etc.), an internal mold release agent (fatty acids such as stearic acid, fatty acid metal salts such as calcium stearate, fatty acid amides such as stearic acid amide, fatty acid esters, polyolefin wax, paraffin wax, etc.), and an additive (modifier) such as a surfactant, leveling agent, defoaming agent, diluent for viscosity adjustment (organic solvent), flexibilizer, coupling agent, perfume, flame retardant, and anti-oxidant.

In the first resin composition of the present invention, in the case where an isocyanate group-containing compound is contained as an additive, adhesive force can be enhanced while suppressing the deterioration of curing properties of the resin composition.

Examples of the isocyanate group-containing compound include n-butyl isocyanate, isopropyl isocyanate, 2-chloroethyl isocyanate, phenyl isocyanate, p-chlorophenyl isocyanate, benzyl isocyanate, hexamethylene diisocyanate, 2-ethylphenyl isocyanate, 2,6-dimethylphenyl isocyanate, 2,4-toluene diisocyanate, 2,6-toulene diisocyanate, 1,5-naphthalene diisocyanate, diphenylmethane-4,4'-diisocyanate, tolidine diisocyanate, isophorone diisocyanate, xylylene diisocyanate, p-phenylene diisocyanate, 1,3,6-hexamethylene triisocyanate, bicycloheptane triisocyanate, and the like.

The content of the isocyanate group-containing compound in the first resin composition of the present invention is preferably 0.1 to 20 parts by weight per 100 parts by weight of the epoxy compound (epoxy resin).

A method for preparing (mixing) the first resin composition of the present invention is not particularly limited. Predetermined amounts of the respective components described above are weighed and those components can be mixed by using an appropriate stirring/mixing apparatus while heating as necessary.

A method for curing the first resin composition of the present invention is not particularly limited and use can be made of a conventionally-known curing apparatus such as a closed curing furnace and a tunnel furnace capable of performing continuous curing. Heating source is also not particularly limited, and use can be made of a conventionally-known means such as hot air circulation, infrared heating and high frequency heating. Curing temperature and curing time are appropriately set.

(Second Resin Composition)

The second resin composition of the present invention contains the thiol compound of the present invention and an enic compound having a carbon-carbon double bond in the molecule (hereinafter simply referred to as an "enic compound").

The enic compound includes both a polymerizable monomer and a polymerizable oligomer (semi-cured product) having a structure that a polymerizable monomer has been partially polymerized.

Examples of the polymerizable monomer include:
(1) (meth)acrylic acid alkyl ester monomers;
(2) hydroxyl group-containing monomers;
(3) carboxyl group-containing monomers;
(4) amino group-containing monomers;
(5) acetoacetyl group-containing monomers;
(6) isocyanate group-containing monomers;
(7) glycidyl group-containing monomers;
(8) monomers having one aromatic ring;
(9) monomers having an alkoxy group and an oxyalkylene group;
(10) alkoxyalkyl (meth)acrylamide monomers;
(11) (meta)acrylamide monomers;
(12) monofunctional unsaturated compounds;
(13) polyfunctional unsaturated monomers; and the like.

(1) Examples of the (meth)acrylic acid alkyl ester monomer include:
methyl (meth)acrylate,
ethyl (meth)acrylate,
n-butyl (meth)acrylate,
i-butyl (meth)acrylate,
t-butyl (meth)acrylate,
n-propyl (meth)acrylate,
n-hexyl (meth)acrylate,
2-ethylhexyl (meth)acrylate,
n-octyl (meth)acrylate,
isodecyl (meth)acrylate,
lauryl (meth)acrylate,
cetyl (meth)acrylate,
stearyl (meth)acrylate,
cyclohexyl (meth)acrylate,
isobornyl (meth)acrylate, and the like.

(2) Examples of the hydroxy group-containing monomer include:
(meth)acrylic acid hydroxyalkyl esters such as:
2-hydroxyethyl (meth)acrylate,
4-hydroxybutyl (meth)acrylate,
5-hydroxypentyl (meth)acrylate,
6-hydroxyhexyl (meth)acrylate, and
8-hydroxyoctyl (meth)acrylate;
caprolactone-modified monomers such as:
caprolactone-modified 2-hydroxyethyl (meth)acrylate; and
oxyalkylene-modified monomers such as:
diethylene glycol (meth)acrylate, and
polyethylene glycol (meth)acrylate; as well as
primary hydroxyl group-containing monomers such as:
2-acryloyloxyethyl 2-hydroxyethyl phthalic acid,
N-methylol (meth)acrylamide, and
hydroxyethyl acrylamide;
secondary hydroxyl group-containing monomers such as:
2-hydroxypropyl (meth)acrylate,
2-hydroxybutyl (meth)acrylate,
3-chloro-2-hydroxypropyl (meth)acrylate,
propyleneglycol diglycidyl ether-epoxydi(meth)acrylate,
phenol glycidyl ether-epoxy(meth)acrylate, and
bisphenol A diglycidyl ether-epoxydi(meth)acrylate;
tertiary hydroxyl-group-containing monomers such as:
2,2-dimethyl 2-hydroxyethyl (meth)acrylate; and the like.

(3) Examples of the carboxyl group-containing monomer include:
(meth)acrylic acid, acrylic acid dimer, crotonic acid, maleic acid, maleic anhydride, fumaric acid, citraconic acid, glutaconic acid, itaconic acid, acrylamide N-glycolic acid, cinnamic acid, and the like.

(4) Examples of the amino group-containing monomer include:
t-butylaminoethyl (meth)acrylate,
ethylaminoethyl (meth)acrylate,
dimethylaminoethyl (meth)acrylate,
diethylaminoethyl (meth)acrylate, and the like.

(5) Examples of the acetoacetyl group-containing monomer include:
2-(acetoacetoxy)ethyl (meth)acrylate,
allyl acetoacetate, and the like.

(6) Examples of the isocyanate group-containing monomer include:
2-acryloyloxyethyl isocyanate,
2-methacryloyloxyethyl isocyanate,
alkylene oxide adducts thereof, and the like.

(7) Examples of the glycidyl group-containing monomer include:
glycidyl (meth)acrylate, as well as
ethylene glycol diglycidyl ether-epoxy(meth)acrylate,
resorcin diglycidyl ether-epoxy(meth)acrylate,
bis(4-hydroxyphenyl)sulfide diglycidyl ether-epoxy(meth)acrylate,
phenol novolac epoxy resin-(meth)acrylate,
cresol novolac epoxy resin-(meth)acrylate,
bisphenol (e.g., bisphenol A or bisphenol F) epoxy resin-(meth)acrylate,
biphenol (e.g., 3,3',5,5'-tetramethyl biphenol) epoxy resin-(meth)acrylate,
epoxy(meth)acrylates such as a reaction product between an epoxy compound such as tris(2,3-epoxypropyl)isocyanurate-(meth)acrylate and (meth)acrylic acid,
glycidyl (meth)acrylates such as 4-hydroxybutyl(meth)acrylate glycidyl ether, and the like.

(8) Examples of the monomer having one aromatic ring include:
phenyl (meth)acrylate,
benzyl (meth)acrylate,
phenoxyethyl (meth)acrylate,
phenoxydiethylene glycol (meth)acrylate,
2-hydroxy-3-phenoxyproply (meth)acrylate,
styrene,
α-methyl styrene, and the like.

(9) Examples of the monomer having an alkoxy group and an oxyalkylene group include:
2-methoxyethyl (meth)acrylate,
2-ethoxyethyl (meth)acrylate,
3-methoxybutyl (meth)acrylate,
2-butoxyethyl (meth)acrylate,
2-butoxydiethylene glycol (meth)acrylate,
methoxydiethylene glycol (meth)acrylate,
methoxytriethylene glycol (meth)acrylate,
ethoxydiethylene gycol (meth)acrylate,
methoxydipropylene glycol (meth)acrylate,
methoxypolyethylene glycol (meth)acrylate,
octoxypolyethylene glycol-polypropylene glycol-mono (meth)acrylate,
lauroxypolyethylene glycol mono(meth)acrylate,
stearoxypolyethylene glycol mono(meth)acrylate, and the like.

(10) Examples of the alkoxyalkyl (meth)acrylamide monomer include:
methoxymethyl (meth)acrylamide,
ethoxymethyl (meth)acrylamide,
propoxymethyl (meth)acrylamide,
isopropoxymethyl (meth)acrylamide,
n-butoxymethyl (meth)acrylamide,
isobutoxymethyl (meth)acrylamide, and the like.

(11) Examples of the (meth)acrylamide monomer include:
(meth)acryloyl morpholine,
dimethyl (meth)acrylamide,
diethyl (meth)acrylamide,
(meth)acrylamide N-methylol (meth)acrylamide, and the like.

(12) Examples of the monofunctional unsaturated compound include biphenyl structure-containing (meth)acrylate compounds. Specific examples thereof include:
biphenyl (meth)acrylates such as:
o-biphenyl (meth)acrylate,
m-biphenyl (meth)acrylate, and
p-biphenyl (meth)acrylate;
biphenyloxyalkyl (meth)acrylates such as:
o-biphenyloxymethyl (meth)acrylate,
m-biphenyloxymethyl (meth)acrylate,
p-biphenyloxymethyl (meth)acrylate,
o-biphenyloxyethyl (meth)acrylate,
m-biphenyloxyethyl (meth)acrylate,
p-biphenyloxyethyl (meth)acrylate,
o-biphenyloxypropyl (meth)acrylate,
m-biphenyloxypropyl (meth)acrylate, and
p-biphenyloxypropyl (meth)acrylate;
biphenyloxypolyalkylene glycol (meth)acrylates such as:
(o-biphenyloxy)di ethylene glycol (meth)acrylate,
(m-biphenyloxy)diethylene glycol (meth)acrylate,
(p-biphenyloxy)di ethylene glycol (meth)acrylate,
(o-biphenyloxy)dipropylene glycol (meth)acrylate,
(m-biphenyloxy)dipropylene glycol (meth)acrylate,
(p-biphenyloxy)dipropylene glycol (meth)acrylate,
(o-biphenyloxy)polyethylene glycol (meth)acrylate,
(m-biphenyloxy)polyethylene glycol (meth)acrylate,
(p-biphenyloxy)polyethylene glycol (meth)acrylate,
(o-biphenyloxy)polypropylene glycol (meth)acrylate,
(m-biphenyloxy)polypropylene glycol (meth)acrylate, and
(p-biphenyloxy)polypropylene glycol (meth)acrylate; and the like.

(13) Examples of the polyfunctional unsaturated compound include bifunctional monomers, tri- or more functional monomers, urethane (meth)acrylates, the above-described epoxy(meth)acrylates, polyester (meth)acrylates, polyether (meth)acrylates, and the like.

Specific examples of the bifunctional monomer include:
ethylene glycol di(meth)acrylate,
diethylene glycol di(meth)acrylate,
triethylene glycol di(meth)acrylate,
tetraethylene glycol di(meth)acrylate,
polyethylene glycol di(meth)acrylate,
propylene glycol di(meth)acrylate,
dipropylene glycol di(meth)acrylate,
polypropylene glycol di(meth)acrylate,
butylene glycol di(meth)acrylate,
neopentyl glycol di(meth)acrylate,
ethylene oxide-modified bisphenol A di(meth)acrylate,
propylene oxide-modified bisphenol A di(meth)acrylate,
1,6-hexanediol di(meth)acrylate,
1,6-hexanediol ethylene oxide-modified di(meth)acrylate,
glycerin di(meth)acrylate,
pentaerythritol di(meth)acrylate,
ethylene glycol diglycidyl ether di(meth)acrylate,
diethylene glycol diglycidyl ether di(meth)acrylate,
phthalic acid diglycidyl ester di(meth)acrylate,
hydroxypivalic acid-modified neopentyl glycol di(meth)acrylate,
isocyanuric acid ethylene oxide-modified diacrylate,
2-(meth)acryloyloxyethyl acid phosphate diester, and the like.

Specific examples of the tri- or more functional monomer include:
trimethylolpropane tri(meth)acrylate,
pentaerythritol tri(meth)acrylate,
pentaerythritol tetra(meth)acrylate,
dipentaerythritol tri(meth)acrylate, dipentaerythritol tetra(meth)acrylate,
dipentaerythritol penta(meth)acrylate,
dipentaerythritol hexa(meth)acrylate,
tri(meth)acryloyloxyethoxytrimethylolpropane,
glycerin polyglycidyl ether poly(meth)acrylate,
tris(2-(meth)acryloyloxyethyl)isocyanurate,
isocyanuric acid ethylene oxide-modified tri(meth)acrylate,
ethylene oxide-modified dipentaerythritol penta(meth)acrylate,
ethylene oxide-modified dipentaerythritol hexa(meth)acrylate,
ethylene oxide-modified pentaerythritol tri(meth)acrylate,
ethylene oxide-modified pentaerythritol tetra(meth)acrylate,
succinic acid-modified pentaerythritol tri(meth)acrylate, and the like.

Other than the above-described polymerizable monomers, examples further include:
divinylbenzene, piperylene, isoprene, pentadiene, vinylcyclohexene, chloroprene, butadiene, methylbutadiene, cyclopentadiene, methylpentadiene, acrylonitrile, methacrylonitrile, vinyl acetate, vinyl propionate, vinyl stearate, vinyl chloride, vinylidene chloride, alkyl vinyl ether, vinyltoluene, vinylpyridine, vinylpyrrolidone, itaconic acid dialkyl ester, fumaric acid dialkyl ester, allyl alcohol, acryloyl chloride, methyl vinyl ketone, N-acrylamide methyl trimethylammonium chloride, allyl trimethylammonium chloride, dimethylallyl vinylketone, 2-chloroethyl vinyl ether, triallyl isocyanurate, tetraallyl glycoluril,
N-vinylpyrrolidone, N-vinyl caprolactam, ethylene glycol diallyl carbonate, trimellitic acid triallyl ester,
trifluoroethyl (meth)acrylate,
tribromobenzyl (meth)acrylate,
perfluorooctylethyl (meth)acrylate,
sulfur-containing (meth)acrylate,
(meth)acryloyloxypropyl tris(methoxy)silane, and the like.

In the second resin composition of the present invention, the above-described polymerizable monomer and polymerizable oligomer may be used in combination as an enic compound, the polymerizable monomers exemplified above may be used in combination as the polymerizable monomer (different kinds of polymerizable monomers may be used in combination), and different kinds of polymerizable oligomers may be used in combination as the polymerizable oligomer.

The ratio (proportion) of the contents between the thiol compound of the present invention and the enic compound in the second resin composition of the present invention is preferably set such that the content of the enic compound is preferably an appropriate ratio in a range of 0.01 to 1000 times (weight ratio) and more preferably an appropriate ratio in a range of 0.1 to 100 times (weight ratio), to the content of the thiol compound of the present invention.

In the second resin composition of the present invention, the other thiol compound described above may be used together with the thiol compound of the present invention.

The ratio (proportion) of the contents between the thiol compound of the present invention and the other thiol compound in the second resin composition of the present invention is preferably set such that the content of the other thiol compound is preferably an appropriate portion in a range of 0 to 100 times (weight ratio) and more preferably an appropriate ratio in a range of 0.1 to 10 times (weight ratio), to the content of the thiol compound of the present invention.

Examples of a method for polymerizing (curing) the second resin composition of the present invention include methods of photo-curing and heat-curing.

Examples of the method of photo-curing include methods of irradiating active energy ray, preferably methods of concurrently using a photopolymerization initiator. The active energy ray includes light, radiation, electromagnetic wave, electron beams, and the like.

The photopolymerization initiator can be selected from a photo-radical polymerization initiator and a photo-anionic polymerization initiator, and the initiator may be added in the resin composition. In the photo-curing, the means of heat polymerization (heat-curing) may be concurrently used in order to enhance production efficiency and properties of a cured product.

Any photo-radical polymerization initiator generally used can be used without particular limitation. Examples thereof include:
acetophenones such as 2-hydroxy-2-methyl-1-phenylpropan-1-one, 1-hydroxycyclohexylphenyl ketone and 2-methyl-1-{4-(methylthio)phenyl}-2-morpholinopropan-1-one;
benzoins such as benzyldimethyl ketal;
benzophenones such as benzophenone, 4-phenylbenzophenone and hydroxybenzophenone;
thioxanthones such as isopropylthioxanthone and 2,4-diethylthioxantone; as well as
methylphenyl glyoxylate; and the like. Those may be used in combination.

As necessary, the photo-radical polymerization initiator can be used together with a conventional photopolymerization accelerator such as a benzoic acid such as 4-dimethylaminobenzoic acid, and a tertiary amine.

Any photo-anionic polymerization initiator generally used can be used without particular limitation. Examples thereof include onium salts, carbamates and the like.

Examples of the onium salt include 1,2-diisopropyl-3-[bis(dimethylamino)methylene]guanidium 2-(3-benzoylphenyl) propionate, 1,2-dicyclohexyl-4,4,5,5-tetramethyl biguanidium n-butyltriphenyl borate, and the like. Examples of the carbamate include 2-nitrophenylmethylpiperidine-1-carboxylate, 1-(anthraquinon-2-yl)ethylimidazole carboxylate, 1-[3-(2-hydroxyphenyl)-2-propenoyl]piperidine, 9-anthranylmethyldiethyl carbamate, and the like.

When the second resin composition of the present invention is photo cured, a sensitizer such as pyrene, perylene, acridine orange, thioxanthone, 2-chlorothioxanthone, and benzoflavin can be used for example.

The content of the photopolymerization initiator in the second resin composition of the present invention is preferably a proportion of 0.001 to 20 wt % and more preferably a proportion of 0.01 to 10 wt %, based on the entire second resin composition (total amount).

On the other hand, examples of a method for heat-curing the second resin composition of the present invention include methods of concurrently using a thermal polymerization initiator. The thermal polymerization initiator can be selected from a heat-radcial polymerization initiator and a heat-anionic polymerization initiator, and those may be added in the resin composition.

Any heat-radical polymerization initiator generally used can be used without particular limitation. Examples thereof include: peroxides such as diisopropyl peroxydicarbonate, benzoyl peroxide, t-butyl peroxyisobutyrate, t-hexyl peroxyisopropyl monocarbonate, t-hexyl peroxy 2-ethylhexanoate, 1,1,3,3-tetramethylbutyl peroxy 2-ethylhexanoate, t-butyl peroxypivalate, t-hexyl peroxypivalate, t-butyl peroxyneodecanoate, t-hexyl peroxyneodecanoate, 1,1,3,3-tetramethylbutyl peroxyneodecanoate, 1,1-bis(t-hexylperoxy)cyclohexane, benzoyl peroxide, 3,5,5-trimethylhexanoyl peroxide, and lauroyl peroxide; and azo compounds such as azobisisobutyronitrile, 2,2'-azobis(2-methylbutyronitrile) and dimethyl 2,2'-azobis(2-methylpropionate). Those may be used in combination.

Any heat-anionic polymerization initiator generally used can be used without particular limitation. Examples thereof include: amines and imidazoles. Those may be used in combination.

Examples of the amine include diethylenetriamine, triethylenetetramine, isophorone diamine, xylylene diamine, diaminodiphenylmethane, 1,3,4,6-tetrakis(3-aminopropyl) glycoluril, and the like. Examples of the imidazole include 2-methylimidazole, 2-ethyl-4-methylimidazole, 2-phenylimdazole, and the like.

The content of the thermal polymerization initiator in the second resin composition of the present invention is preferably a proportion of 0.001 to 20 wt % and more preferably a proportion of 0.01 to 10 wt %, based on the entire second resin composition (total amount).

In the second resin composition of the present invention, when an epoxy resin (epoxy compound) is contained as an additive (modifier), a photo-cationic polymerization initiator or a heat-cationic polymerization initiator may be used.

Any photo-cationic polymerization initiator generally used can be used without particular limitation. Examples thereof include onium salts, organometallic complexes and the like.

Examples of the onium salt include diazonium salts, sulfonium salts, iodonium salts, and the like.

Examples of the organometallic complex include iron-arene complexes, titanocene complexes, aryl silanol-aluminum complexes, and the like.

Examples of a commercially available photo-cationic polymerization initiator include "ADEKA OPTOMER SP-150 (trade name)" and "ADEKA OPTOMER SP-170 (trade name)", manufactured by ADEKA Corporation, "UVE-1014 (trade name)" manufactured by General Electronics, "CD-1012 (trade name)" manufactured by Sartomer Company, "CPI-100P (trade name)" manufactured by San-Apro Ltd, and the like.

Examples of a counter anion of the photo-cationic polymerization initiator include $SbF_6^-$, $AsF_6^-$, $B(C_6F_5)_4^-$, $PF_6^-$, and the like.

Any heat-cationic polymerization initiator generally used can be used without particular limitation. Examples thereof include various onium salts such as a quaternary ammonium salt, a phosphonium salt and a sulfonium salt, organometallic complexes, and the like. Those may be used in combination.

Examples of a commercially available onium salt include "ADEKA OPTON CP-66 (trade name)" and "ADEKA OPTON CP-77 (trade name)", manufactured by ADEKA Corporation, "SAN-AID SI-60L (trade name)", "SAN-AID SI-80L (trade name)" and "SAN-AID SI-100L (trade name)", manufactured by Sanshin Chemical Industry Co., Ltd., "CI Series (trade name)" manufactured by Nippon Soda Co., Ltd, and the like.

Examples of the organometallic complex include alkoxysilane-aluminum complexes.

As necessary, the second resin composition of the present invention may further contain the additive (modifier) described above for the first resin composition in a proportion of 0.01 to 50 wt % based on the entire second resin composition (total amount) so long as the effect of the present invention is not impaired.

A method for preparing (mixing) the second resin composition of the present invention is not particularly limited.

The second resin composition can be prepared by, for example, mixing the thiol compound of the present invention, an enic compound, another thiol compound, a photo-polymerization initiator and/or a thermal polymerization initiator, and an additive. As the mixing means, a conventional method can be used. The thiol compound of the present invention may be previously dissolved or dispersed in a diluent for viscosity adjustment (organic solvent).

The active energy ray used to cure the second resin composition of the present invention is preferably electron beams or light having a wavelength region of ultraviolet to infrared. As a light source, use can be made of, for example, an ultrahigh pressure mercury light source or a metal halide light source in the case of irradiation of ultraviolet rays, a metal halide light source or a halogen light source in the case of irradiation of visible light, and a halogen light source in the case of irradiation of infrared rays. Furthermore, light sources such as laser or LED corresponded to light emission of various wavelengths, the use of which is recently spreading, may be used.

The irradiation dose of the active energy rays can be appropriately set according to the kind of light source, and the like.

Regarding the conditions in the case of heating, heating temperature/heating time can be appropriately set in a range of 60 to 130° C./30 to 240 min, and preferably 70 to 125° C./30 to 120 min.

The first resin composition and second resin composition of the present invention containing the thiol compound of the present invention (those resin compositions are sometimes collectively called "the resin composition of the present invention") are expected to give a cured product having excellent hydrolysis resistance (water resistance).

In other words, the resin composition of the present invention gives a cured product having excellent moisture resistance as compared with a resin composition containing a conventional thiol compound, and therefore can be suitably used as an adhesive and a sealant. Specifically, the adhesive and sealant of the present invention contain the resin composition of the present invention as a component.

The adhesive and sealant of the present invention may contain an additive. Examples of the additive include flow behavior modifiers such as silicic acid, magnesium silicate and barium sulfate, thermal conductivity-imparting agents such as alumina, conductivity-imparting agents such as silver and carbon, coloring agents such as a pigment and a dye, and the like. Those additives can be mixed with the above-described resin composition of the present invention by using a conventionally-known general mixing machine such as three rolls and a planetary mixer.

The adhesive and sealant of the present invention can be applied to various fields without particular limitation in the uses. Examples of the use of the adhesive include: adhesives for a flexible printed wiring board; interlayer adhesives of a multilayered substrate such as a build-up substrate; adhesives for bonding optical parts; adhesives for laminating optical disc; adhesives for mounting a printed wiring board; die-bonding adhesives; adhesives for a semiconductor, such as an underfill; adhesives for mounting, such as an underfill for BGA reinforcement, an anisotropic conductive film (ACF), and an anisotropic conductive paste (ACP); adhesives for light pick-up; adhesives for bonding light path; adhesives used between an exterior material, base material or ceiling material and an interior material; adhesives for adhering a tile or stone to an exterior wall material or base material; adhesives for adhering a wooden flooring material, polymer material floor sheet or floor tile to various floors;

adhesives for a structural material, body or part of automobiles, aircrafts or the like; adhesives for automobile interior; adhesives for joint of steel plates; and the like.

Examples of the use of the sealant include: sealants for a joint of an exterior material such as various metal panels and siding boards; sealants used between an exterior material, a base material or a ceiling material and an interior material; sealants for a joint of various concrete products such as a road, bridge, tunnel or breakwater; sealants of a structural material, body or part of automobiles, aircrafts or the like; sealants for joint of steel plates; medical equipment sealants; and the like.

The resin composition of the present invention can be applied to products (parts and members) of various fields in which the material may be a resin, other than the above-described adhesive and sealant, and can be used in electric/electronic, optical, building, civil engineering, automobile/aircraft, and medical fields and further as a raw material of daily miscellaneous goods.

For example, examples of part/member and a material in electric/electronic fields include resin-attached copper foils, prepregs, copper-clad laminate plates, printed wiring boards, solder resist inks, conductive pastes, interlayer insulating materials, encapsulants, encapsulants for LED, insulating materials, thermal conductive materials, hot melt materials, paints, potting agents, and the like. More specific examples thereof include:

encapsulant materials and layer forming materials of a printed wiring board and an electronic part, such as an interlayer insulting film and a wiring coating film;

forming materials of a display device, such as a color filter, a film for flexible display, a resist material, and an oriented film;

forming materials of a semiconductor device, such as a resist material and a buffer coat film; and forming materials of an optical part, such as a hologram, an optical waveguide, an optical circuit, an optical circuit part, and an antireflection film.

The examples further include: forming materials of a rigid wiring board and a flexible printed wiring board, for mounting on a semiconductor; materials for mounting a semiconductor; encapsulants for a semiconductor; encapsulants for a solar cell; insulating films for a semiconductor; coverlay films for protecting a flexible printed circuit; coating agents for covering a wiring; and the like.

Examples of the material in an optical field include core materials for optical fiber, clad materials, lens, wear-resistant coating agents of a lens (e.g., a hard coat forming liquid), and the like.

Examples of the material in a building field include: coating materials and primers of an exterior material such as various metal panels and siding boards; grouting materials, damping materials, soundproof materials, conductive materials for shielding electromagnetic waves, and putties, used between an exterior material, base material or ceiling material and an interior material; pressure-sensitive adhesives for adhering a wooden flooring material, polymer material floor sheet or floor tile to various floors; grouting materials for repairing cracks of various exterior materials and interior materials; and the like.

Examples of the material in a civil engineering field include: coating materials of various concrete products such as a road, bridge, tunnel or breakwater; primers; paints; putties; grouting materials; spraying materials; molding materials; and the like.

Examples of the material in automobile and aircraft fields include: coating materials, cushioning materials, damping materials, soundproof materials and spraying materials of a structural material, body or part: pressure-sensitive adhesives, coating materials and foaming materials for interior decoration of automobiles; coating materials for a joint of steel plates; and the like.

Examples of the material in medical fields include artificial bones, dental impression materials, medical rubber materials, medical pressure-sensitive adhesive, and the like.

EXAMPLES

The present invention is described in more detail below by Examples (synthesis tests and evaluation tests) and Comparative Examples (evaluation tests), but it should be understood that the present invention is not construed as being limited to those.

Measurement method of storage modulus and measurement method of adhesive strength, in the evaluation tests used in Examples and Comparative Examples are as follows.

[Measurement of Storage Modulus]

A epoxy resin composition was cured (80° C./1 hour). Storage modulus E' (GPa) at 25° C. of the cured product obtained (test piece: length 20 mm×width 5 mm×thickness 1 mm) was measured (frequency: 1 Hz) by using a dynamic viscoelasticity measuring device ("Rheosol-G5000" manufactured by UBM).

It is judged that impact resistance of the cured product is excellent as the storage modulus is small (low elasticity).

[Measurement of Adhesive Strength (Moisture Resistance Test)]

Two blast-treated aluminum plates (length 100 mm×width 25 mm×thickness 1.6 mm) were used. A epoxy resin composition (adhesive) was applied to one surface of each aluminum plate on a region (length 12.5 mm×width 25 mm) in a range of 12.5 mm from either one edge (longitudinal direction).

Subsequently, the two aluminum plates were stuck such that those coated surfaces face to each other, and then heated (cured the epoxy resin composition under conditions of 80° C./1 hour) to prepare a test piece.

Tensile shear adhesive strength (MPa) of the test piece was measured in accordance with JIS K6850 before and after performing a high-temperature and high-pressure steam treatment (PCT treatment, 121° C./48 hours) by an autoclave.

Residual ratio of the tensile shear adhesive strength after the PCT treatment (hereinafter sometimes referred to as "strength residual ratio") was calculated from the measured values by the following equation.

Strength residual ratio (%)=(tensile shear adhesive strength after PCT treatment)/(tensile shear adhesive strength before PCT treatment)×100

It is judged that moisture resistance of a cured product is excellent as the strength residual ratio is larger, and it is recognized that the epoxy resin is suitable as an adhesive.

The case where an adhesive layer eluted by the PCT treatment and the measurement of tensile shear adhesive strength was impossible, was indicated as "N.D.".

Main raw materials used in the evaluation tests of Examples and Comparative Examples are as follows.

[Main Raw Materials]

(A) Curing Agent:

1,3,4,6-Tetrakis(2-mercaptoethyl)glycoluril (manufactured by Shikoku Chemicals Corporation, trade name "TS-G", see chemical formula (21), thiol equivalent: 100.4)

Pentaerythritol tetrakis(3-mercaptopropionate) (manufactured by SC Organic Chemical Co., Ltd., trade name "PEMP", see chemical formula (22), thiol equivalent: 122.2)

[Chem. 74]

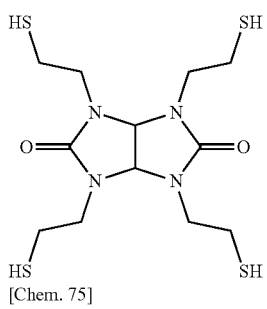

(21)

[Chem. 75]

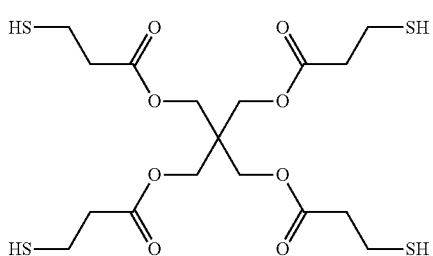

(22)

(B) Curing Accelerator:
Dimethylbenzylamine (manufactured by Wako Pure Chemical Industries Ltd.)
Microcapsule type amine adduct (manufactured by Asahi Kasei Corporation, latent curing type, trade name "NOVACURE HXA3922HP")
(C) Epoxy compound (epoxy resin):
Phenol novolac epoxy resin (manufactured by Mitsubishi Chemical Corporation, trade name "jER152", epoxy equivalent: 174.0)
Bisphenol A epoxy resin (manufactured by Mitsubishi Chemical Corporation, trade name "jER828", epoxy equivalent: 187.0)

Test Example 1

Main raw materials used in synthesis test of Test Example 1 are as follows.
[Main Raw Materials]
Benzaldehyde (manufactured by Wako Pure Chemical Industries Ltd., see chemical formula (1-1-6))
Cyclohexanone (manufactured by Wako Pure Chemical Industries Ltd., see chemical formula (1-2-1)) 3-Thiapentane-1,5-dithiol (manufactured by Maruzen Chemical Trading Co., Ltd., see chemical formula (2-5))

Example 1-1

In a four-necked eggplant-shaped flask having a volume of 1,000 ml were charged 19.63 g (200.0 mmol) of cyclohexanone, 154.32 g (1,000 mmol) of 3-thiapentane-1,5-dithiol, 1.00 g (10.0 mmol) of 35% hydrochloric acid, and 200.00 g of toluene, followed by stirring at 100° C. for 24 hours. The reaction mixture obtained was concentrated and purified by a silica gel column chromatography (hexane/ethyl acetate=5/1 (v/v)), to thereby obtain 62.20 g of a pale yellow liquid (yield: 80.0%).

$^1$H-NMR spectral data of the pale yellow liquid was as follows.

$^1$H-NMR (d$_6$-DMSO) δ: 2.72 (m, 16H), 2.53 (t, 2H), 1.79 (t, 4H), 1.56 (quin., 4H), 1.40 (quin., 2H)

IR spectral data of the pale yellow liquid was shown in the chart of FIG. 1.

It was identified from these spectral data that the pale yellow liquid obtained is the thiol compound represented by the chemical formula (I-2-5).

Example 1-2

An epoxy resin composition was prepared by mixing 178.9 parts by weight of the thiol compound (thiol equivalent: 178.9) synthesized in Example 1-1 as a curing agent, 13.9 parts by weight of dimethylbenzylamine as a curing accelerator and 174.0 parts by weight of jER152 as an epoxy compound. The amount of the curing accelerator used was adjusted such that gelation time (80° C.) of the epoxy resin composition is 2 minutes±20 seconds.

The epoxy resin composition was subjected to evaluation tests (measurement of storage modulus of cured product, and measurement of adhesive strength thereof when used as adhesive). Test results obtained are shown in Table 1.

Examples 1-3 to 1-6 and Comparative Examples 1-1 and 1-2

Epoxy resin compositions having compositions shown in Table 1 were prepared in the same manner as in Example 1-2, and those epoxy resin compositions were subjected to the evaluation tests. The test results obtained are shown in Table 1.

TABLE 1

|  |  |  | Example | | | | | Comparative Example | |
|---|---|---|---|---|---|---|---|---|---|
|  |  |  | 1-2 | 1-3 | 1-4 | 1-5 | 1-6 | 1-1 | 1-2 |
| Composition (parts by weight) | (A) Curing agent | Thiol compound of Example 1-1 | 178.9 | 663.3 | 153.9 | 130.6 | 69.9 | | |
|  |  | TS-G |  | 73.7 | 17.1 | 32.6 | 69.9 | | |
|  |  | PEMP |  |  |  |  |  | 122.2 | 122.2 |
|  | (B) Curing accelerator | Dimethylbenzylamine | 13.9 |  | 18.7 | 6.5 | 3.9 | 8.7 | 9.4 |
|  |  | NOVACURE HXA3922HP |  | 895.6 |  |  |  |  |  |
|  | (C) Epoxy compound | jER152 | 174.0 |  |  |  |  | 174.0 |  |
|  |  | jER828 |  | 187.0 | 187.0 | 187.0 | 187.0 |  | 187.0 |

TABLE 1-continued

|  |  |  | Example | | | | | Comparative Example | |
|---|---|---|---|---|---|---|---|---|---|
|  |  |  | 1-2 | 1-3 | 1-4 | 1-5 | 1-6 | 1-1 | 1-2 |
| Evaluation tests | Storage modulus E' (GPa) | | 0.3 | <0.1 | <0.1 | 1.2 | 3.2 | 3.9 | 0.1 |
| | Tensile shear adhesive strength (MPa) | Before PCT | 15.6 | 1.1 | 1.0 | 17.2 | 12.3 | 13.5 | 14.2 |
| | | After PCT | 4.6 | 1.2 | 1.2 | 12.8 | 17.1 | N.D. | N.D. |
| | | Strength residual ratio (%) | 29 | 109 | 120 | 74 | 139 | N.D. | N.D. |

Example 1-7

In a four-necked eggplant-shaped flask having a volume of 1,000 ml were charged 21.22 g (200.0 mmol) of benzaldehyde, 154.32 g (1,000 mmol) of 3-thiapentane-1,5-dithiol, 1.00 g (10.0 mmol) of 35% hydrochloric acid, and 200.00 g of toluene, followed by stirring at 100° C. for 24 hours. The reaction mixture obtained was concentrated and purified by a silica gel column chromatography (hexane/dichloromethane=6/4 (v/v)), to thereby obtain 66.13 g of a colorless liquid (yield: 80.5%).

$^1$H-NMR spectral data of the colorless liquid was as follows.

$^1$H-NMR ($d_6$-DMSO) δ: 7.45 (d, 1H), 7.37 (t, 2H), 7.31 (d, 2H), 5.36 (s, 1H), 2.72 (m, 16H), 2.58 (t, 2H)

Figure 2:
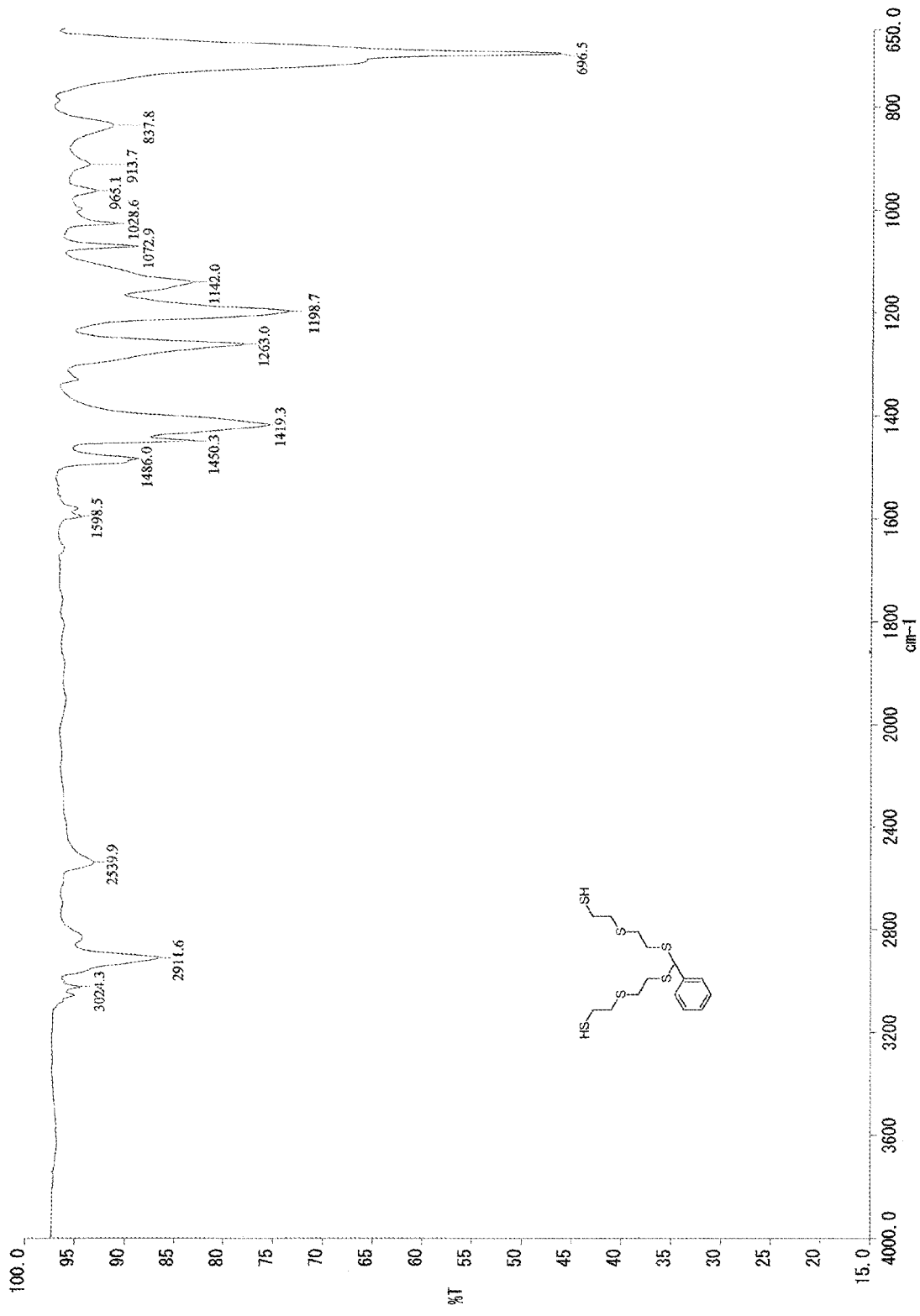
FIG. 2 is an IR spectral chart of a colorless liquid obtained in Example 1-7.

IR spectral data of the colorless liquid was shown in the chart of FIG. 2.

It was identified from these spectral data that the colorless liquid obtained is the thiol compound represented by the chemical formula (I-1-4).

Test Example 2

The main raw materials used in the synthesis test of Test Example 2 are as follows.

[Main Raw Materials]

(±)-Limonene (manufactured by Tokyo Chemical Industry Co., Ltd., see chemical formula (23))

3-Thiapentane-1,5-dithiol (manufactured by Maruzen Chemical Trading Co., Ltd., see chemical formula (3-5))

Azobisisobutyronitrile (manufactured by Wako Pure Chemical Industries Ltd.)

[Chem. 76]

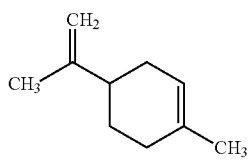

(23)

Example 2-1

In a four-necked eggplant-shaped flask having a volume of 500 ml were charged 20.43 g (150.0 mmol) of (±)-limonene, 115.74 g (750.0 mmol) of 3-thiapentane-1,5-dithiol, 0.25 g (1.5 mmol) of azobisisobutyronitrile, and 200.00 g of toluene, followed by stirring at 100° C. for 48 hours. The reaction mixture obtained was concentrated and purified by a silica gel column chromatography (hexane/ethyl acetate=5/1 (v/v)), to thereby obtain 50.72 g of a pale yellow liquid (yield: 76.0%).

$^1$H-NMR spectral data of the pale yellow liquid was as follows.

$^1$H-NMR ($d_6$-DMSO) δ: 2.70 (m, 16H), 2.52 (t, 2H), 2.38 (dt, 1H), 2.10-1.30 (m, 8H), 0.90 (m, 9H)

Figure 3:
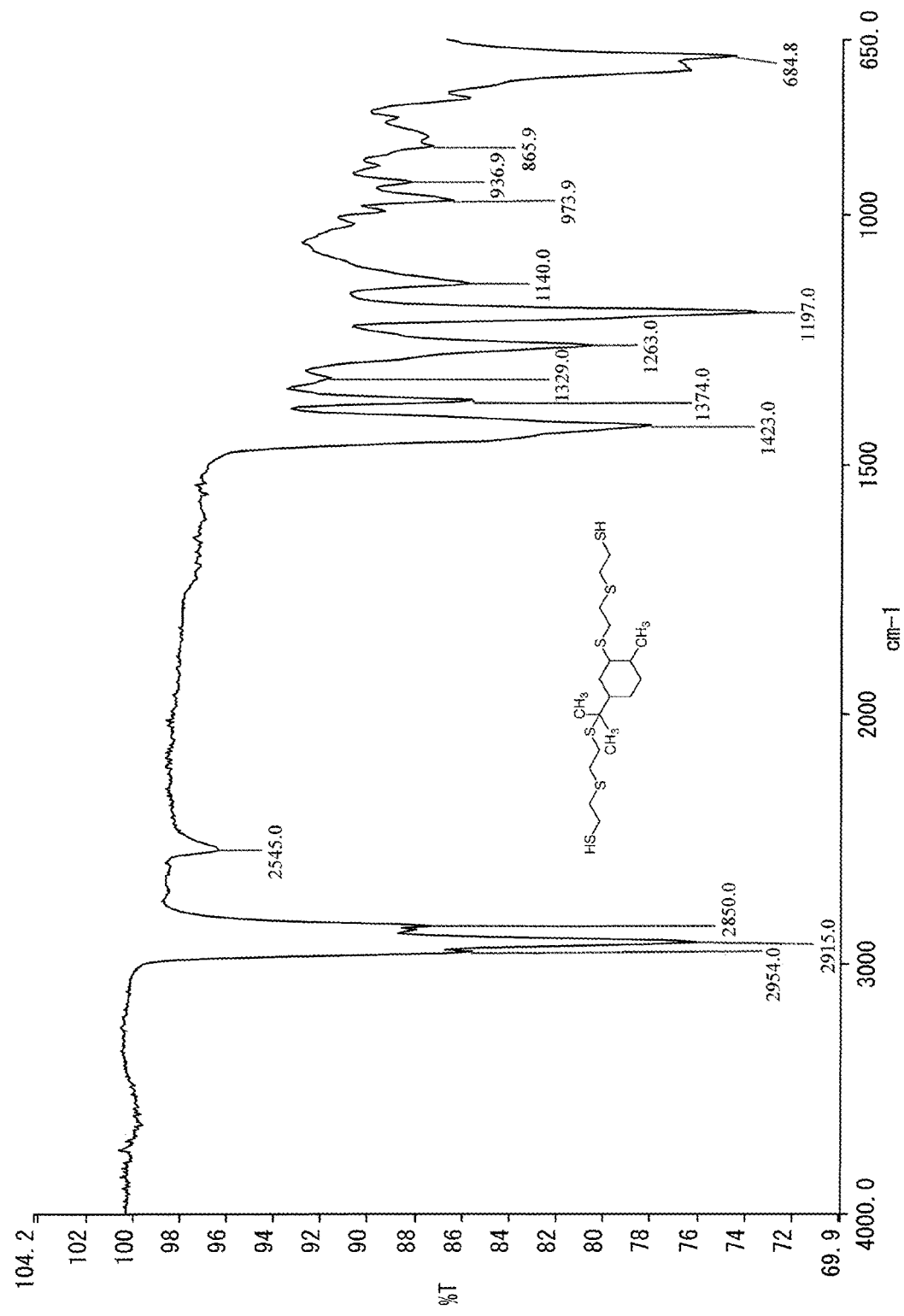
FIG. 3 is an IR spectral chart of a pale yellow liquid obtained in Example 2-1.

IR spectral data of the pale yellow liquid was shown in the chart of FIG. 3.

It was identified from these spectral data that the pale yellow liquid obtained is the thiol compound represented by the chemical formula (I-I-4).

Example 2-2

An epoxy resin composition was prepared by mixing 209.4 parts by weight of the thiol compound (thiol equivalent: 209.4) synthesized in Example 2-1 as a curing agent, 12.2 parts by weight of dimethylbenzylamine as a curing accelerator and 174.0 parts by weight of jER152 as an epoxy compound. The amount of the curing accelerator used was adjusted such that gelation time (80° C.) of the epoxy resin composition is 2 minutes±20 seconds.

The epoxy resin composition was subjected to evaluation tests (measurement of storage modulus of cured product, and measurement of adhesive strength thereof when used as adhesive). Test results obtained are shown in Table 2.

Examples 2-3 to 2-6 and Comparative Examples 2-1 and 2-2

Epoxy resin compositions having compositions shown in Table 2 were prepared in the same manner as in Example 2-2, and those epoxy resin compositions were subjected to the evaluation tests. The test results obtained are shown in Table 2.

TABLE 2

|  |  |  | Example | | | | | Comparative Example | |
|---|---|---|---|---|---|---|---|---|---|
|  |  |  | 2-2 | 2-3 | 2-4 | 2-5 | 2-6 | 2-1 | 2-2 |
| Composition (parts by | (A) Curing | Thiol compound of Example 2-1 | 209.4 | 771.2 | 178.6 | 150.1 | 77.5 | | |

TABLE 2-continued

|  |  |  | Example | | | | | Comparative Example | |
|---|---|---|---|---|---|---|---|---|---|
|  |  |  | 2-2 | 2-3 | 2-4 | 2-5 | 2-6 | 2-1 | 2-2 |
| weight) | agent | TS-G |  | 85.7 | 19.9 | 37.5 | 77.5 |  |  |
|  |  | PEMP |  |  |  |  |  | 122.2 | 122.2 |
|  | (B) | Dimethylbenzylamine | 12.2 |  | 18.7 | 7.5 | 3.6 | 8.7 | 9.4 |
|  | Curing accelerator | NOVACURE HXA3922HP |  | 895.6 |  |  |  |  |  |
|  | (C) Epoxy compound | jER152 | 174.0 |  |  |  |  | 174.0 |  |
|  |  | jER828 |  | 187.0 | 187.0 | 187.0 | 187.0 |  | 187.0 |
| Evaluation tests | Storage modulus E' (GPa) | | <0.1 | <0.1 | <0.1 | 0.1 | 3.4 | 3.9 | 0.1 |
|  | Tensile shear adhesive strength (MPa) | Before PCT | 2.5 | 5.1 | 4.7 | 11.6 | 10.8 | 13.5 | 14.2 |
|  |  | After PCT | 2.9 | 5.1 | 4.8 | 7.7 | 15.0 | N.D. | N.D. |
|  |  | Strength residual ratio (%) | 116 | 100 | 102 | 66 | 139 | N.D. | N.D. |

Test Example 3

Main raw materials used in the synthesis test of Test Example 3 are as follows.
[Main Raw Materials]1,3-Diallyl-2-imidazolidinone (synthesized in accordance with the method described in WO2002/036662. See chemical formula (4-1))
1,3-Diallyl-2-benzimidazolone (synthesized in accordance with the method described in J. Am. Chem. Soc., vol. 80, pp. 1657-1662 (1958). See chemical formula (5-1))
Thioacetic acid (manufactured by Tokyo Chemical Industry Co., Ltd., see chemical formula (13))
Azobisisobutyronitrile (manufactured by Wako Pure Chemical Industries Ltd.)

Example 3-1

Synthesis of 1,3-bis(3-mercaptopropyl)-2-imidazolidinone

Figure 4:
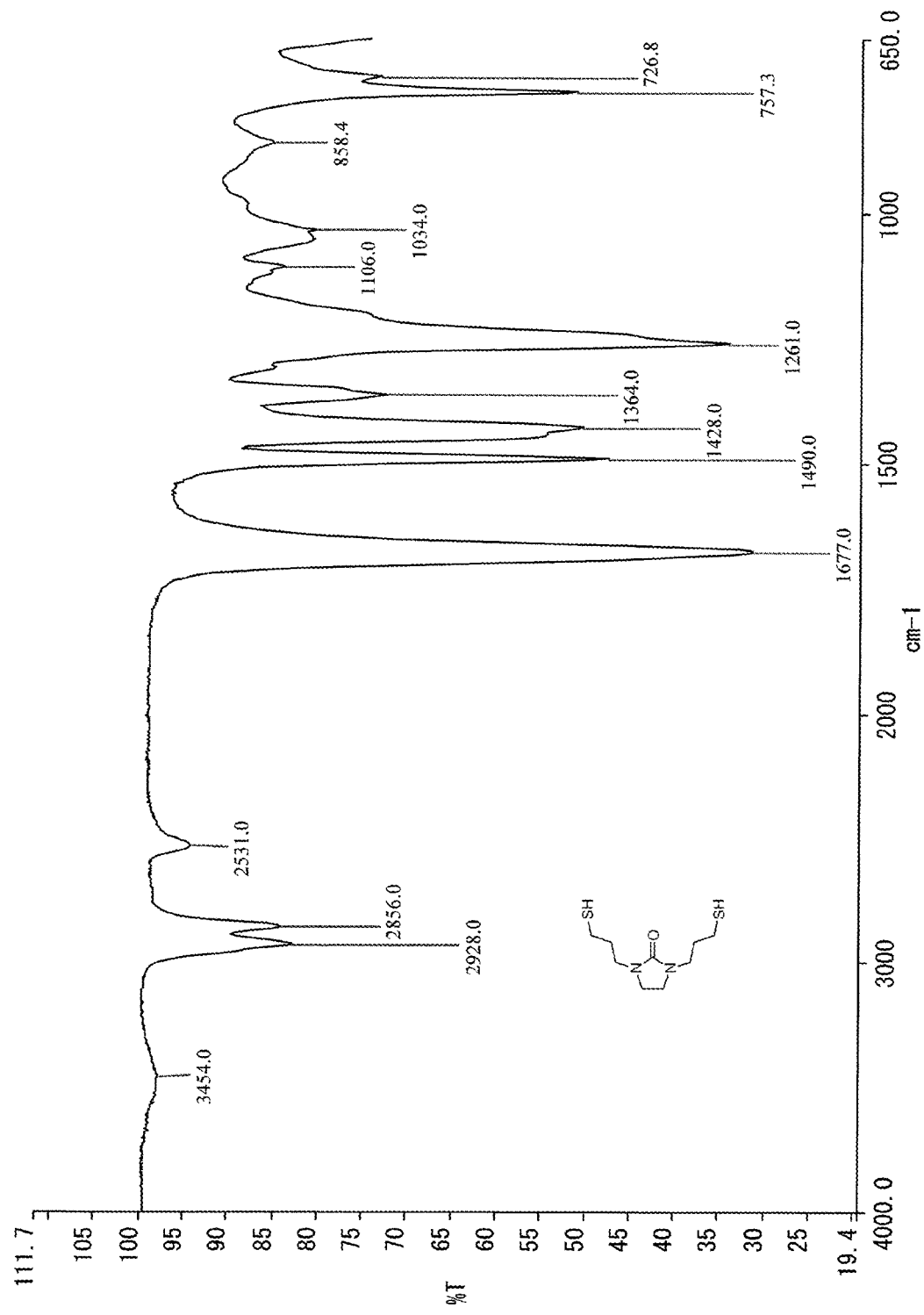
FIG. 4 is an IR spectral chart of a yellow liquid obtained in Example 3-1.

In a four-necked eggplant-shaped flask having a volume of 300 ml were charged 16.62 g (100.0 mmol) of 1,3-diallyl-2-imidazolidinone, 0.17 g (1.0 mmol) of azobisisobutyronitrile and 100.00 g of ethyl acetate, followed by heating to 50° C. Then, thereto was added dropwise 16.75 g (220.0 mmol) of thioacetic acid, followed by stirring at 60° C. for 15 hours. The resulting reaction liquid was concentrated, and to the reaction product obtained were added 0.49 g (5.0 mmol) of sulfuric acid and 100.00 g of methanol, followed by stirring at 60° C. for 24 hours. The reaction liquid obtained was concentrated and purified by a silica gel column chromatography (ethyl acetate/methanol=15/1 (v/v)), to thereby obtain 15.47 g of a yellow liquid (yield: 66.0%).
$^1$H-NMR spectral data of the yellow liquid was as follows.
$^1$H-NMR (d$_6$-DMSO) δ: 3.24 (s, 4H), 3.14 (t, 4H), 2.43 (t, 2H), 2.40 (dt, 4H), 1.70 (quin., 4H)
IR spectral data of the yellow liquid was shown in the chart of FIG. 4.
It was identified from these spectral data that the yellow liquid obtained is the captioned thiol compound represented by the chemical formula (III-1) (thiol equivalent: 128.1).

Example 3-2

Synthesis of 1,3-bis(3-mercaptopropyl)-2-benzimidazolone

Figure 5:
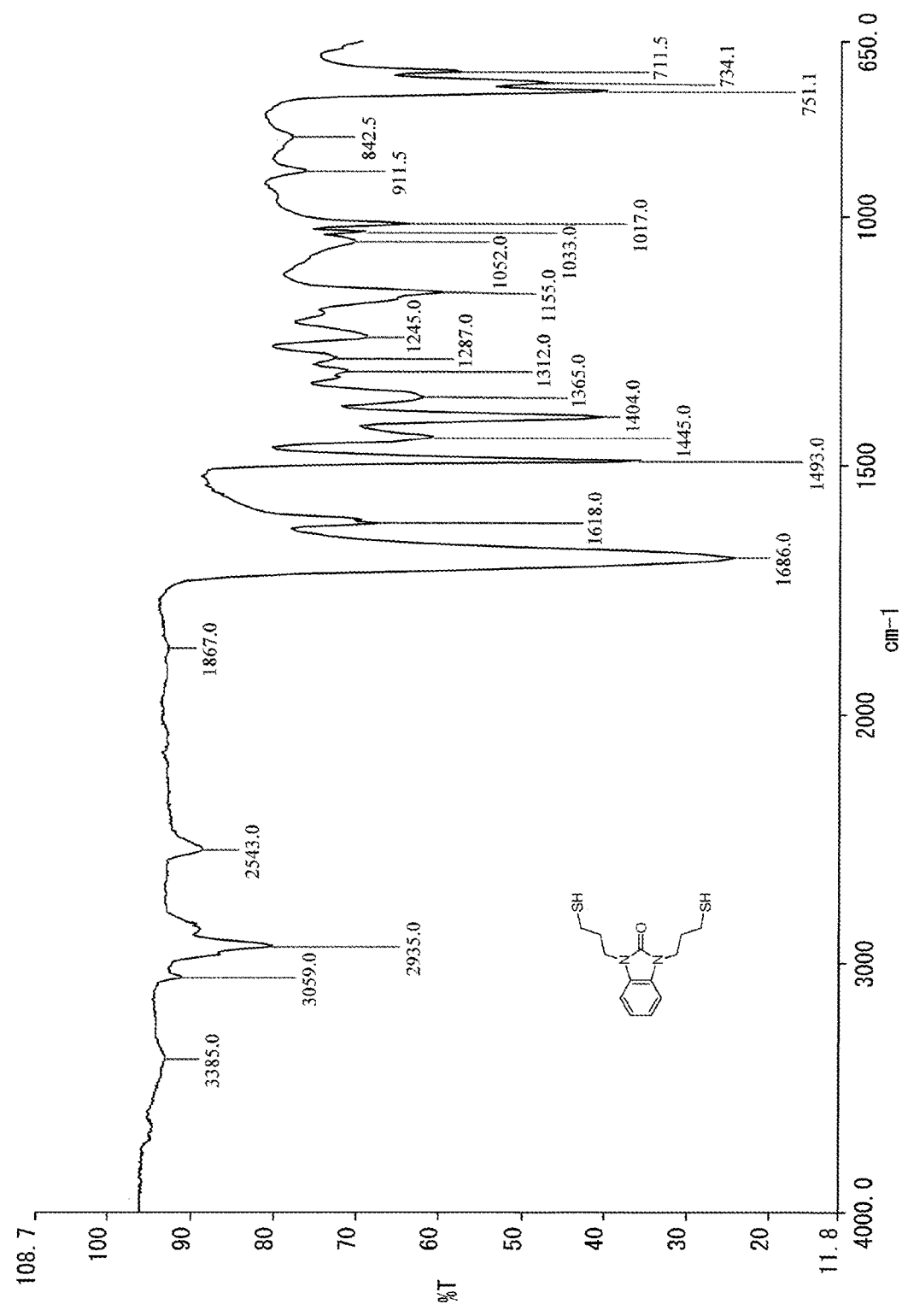
FIG. 5 is an IR spectral chart of a yellow liquid obtained in Example 3-2.

In a four-necked eggplant-shaped flask having a volume of 300 ml were charged 21.43 g (100.0 mmol) of 1,3-diallyl-2-benzimidazolone, 0.17 g (1.0 mmol) of azobisisobutyronitrile and 100.00 g of ethyl acetate, followed by heating to 50° C. Then, thereto was added dropwise 16.75 g (220.0 mmol) of thioacetic acid, followed by stirring at 60° C. for 15 hours. The resulting reaction liquid was concentrated, and to the reaction product obtained were added 0.49 g (5.0 mmol) of sulfuric acid and 100.00 g of methanol, followed by stirring at 60° C. for 24 hours. The reaction liquid obtained was concentrated and purified by a silica gel column chromatography (ethyl acetate/methanol=20/1 (v/v)), to thereby obtain 17.57 g of a yellow liquid (yield: 62.2%).
$^1$H-NMR spectral data of the yellow liquid was as follows.
$^1$H-NMR (d$_6$-DMSO) δ: 7.21 (q, 2H), 7.07 (q, 2H), 3.93 (t, 4H), 2.50 (t, 2H), 2.47 (dt, 4H), 1.91 (quin., 4H)
IR spectral data of the yellow liquid was shown in the chart of FIG. 5.
It was identified from these spectral data that the yellow liquid obtained is the captioned thiol compound represented by the chemical formula (IV-1) (thiol equivalent: 158.5).

Example 3-3

An epoxy resin composition was prepared by mixing 128.1 parts by weight of the thiol compound synthesized in Example 3-1 as a curing agent, 10.4 parts by weight of dimethylbenzylamine as a curing accelerator and 174.0 parts by weight of jER152 as an epoxy compound. The amount of the curing accelerator used was adjusted such that gelation time (80° C.) of the epoxy resin composition is 2 minutes±20 seconds.
The epoxy resin composition was subjected to evaluation tests (measurement of storage modulus of cured product, and measurement of adhesive strength thereof when used as adhesive). Test results obtained are shown in Table 3.

Examples 3-4 to 3-12 and Comparative Examples 3-1 and 3-2

Epoxy resin compositions having compositions shown in Table 3 were prepared in the same manner as in Example 3-3, and those epoxy resin compositions were subjected to the evaluation tests. The test results obtained are shown in Table 3.

TABLE 3

| | | | Example | | | | | | | | | | | Comparative Example | |
|---|---|---|---|---|---|---|---|---|---|---|---|---|---|---|---|
| | | | 3-3 | 3-4 | 3-5 | 3-6 | 3-7 | 3-8 | 3-9 | 3-10 | 3-11 | 3-12 | 3-1 | 3-2 |
| Composition (parts by weight) | (A) Curing agent | Thiol compound of Example 3-1 | 128.1 | 242.8 | 112.8 | 98.0 | 57.2 | | | | | | | |
| | | Thiol compound of Example 3-2 | | | | | | 158.5 | 252.0 | 137.4 | 117.5 | 64.7 | | |
| | | TS-G | | 27.0 | 12.5 | 24.5 | 57.2 | | 28.0 | 15.3 | 29.4 | 64.7 | | |
| | | PEMP | | | | | | | | | | | 122.2 | 122.2 |
| | (B) Curing accelerator | Dimethylbenzylamine | 10.4 | | 6.5 | 5.2 | 4.5 | 7.0 | | 4.7 | 3.7 | 2.2 | 8.7 | 9.4 |
| | | NOVACURE HXA3922HP | | 311.4 | | | | | 225.1 | | | | | |
| | (C) Epoxy compound | jER152 | 174.0 | | | | | 174.0 | | | | | 174.0 | |
| | | jER828 | | 187.0 | 187.0 | 187.0 | 187.0 | | 187.0 | 187.0 | 187.0 | 187.0 | | 187.0 |
| Evaluation tests | Storage modulus E' (GPa) | | 3.7 | 3.2 | 3.1 | 3.3 | 3.3 | 5.3 | 4.3 | 4.3 | 4.6 | 4.2 | 3.9 | 0.1 |
| | Tensile shear adhesive strength (MPa) | Before PCT | 13.6 | 14.5 | 13.9 | 15.6 | 13.6 | 13.3 | 13.6 | 12.1 | 13.1 | 12.7 | 13.5 | 14.2 |
| | | After PCT | 7.3 | 10.6 | 10.4 | 17.5 | 19.6 | 19.0 | 15.0 | 13.7 | 22.9 | 22.5 | N.D. | N.D |
| | | Strength residual ratio (%) | 54 | 73 | 75 | 112 | 144 | 143 | 110 | 113 | 175 | 177 | N.D. | N.D |

Test Example 4

The main raw materials used in the synthesis test of Test Example 4 are as follows.

[Main Raw Materials]

1-Allyl-2-aryloxybenzene (synthesized in accordance with the method described in J. Am. Chem. Soc., vol. 81, pp. 2705-2715 (1959). See chemical formula (6-2))

1,3-Bisallyloxybenzene (synthesized in accordance with the method described in J. Am. Chem. Soc., vol. 130, pp. 237-244 (2008). See chemical formula (7-3))

1,3-Bis(3-butenyl-1-oxy)benzene (synthesized in accordance with the method described in European Polymer Journal, vol. 95, pp. 503-513 (2017). See chemical formula (7-6))

Thioacetic acid (manufactured by Tokyo Chemical Industry Co., Ltd., see chemical formula (13))

Azobisisobutyronitrile (manufactured by Wako Pure Chemical Industries Ltd.)

Example 4-1

Synthesis of 1-(3-mercaptopropyl)-2-(3-mercaptopropyloxy)benzene

In a four-necked eggplant-shaped flask having a volume of 300 ml were charged 13.42 g (100.0 mmol) of 1-allyl-2-allyloxybenzene, 0.17 g (1.0 mmol) of azobisisobutyronitrile and 100.00 g of ethyl acetate, followed by heating to 50° C. Then, thereto was added dropwise 16.75 g (220.0 mmol) of thioacetic acid, followed by stirring at 60° C. for 15 hours. The resulting reaction liquid was concentrated, and to the reaction product obtained were added 0.49 g (5.0 mmol) of sulfuric acid and 100.00 g of methanol, followed by stirring at 60° C. for 24 hours. The reaction liquid obtained was concentrated and purified by a silica gel column chromatography (ethyl acetate/methanol=20/1 (v/v)), to thereby obtain 14.74 g of a yellow liquid (yield: 60.8%).

$^1$H-NMR spectral data of the yellow liquid was as follows.

$^1$H-NMR (d$_6$-DMSO) δ: 7.15 (t, 1H), 7.12 (d, 1H), 6.94 (d, 1H), 6.85 (t, 1H), 4.05 (t, 2H), 2.65 (m, 4H), 2.47 (t, 2H), 2.39 (t, 1H), 2.27 (t, 1H), 2.01 (quin., 2H), 1.78 (quin., 2H)

Figure 6:
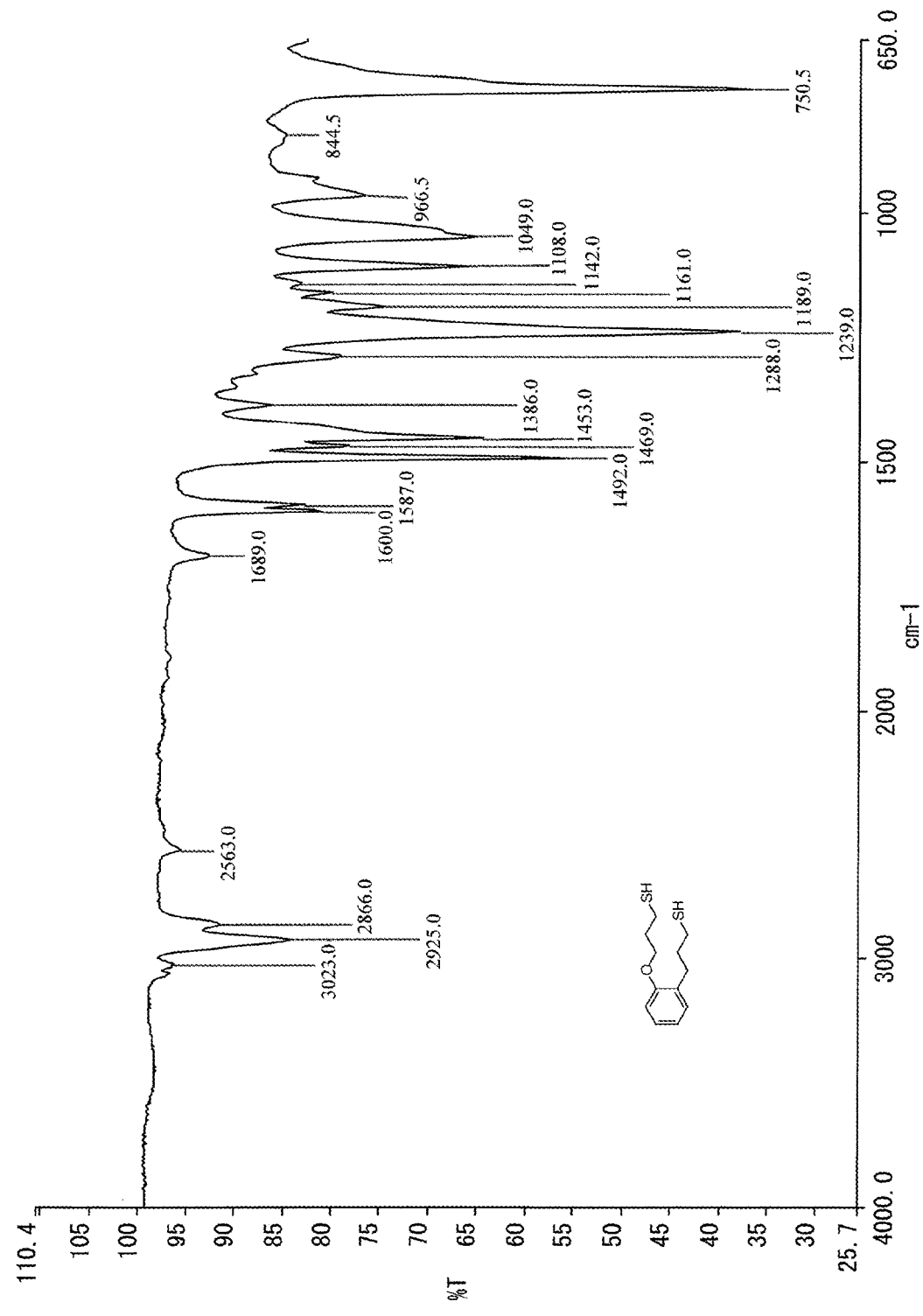
FIG. 6 is an IR spectral chart of a yellow liquid obtained in Example 4-1.

IR spectral data of the yellow liquid was shown in the chart of FIG. 6.

It was identified from these spectral data that the yellow liquid obtained is the captioned thiol compound represented by the chemical formula (V-2).

Example 4-2

An epoxy resin composition was prepared by mixing 131.8 parts by weight of the thiol compound (thiol equivalent: 131.8) synthesized in Example 4-1 as a curing agent, 6.1 parts by weight of dimethylbenzylamine as a curing accelerator and 174.0 parts by weight of jER152 as an epoxy compound. The amount of the curing accelerator used was adjusted such that gelation time (80° C.) of the epoxy resin composition is 2 minutes±20 seconds.

The epoxy resin composition was subjected to evaluation tests (measurement of storage modulus of cured product, and measurement of adhesive strength thereof when used as adhesive). Test results obtained are shown in Table 4.

Examples 4-3 to 4-6 and Comparative Examples 4-1 and 4-2

Epoxy resin compositions having compositions shown in Table 4 were prepared in the same manner as in Example 4-2, and those epoxy resin compositions were subjected to the evaluation tests. The test results obtained are shown in Table 4.

TABLE 4

|  |  |  | Example 4-2 | Example 4-3 | Example 4-4 | Example 4-5 | Example 4-6 | Comparative Example 4-1 | Comparative Example 4-2 |
|---|---|---|---|---|---|---|---|---|---|
| Composition (parts by weight) | (A) Curing agent | Thiol compound of Example 4-1 | 131.8 | 191.7 | 115.8 | 100.4 | 58.1 | | |
| | | TS-G | | 21.3 | 12.9 | 12.6 | 58.1 | | |
| | | PEMP | | | | | | 122.2 | 122.2 |
| | (B) Curing accelerator | Dimethylbenzylamine | 6.1 | | 3.7 | 2.8 | 2.4 | 8.7 | 9.4 |
| | | NOVACURE HXA3922HP | | 177.2 | | | | | |
| | (C) Epoxy compound | jER152 | 174.0 | | | | | 174.0 | |
| | | jER828 | | 187.0 | 187.0 | 187.0 | 187.0 | | 187.0 |
| Evaluation tests | | Storage modulus E' (GPa) | 3.1 | 3.5 | 3.4 | 3.7 | 3.7 | 3.9 | 0.1 |
| | Tensile shear adhesive strength (MPa) | Before PCT | 15.7 | 15.7 | 12.6 | 14.3 | 15.7 | 13.5 | 14.2 |
| | | After PCT | 16.1 | 17.9 | 14.8 | 18.7 | 22.4 | N.D. | N.D. |
| | | Strength residual ratio (%) | 103 | 114 | 117 | 131 | 143 | N.D. | N.D. |

Example 4-7

Synthesis of 1,3-bis(3-mercaptopropyloxy)benzene

In a four-necked eggplant-shaped flask having a volume of 300 ml were charged 19.02 g (100.0 mmol) of 1,3-bisallyloxybenzene, 0.17 g (1.0 mmol) of azobisisobutyronitrile and 100.00 g of butyl acetate, followed by heating to 50° C. Then, thereto was added dropwise 16.75 g (220.0 mmol) of thioacetic acid, followed by stirring at 60° C. for 15 hours. The resulting reaction liquid was concentrated, and to the reaction product obtained were added 0.49 g (5.0 mmol) of sulfuric acid and 100.00 g of methanol, followed by stirring at 60° C. for 24 hours. The reaction liquid obtained was concentrated and purified by a silica gel column chromatography (toluene/hexane=8/2 (v/v)), to thereby obtain 21.29 g of a yellow liquid (yield: 82.4%).

$^1$H-NMR spectral data of the yellow liquid was as follows.

$^1$H-NMR ($d_6$-DMSO) δ: 7.16 (t, 1H), 6.52 (d, 2H), 6.49 (s, 1H), 4.03 (t, 4H), 2.62 (dt, 4H), 2.42 (t, 2H), 1.96 (quin., 4H)

Figure 7:
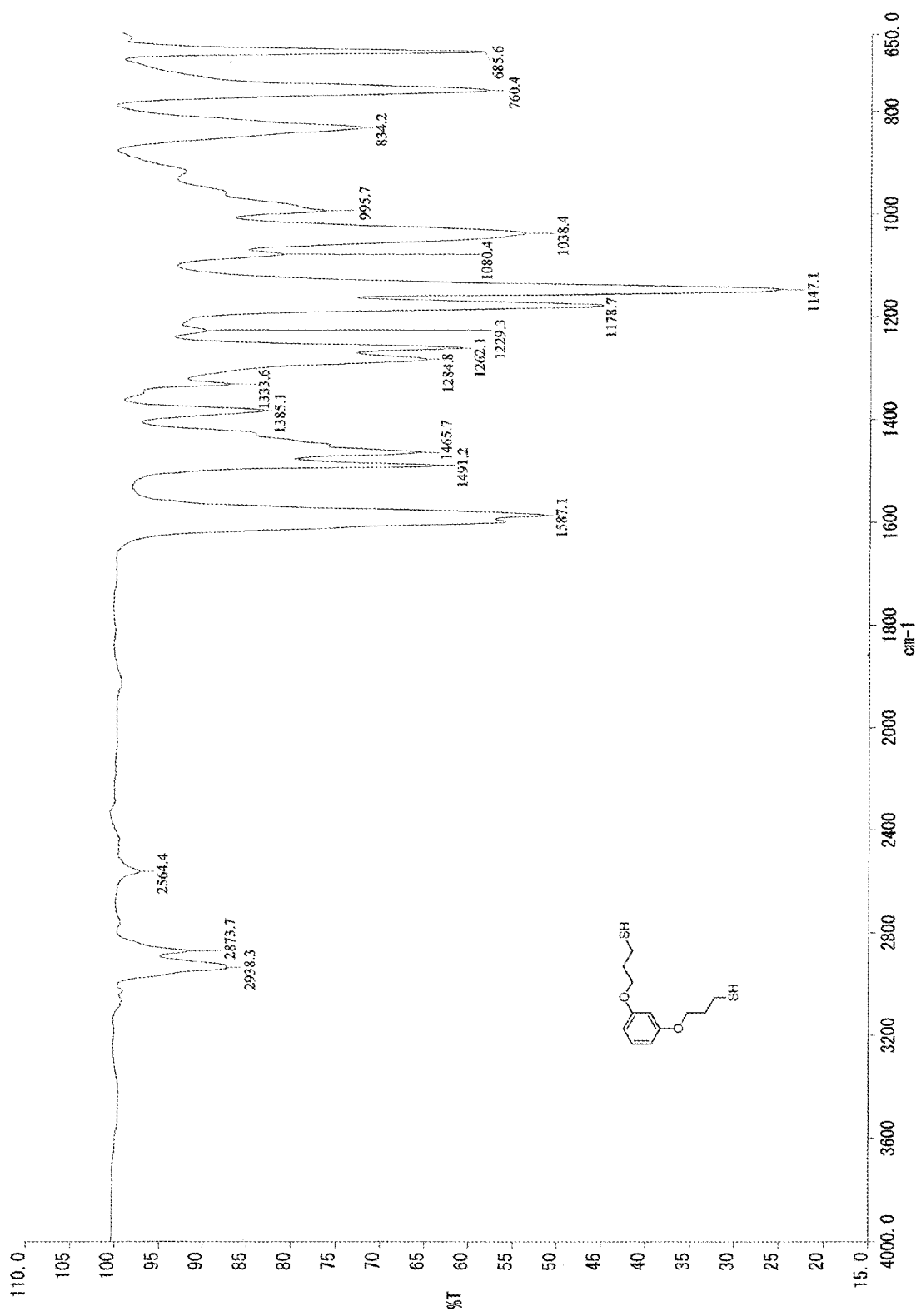
FIG. 7 is an IR spectral chart of a yellow liquid obtained in Example 4-7.

IR spectral data of the yellow liquid was shown in the chart of FIG. 7.

It was identified from these spectral data that the yellow liquid obtained is the captioned thiol compound represented by the chemical formula (VI-3).

Example 4-8

Synthesis of 1,3-bis(4-mercaptobutyloxy)benzene

In a four-necked eggplant-shaped flask having a volume of 300 ml were charged 21.82 g (100.0 mmol) of 1,3-bis(3-butenyl-1-oxy)benzene, 0.17 g (1.0 mmol) of azobisisobutyronitrile and 100.00 g of butyl acetate, followed by heating to 50° C. Then, thereto was added dropwise 16.75 g (220.0 mmol) of thioacetic acid, followed by stirring at 60° C. for 15 hours. The resulting reaction liquid was concentrated, and to the reaction product obtained were added 0.49 g (5.0 mmol) of sulfuric acid and 100.00 g of methanol, followed by stirring at 60° C. for 24 hours. The reaction liquid obtained was concentrated and purified by a silica gel column chromatography (toluene/hexane=8/2 (v/v)), to thereby obtain 20.02 g of a brown liquid (yield: 69.9%).

$^1$H-NMR spectral data of the brown liquid was as follows.

$^1$H-NMR ($d_6$-DMSO) δ: 7.14 (t, 1H), 6.49 (d, 2H), 6.46 (s, 1H), 3.94 (t, 4H), 2.53 (dt, 4H), 2.28 (t, 2H), 1.76 (quin., 4H), 1.66 (quin., 4H)

Figure 8:
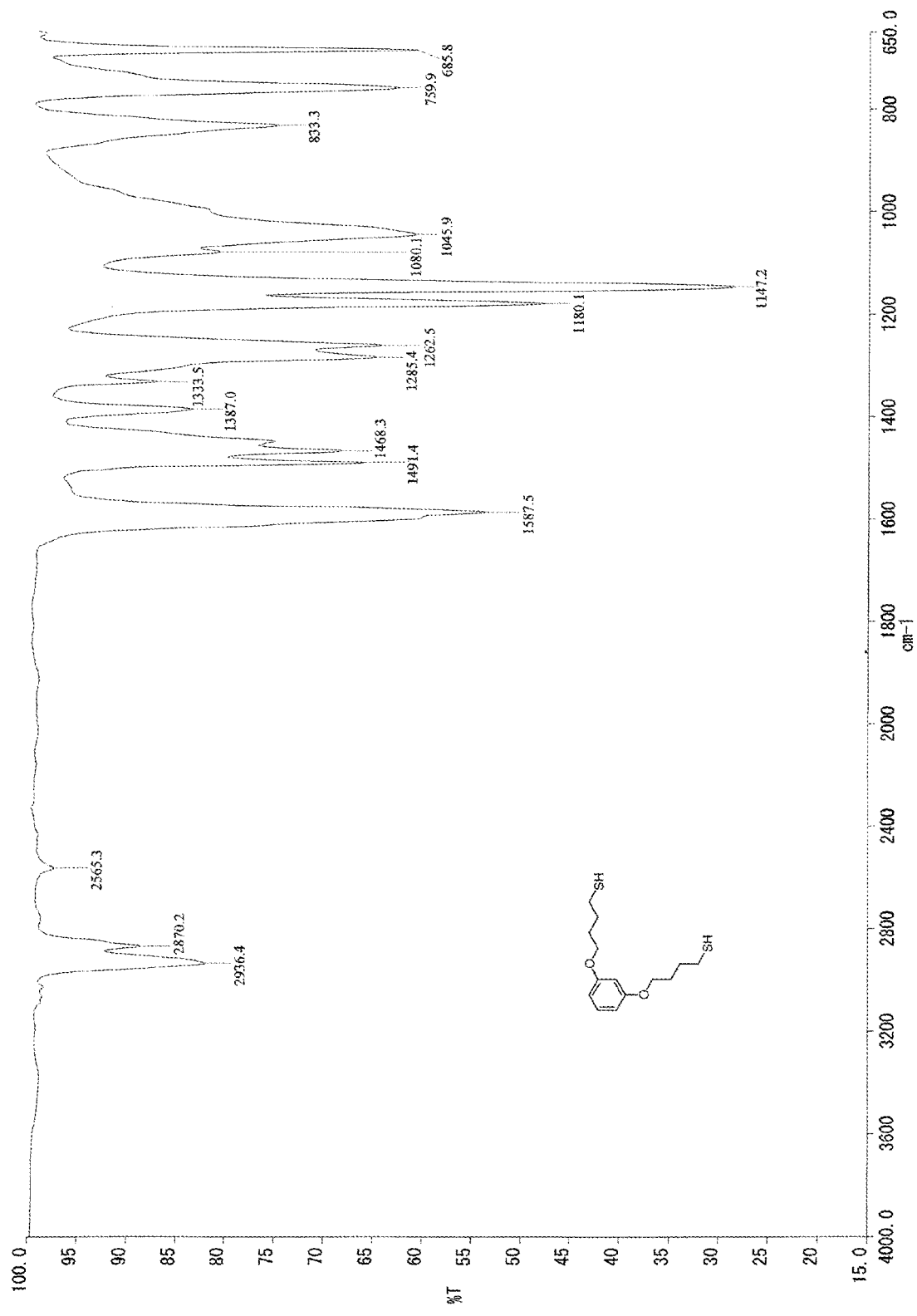
FIG. 8 is an IR spectral chart of a brown liquid obtained in Example 4-8.

IR spectral data of the brown liquid was shown in the chart of FIG. 8.

It was identified from these spectral data that the brown liquid obtained is the captioned thiol compound represented by the chemical formula (VI-6).

Although the present invention has been described in detail and by reference to the specific embodiments, it is apparent to one skilled in the art that various modifications and changes can be made without departing the spirit and scope of the present invention. This application is based on Japanese Patent Application (No. 2017-206993) filed on Oct. 26, 2017, and Japanese Patent Applications (No. 2017-213168, No. 2017-213211 and No. 2017-213229) filed on Nov. 2, 2017, the disclosures of which are incorporated herein by reference in their entities. All references referred here are also incorporated herein in their entities.

INDUSTRIAL APPLICABILITY

The thiol compound of the present invention is expected to be useful as an intermediate raw material of various sulfur-containing compounds and a curing agent for resins.

Furthermore, the resin composition containing the thiol compound of the present invention is suitable for various uses such as adhesion, sealing, encapsulation, casting, molding, painting and coating.

The invention claimed is:

1. A thiol compound represented by the chemical formula (I-2):

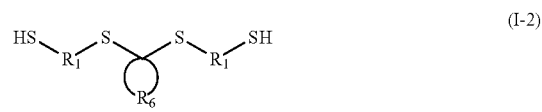

in the formula (I-2), $R_1$'s are the same or different and represent a straight chain alkylene group having a carbon number of 1 to 10, a branched chain alkylene group having a carbon number of 2 to 10, or a divalent organic group represented by each formula of

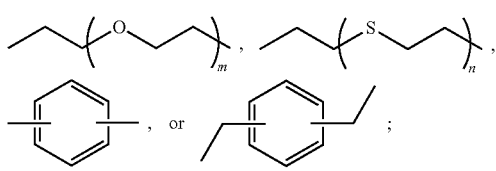

R₆ represents

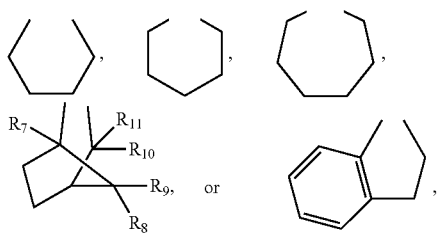

wherein $R_7$, $R_8$, $R_9$, $R_{10}$, and $R_{11}$ are the same or different and represent a hydrogen atom or a methyl group;
m is an integer of 1 to 5; and
n is an integer of 1 to 5.

2. A curing agent comprising the thiol compound as described in claim 1.

3. A resin composition comprising the thiol compound as described in claim 1 and an epoxy compound.

4. The resin composition according to claim 3, comprising an amine as a curing accelerator.

5. The resin composition according to claim 3, comprising a reaction product between an epoxy compound and an amine, as a curing accelerator.

6. The resin composition according to claim 3, comprising a reaction product between a compound having one or more isocyanate group in the molecule and a compound having at least one of a primary amino group and a secondary amino group in the molecule, as a curing accelerator.

7. A resin composition comprising the thiol compound as described in claim 1 and an enic compound having a carbon-carbon double bond in the molecule.

8. An adhesive comprising the resin composition as described in claim 3 as a component.

9. A sealant comprising the resin composition as described in claim 3 as a component.

10. An adhesive comprising the resin composition as described in claim 7 as a component.

11. A sealant comprising the resin composition as described in claim 7 as a component.

* * * * *